US008461416B2

(12) United States Patent
Niblett

(10) Patent No.: US 8,461,416 B2
(45) Date of Patent: Jun. 11, 2013

(54) METHODS AND MATERIALS FOR CONFERRING RESISTANCE TO PESTS AND PATHOGENS OF PLANTS

(75) Inventor: Charles L. Niblett, Raleigh, NC (US)

(73) Assignee: Venganza, Inc., Raleigh, NC (US)

( * ) Notice: Subject to any disclaimer, the term of this patent is extended or adjusted under 35 U.S.C. 154(b) by 0 days.

(21) Appl. No.: 13/171,117

(22) Filed: Jun. 28, 2011

(65) Prior Publication Data

US 2012/0023618 A1 Jan. 26, 2012

Related U.S. Application Data

(62) Division of application No. 11/256,428, filed on Oct. 21, 2005, now Pat. No. 8,148,604.

(60) Provisional application No. 60/657,821, filed on Mar. 1, 2005, provisional application No. 60/621,542, filed on Oct. 21, 2004.

(51) Int. Cl.

| | |
|---|---|
| ***C12N 15/00*** | (2006.01) |
| ***C12N 15/09*** | (2006.01) |
| ***C12N 15/82*** | (2006.01) |
| ***C12N 15/31*** | (2006.01) |

(52) U.S. Cl.
USPC ........... 800/279; 800/278; 800/298; 800/288; 435/418; 435/468; 435/419

(58) Field of Classification Search
None
See application file for complete search history.

(56) References Cited

U.S. PATENT DOCUMENTS

| | | | |
|---|---|---|---|
| 5,689,045 | A | 11/1997 | Logemann et al. |
| 5,858,774 | A | 1/1999 | Malbon et al. |
| 6,008,436 | A | 12/1999 | Conkling et al. |
| 6,133,245 | A | 10/2000 | Malbon et al. |
| 6,146,886 | A | 11/2000 | Thompson |
| 6,184,439 | B1 | 2/2001 | Fabijanski et al. |
| 6,369,038 | B1 | 4/2002 | Blumenfeld et al. |
| 6,423,885 | B1 | 7/2002 | Watterhouse et al. |
| 6,506,559 | B1 | 1/2003 | Fire et al. |
| 6,531,647 | B1 | 3/2003 | Baulcombe |
| 6,573,099 | B2 | 6/2003 | Graham |
| 6,608,241 | B1 | 8/2003 | Beachy et al. |
| 6,846,482 | B2 | 1/2005 | Liu |
| 7,078,196 | B2 | 7/2006 | Tuschl |
| 7,109,393 | B2 | 9/2006 | Gutterson |
| 7,422,853 | B1 | 9/2008 | Huang |
| 7,456,335 | B2 | 11/2008 | Kogel |
| 7,741,531 | B2 | 6/2010 | Baltz et al. |
| 7,803,984 | B2 | 9/2010 | Trick et al. |
| 8,097,710 | B2 | 1/2012 | Baulcombe |
| 8,148,604 | B2 | 4/2012 | Niblett |
| 2003/0051263 | A1 | 3/2003 | Fire et al. |
| 2003/0055020 | A1 | 3/2003 | Fire et al. |
| 2003/0056235 | A1 | 3/2003 | Fire et al. |
| 2003/0114413 | A1 | 6/2003 | Basler et al. |
| 2003/0150017 | A1 | 8/2003 | Mesa et al. |
| 2003/0175783 | A1 | 9/2003 | Waterhouse et al. |
| 2003/0180945 | A1 | 9/2003 | Wang et al. |
| 2003/0186911 | A1 | 10/2003 | Goodchild et al. |
| 2004/0029275 | A1 | 2/2004 | Brown |
| 2004/0029283 | A1 | 2/2004 | Fillatti |
| 2004/0098761 | A1 | 5/2004 | Trick et al. |
| 2004/0133943 | A1 | 7/2004 | Plaetinck et al. |
| 2004/0147475 | A1 | 7/2004 | Li et al. |
| 2004/0158889 | A1 | 8/2004 | Depicker et al. |
| 2004/0203145 | A1 | 10/2004 | Zamore et al. |
| 2004/0214330 | A1 | 10/2004 | Waterhouse et al. |
| 2005/0080032 | A1 | 4/2005 | Gross et al. |
| 2005/0091713 | A1 | 4/2005 | Atkinson et al. |
| 2005/0102710 | A1 | 5/2005 | Baulcombe et al. |
| 2005/0120415 | A1 | 6/2005 | Aukerman |
| 2005/0138689 | A1 | 6/2005 | Aukerman |
| 2005/0158844 | A1 | 7/2005 | Brody et al. |
| 2006/0009402 | A1 | 1/2006 | Zamore et al. |
| 2006/0080749 | A1 | 4/2006 | Hussey et al. |
| 2006/0247197 | A1 | 11/2006 | Van De Craen et al. |
| 2007/0061918 | A1 | 3/2007 | Baltz et al. |
| 2011/0289626 | A1 | 11/2011 | Niblett |

FOREIGN PATENT DOCUMENTS

| | | |
|---|---|---|
| EP | 1416049 | 5/2004 |
| EP | 1484415 | 12/2004 |
| GB | 2362885 | 12/2001 |
| WO | WO 90/14090 | 11/1990 |
| WO | WO 99/32619 | 1/1999 |
| WO | WO 99/15682 | 4/1999 |
| WO | WO 99/53050 | 10/1999 |

(Continued)

OTHER PUBLICATIONS

Lin, X et al "siRNA-mediated off-target gene silencing triggered by a 7 nt complementation," *Nucleic Acids Research,* 2005, 33(14):4527-4535.
Jackson, A. L. et al, "Expression profiling reveals off-target gene regulation by RNAi," *Nat. Biotech.,* 2003, 21(6):635-638.
Bakhetia et al, Trends in Plant Science, 2005, 10: 362-367.
Brenda Bass, Cell (2000) 101:235-238.
Escobar et al., "RNAi-Mediated Oncogene Silencing Confers Resistance to Crown Gall Tumorigenesis," 2001, Proc. Natl. Acad. Sci. USA 6:98(23):13437-13442.
Fire et al. "Potent and specific genetic interference by double-stranded RNA in *Caenorhabditis elegans*." Nature 391, 806-810, 1998.
Gordon, et al., "RNAi for insect-proof plants," Nature Biotech., 2007, 25(11): 1231-1232.

(Continued)

*Primary Examiner* — Medina A Ibrahim
(74) *Attorney, Agent, or Firm* — Myers Bigel Sibley & Sajovec, PA

(57) ABSTRACT

Methods and materials for conferring pest resistance to plants are provided. Plants are transformed with a silencing construct homologous to a gene of a plant pest that is essential for the survival, development, or pathogenicity of the pest. This results in the plant producing RNAi to the selected gene, which, when ingested by the pest results in silencing of the gene and a subsequent reduction of the pest's ability to harm the plant. In other embodiments, the pest's reduced ability to harm the plant is passed on to pest progeny. Methods and materials for depathogenesis of pests is also provided.

16 Claims, 19 Drawing Sheets

FOREIGN PATENT DOCUMENTS

| | | | |
|---|---|---|---|
| WO | WO 99/61631 | | 12/1999 |
| WO | WO 00/01846 | | 1/2000 |
| WO | WO 00/26346 | | 5/2000 |
| WO | WO 00/68374 | | 11/2000 |
| WO | WO 01/37564 | | 5/2001 |
| WO | WO 01/48183 | | 7/2001 |
| WO | WO 01/88121 | | 11/2001 |
| WO | WO 01/96584 | | 12/2001 |
| WO | WO 03/004644 | | 1/2003 |
| WO | WO 03/030939 | | 4/2003 |
| WO | WO 2004/015075 | | 2/2004 |
| WO | WO 2004/099417 | | 11/2004 |
| WO | WO 2005/049841 | A1 | 6/2005 |
| WO | WO 2005/071091 | | 8/2005 |
| WO | WO 2006/000410 | A2 | 1/2006 |
| WO | WO 2006/044480 | A2 | 4/2006 |
| WO | WO 2006/047495 | A2 | 5/2006 |
| WO | WO 2006/070227 | A2 | 7/2006 |

OTHER PUBLICATIONS

Kadotani, et al., "RNA silencing in the phytopathogenic fungus *Magnaporthe oryzae*," MPMI, 2003, 16(9): 769-776.

Kamath et al. "Systematic functional analysis of the *Caenorhabditis elegans* genome using RNAi", Nature, Jan. 16, 2003, pp. 231-237, vol. 421, No. 6920.

Kawchuk et al., "Sense and Antisense RNA-Mediated Resistance to Potato Leafroll Virus in Russet Burbank Potato Plants," 1991, Molecular Plant-Microbe Interactions 4(3): 247-253.

Lu et al, Nucleic Acid Res (2004) 32(21): 171e published on line.

Oeser et al, Molecular Plant-Microbe Interactions (1994), vol. 7(2), pp. 282-288.

Stahl et al, The Plant Cell, vol. 4, 621-629 (1992).

Sweigard et al, Mol Gen Genet (1992) 232: 183-190.

Tenllado, F., et al "Crude extracts of bacterially expressed dsRNA can be used to protect plants against virus infections", *BMC Biotechnology,* Mar. 20, 2003, p. 3, vol. 3.

Tenllado, F., et al "RNA interference as new biotechnological tool for the control of virus diseases in plants", *Virus Research,* 2004, pp. 85-96, vol. 102.

Thomas et al, The Plant Journal (2001) 25(4), pp. 417-425.

Waterhouse, P.M., et al "Virus resistance and gene silencing in plants can be induced by simultaneous expression of sense and antisense RNA", *Proc. Nat'l. Acad. Sci. USA,* Nov. 1998, pp. 13959-13964, vol. 95.

Intermediary plasmid pVZA1 pVZA3 with the pVZA100 Silencing Cassette

Tobacco plants

SEQUENCE LISTING

<160> NUMBER OF SEQ ID NOS: 69

<210> SEQ ID NO 1
<211> LENGTH: 38
<212> TYPE: DNA
<213> ORGANISM: Artificial
<220> FEATURE:
<223> OTHER INFORMATION: Primer VZA 1F

<400> SEQUENCE: 1
taaattagcg gccgcatgaa attcttcgct cgcagtag 38

-continued

<210> SEQ ID NO 2
<211> LENGTH: 35
<212> TYPE: DNA
<213> ORGANISM: Artificial
<220> FEATURE:
<223> OTHER INFORMATION: Primer VZA 2R

<400> SEQUENCE: 2
aaaaatccat ggtcaagcag aaccacggct tagtg 35

<210> SEQ ID NO 3
<211> LENGTH: 33
<212> TYPE: DNA
<213> ORGANISM: Artificial
<220> FEATURE:
<223> OTHER INFORMATION: Primer VZA 3F

<400> SEQUENCE: 3
aaataagggc ccatgaaatt cttcgctcgc agt 33

<210> SEQ ID NO 4
<211> LENGTH: 35
<212> TYPE: DNA
<213> ORGANISM: Artificial
<220> FEATURE:
<223> OTHER INFORMATION: Primer VZA 4R

<400> SEQUENCE: 4
aaatatctcg agtcaagcag aaccacggct tagtg 35

<210> SEQ ID NO 5
<211> LENGTH: 2201
<212> TYPE: DNA
<213> ORGANISM: Artificial
<220> FEATURE:
<223> OTHER INFORMATION: pVZA100 silencing construct

<400> SEQUENCE: 5
gggcccatga aattcttcgc tcgcagtaga tggcactcca gtcgttgccg tgtcgtcacg 60
gctcgcctac gatccgatta accgcagaca caccgattgt gcctgattca gagaggctcc 120
cactgaaacg agatgagcct ggctcacggt cgatgcgcag caccttcata ccatcttcac 180
aatgctcgaa cttgtcttcg gcaacggctt cgtcatcgcg tcggcgatca tgtcgtcggt 240
accaacatgg cgaagccgtt gcctcgtcct ccactaggtg gcgcaccaag tggaacttgt 300 tcataaatatg cttgctcttg ctgtgcttgc caggcttggc agttagatac atgcacgaca 360
tgttttcgcc gtgtatctcc ggagtcgcaa actcccagca tagttcgtca cagagtccac 420
gtagccactg tagatctctg gtaccttcat tcatagcaat atactctgct tccgttgtgc 480
tctgtgcgtt gatctcttgc tttcttgatc cgtacgaaac cacattgcca ttgacgaacg 540
tgacgaactg cctaacactc tttcggtcat cagggtcatt gcgtagtgag catcggtgta 600
gcacgtcaga ttcacgtcgt tcccggcaac aattgtccat cactagccgt ggttctgctt 660
gacactaagc cgtggttctg cttgactcga ggtagatctg agggtaaatt tctagttttt 720
ctccttcatt ttcttggtta ggaccctttt ctctttttat ttttttgagc tttgatcttt 780
ctttaaactg atctattttt taattgattg gttatggtgt aaatattaca tagctttaac 840
tgataatctg attactttat ttcgtgtgtc tatgatgatg atgatagtta cagaaccgac 900
gactcgtccg tcctgtagaa accccaaccc gtgaaatcaa aaaactcgac ggcctgtggg 960
cattcagtct ggatcgcgaa aactgtggaa ttgatcagcg ttggtgggaa agcgcgttac 1020
aagaaagccg ggcaattgct gtgccaggca gttttaacga tcagttcgcc gatgcagata 1080

```
ttcgtaatta tgcgggcaac gtctggtatc agcgcgaagt ctttataccg aaaggttggg   1140

caggccagcg tatcgtgctg cgtttcgatg cggtcactca ttacggcaaa gtgtgggtca   1200

ataatcagga agtgatggag catcagggcg gctatacgcc atttgaagcc gatgtcacgc   1260

cgtatgttat tgccgggaaa agtgtacgta tcaccgtttg tgtgaacaac gaactgaact   1320

ggcagactat cccgccggga atggtgatta ccgacgaaaa cggcaagaaa aagcagtctt   1380

acttccatga tttctttaac tatgccggaa tccatcgcag cgtaatgctc tacaccacgc   1440

cgaacacctg ggtggacgat atcaccgtgg tgacgcatgt cgcgcaagac tgtaaccacg   1500

cgtctgttcc atggtcaagc agaaccacgg cttagtgtca agcagaacca cggctagtga   1560

tggacaattg ttgccgggaa cgacgtgaat ctgacgtgct acaccgatgc tcactacgca   1620

atgaccctga tgaccgaaag agtgttaggc agttcgtcac gttcgtcaat ggcaatgtgg   1680

tttcgtacgg atcaagaaag caagagatca acgcacagag cacaacggaa gcagagtata   1740

ttgctatgaa tgaaggtacc agagatctac agtggctacg tggactctgt gacgaactat   1800

gctgggagtt tgcgactccg gagatacacg gcgaaaacat gtcgtgcatg tatctaactg   1860

ccaagcctgg caagcacagc aagagcaagc atattatgaa caagttccac ttggtgcgcc   1920

acctagtgga ggacgaggca acggcttcgc catgttggta ccgacgacat gatcgccgac   1980

gcgatgacga agccgttgcc gaagacaagt tcgagcattg tgaagatggt atgaaggtgc   2040

tgcgcatcga ccgtgagcca ggctcatctc gtttcagtgg gagcctctct gaatcaggca   2100

caatcggtgt gtctgcggtt aatcggatcg taggcgagcc gtgacgacac ggcaacgact   2160

ggagtgccat ctactgcgag cgaagaattt catgcggccg c                       2201
```

<210> SEQ ID NO 6
<211> LENGTH: 2031
<212> TYPE: DNA
<213> ORGANISM: Artificial
<220> FEATURE:
<223> OTHER INFORMATION: pVZA200 Silencing construct

<400> SEQUENCE: 6

```
gggcccacaa gagcgaagat gcagagtacg acaacacata cattccaagg ttctttgacg     60

ctaggagaaa atggagacat tgtagtacga tcggaagagt ccgtgaccaa ggaaactgtg    120

gatcttgttg ggctgtggcc actagctcgg ctttcgctga ccgtttgtgt gtagcaacaa    180

atgcagactt caacgaatta ttatccgccg aagaaatcac tttctgctgt catacatgtg    240

gcttcggatg caacggtggt tacccgatta aagcatggaa acgttttagt aaaaaaggtt    300

tagtcaccgg aggagactac aaatctggag agggttgtga accatacaga gttccacctt    360

gtcctaatga cgaccaagga aataatacat gcgccggtaa accaatggaa tcaaaccaca    420

ggtgtaccag gatgtgctac ggtgaccagg acctcgactt cgacgaagac cacagataca    480

cacgtgatta ctactaccta acatacggta gcatccaaaa ggacgtcatg acttacggac    540

caattgaagc atcgttcgat gtatacgacg atttccccag ttacaagtca ggcgtttacg    600

tgaaatgtag atctgagggt aaatttctag tttttctcct tcattttctt ggttaggacc    660

cttttctctt tttatttttt tgagctttga tctttcttta aactgatcta ttttttaatt    720

gattggttat ggtgtaaata ttacatagct ttaactgata atctgattac tttatttcgt    780

gtgtctatga tgatgatgat agttacagaa ccgacgactc gtccgtcctg tagaaacccc    840

aacccgtgaa atcaaaaaac tcgacggcct gtgggcattc agtctggatc gcgaaaactg    900

tggaattgat cagcgttggt gggaaagcgc gttacaagaa agccgggcaa ttgctgtgcc    960
```

```
aggcagtttt aacgatcagt tcgccgatgc agatattcgt aattatgcgg gcaacgtctg   1020
gtatcagcgc gaagtcttta taccgaaagg ttgggcaggc cagcgtatcg tgctgcgttt   1080
cgatgcggtc actcattacg gcaaagtgtg ggtcaataat caggaagtga tggagcatca   1140
gggcggctat acgccatttg aagccgatgt cacgccgtat gttattgccg ggaaaagtgt   1200
acgtatcacc gtttgtgtga acaacgaact gaactggcag actatcccgc cgggaatggt   1260
gattaccgac gaaaacggca agaaaaagca gtcttacttc catgatttct ttaactatgc   1320
cggaatccat cgcagcgtaa tgctctacac cacgccgaac acctgggtgg acctcgagac   1380
cgtggtgacg catgtcgcgc aagactgtaa ccacgcgtct gttatttcac gtaaacgcct   1440
gacttgtaac tggggaaatc gtcgtataca tcgaacgatg cttcaattgg tccgtaagtc   1500
atgacgtcct tttggatgct accgtatgtt aggtagtagt aatcacgtgt gtatctgtgg   1560
tcttcgtcga agtcgaggtc ctggtcaccg tagcacatcc tggtacacct gtggtttgat   1620
tccattggtt taccggcgca tgtattattt ccttggtcgt cattaggaca aggtggaact   1680
ctgtatggtt cacaaccctc tccagatttg tagtctcctc cggtgactaa accttttttta  1740
ctaaaacgtt tccatgcttt aatcgggtaa ccaccgttgc atccgaagcc acatgtatga   1800
cagcagaaag tgatttcttc ggcggataat aattcgttga agtctgcatt tgttgctaca   1860
cacaaacggt cagcgaaagc cgagctagtg gccacagccc aacaagatcc acagtttcct   1920
tggtcacgga ctcttccgat cgtactacaa tgtctccatt ttctcctagc gtcaaagaac   1980
cttggaatgt atgtgttgtc gtactctgca tcttcgctct tgtgcggccg c            2031
```

<210> SEQ ID NO 7
<211> LENGTH: 3159
<212> TYPE: DNA
<213> ORGANISM: Artificial
<220> FEATURE:
<223> OTHER INFORMATION: pVZA300 Silencing construct

<400> SEQUENCE: 7

```
gggcccgccc tcgtcggctc cacttccgcc accacgtgca ccacctcgca gcagaccgta     60
gcgtacgtgg cgctcgtaag catcctctcg gacacgtcgt ttaatcagtg ctcgacggac    120
tccggctact cgatgctgac ggccacctcg ctgcccacga cggagcagta caagctcatg    180
tgcgcgtcga cggcgtgcaa gacgatgatc aacaagatcg tgtcgctcaa cgctcccgac    240
tgcgagctga cggtgccaac tagtggcctg gtactcaacg tgttcacagc cctcgtcggc    300
tccacttccg ccaccacgtg caccacctcg cagcagaccg tagcgtacgt ggcgctcgta    360
agcatcctct cggacacgtc gtttaatcag tgctcgacgg actccggcta ctcgatgctg    420
acggccacct cgctgcccac gacggagcag tacaagctca tgtgcgcgtc gacggcgtgc    480
aagacgatga tcaacaagat cgtgtcgctc aacgctcccg actgcgagct gacggtgcca    540
actagtggcc tggtactcaa cgtgttcaca acaagagcga agatgcagag tacgacaaca    600
catacattcc aaggttcttt gacgctagga gaaaatggag acattgtagt acgatcggaa    660
gagtccgtga ccaaggaaac tgtggatctt gttgggctgt ggccactagc tcggctttcg    720
ctgaccgttt gtgtgtagca acaaatgcag acttcaacga attattatcc gccgaagaaa    780
tcactttctg ctgtcataca tgtggcttcg gatgcaacgg tggttacccg attaaagcat    840
ggaaacgttt tagtaaaaaa ggtttagtca ccggaggaga ctacaaatct ggagagggtt    900
gtgaaccata cagagttcca ccttgtccta atgacgacca aggaaataat acatgcgccg    960
gtaaaccaat ggaatcaaac cacaggtgta ccaggatgtg ctacggtgac caggacctcg   1020
```

-continued acttcgacga agaccacaga tacacacgtg attactacta cctaacatac ggtagcatcc 1080
aaaaggacgt catgacttac ggaccaattg aagcatcgtt cgatgtatac gacgatttcc 1140
ccagttacaa gtcaggcgtt tacgtgaaat gtagatctga gggtaaattt ctagtttttc 1200
tccttcattt tcttggttag gaccctttc tctttttatt tttttgagct ttgatctttc 1260
tttaaactga tctatttttt aattgattgg ttatggtgta aatattacat agctttaact 1320
gataatctga ttactttatt tcgtgtgtct atgatgatga tgatagttac agaaccgacg 1380
actcgtccgt cctgtagaaa ccccaacccg tgaaatcaaa aaactcgacg gcctgtgggc 1440
attcagtctg gatcgcgaaa actgtggaat tgatcagcgt tggtgggaaa gcgcgttaca 1500
agaaagccgg gcaattgctg tgccaggcag ttttaacgat cagttcgccg atgcagatat 1560
tcgtaattat gcgggcaacg tctggtatca gcgcgaagtc tttataccga aaggttgggc 1620
aggccagcgt atcgtgctgc gtttcgatgc ggtcactcat tacggcaaag tgtgggtcaa 1680
taatcaggaa gtgatggagc atcagggcgg ctatacgcca tttgaagccg atgtcacgcc 1740
gtatgttatt gccgggaaaa gtgtacgtat caccgtttgt gtgaacaacg aactgaactg 1800
gcagactatc ccgccgggaa tggtgattac cgacgaaaac ggcaagaaaa agcagtctta 1860
cttccatgat ttctttaact atgccggaat ccatcgcagc gtaatgctct acaccacgcc 1920
gaacacctgg gtggacctcg agaccgtggt gacgcatgtc gcgcaagact gtaaccacgc 1980
gtctgttatt tcacgtaaac gcctgacttg taactgggga aatcgtcgta tacatcgaac 2040
gatgcttcaa ttggtccgta agtcatgacg tccttttgga tgctaccgta tgttaggtag 2100
tagtaatcac gtgtgtatct gtggtcttcg tcgaagtcga ggtcctggtc accgtagcac 2160
atcctggtac acctgtggtt tgattccatt ggtttaccgg cgcatgtatt atttccttgg 2220
tcgtcattag gacaaggtgg aactctgtat ggttcacaac cctctccaga tttgtagtct 2280
cctccggtga ctaaaccttt tttactaaaa cgtttccatg ctttaatcgg gtaaccaccg 2340
ttgcatccga agccacatgt atgacagcag aaagtgattt cttcggcgga taataattcg 2400
ttgaagtctg catttgttgc tacacacaaa cggtcagcga aagccgagct agtggccaca 2460
gcccaacaag atccacagtt tccttggtca cggactcttc cgatcgtact acaatgtctc 2520
cattttctcc tagcgtcaaa gaaccttgga atgtatgtgt tgtcgtactc tgcatcttcg 2580
ctcttgttgt gaacacgttg agtaccaggc cactagttgg caccgtcagc tcgcagtcgg 2640
gagcgttgag cgacacgatc ttgttgatca tcgtcttgca cgccgtcgac gcgcacatga 2700
gcttgtactg ctccgtcgtg ggcagcgagg tggccgtcag catcgagtag ccggagtccg 2760
tcgagcactg attaaacgac gtgtccgaga ggatgcttac gagcgccacg tacgctacgg 2820
tctgctgcga ggtggtgcac gtggtggcgg aagtggagcc gacgagggct gtgaacacgt 2880
tgagtaccag gccactagtt ggcaccgtca gctcgcagtc gggagcgttg agcgacacga 2940
tcttgttgat catcgtcttg cacgccgtcg acgcgcacat gagcttgtac tgctccgtcg 3000
tgggcagcga ggtggccgtc agcatcgagt agccggagtc cgtcgagcac tgattaaacg 3060
acgtgtccga gaggatgctt acgagcgcca cgtacgctac ggtctgctgc gaggtggtgc 3120
acgtggtggc ggaagtggag ccgacgaggg cgcggccgc 3159

<210> SEQ ID NO 8
<211> LENGTH: 2031
<212> TYPE: DNA
<213> ORGANISM: Artificial
<220> FEATURE:
<223> OTHER INFORMATION: pVZA400 silencing construct -continued

<400> SEQUENCE: 8

```
gggcccttc cgtaggtgaa cctgcggaag gatcattacc acacctaaaa actttccacg     60
tgaaccgttt caacccaata gttgggggtc ttacttggcg gcggctgctg gctttattgc    120
tggcggctac tgctgggcga gccctatcaa aaggcgagcg tttggacttc ggtctgagct    180
agtagctttt ttattttaaa ccctttactt aatactgatt atactgtggg gacgaaagtc    240
tctgctttta actagatagc aactttcagc agtggatgtc taggctcgca catcgatgaa    300
gaacgctgcg aactgcgata cgtaatgcga attgcaggat tcagtgagtc atcgaaattt    360
tgaacgcata ttgcacttcc gggttagtcc tggaagtatg cctgtatcag tgtccgtaca    420
acaaacttgg ctttcttcct tccgtgtagt cggtggagga gatgccagat gtgaagtgtc    480
ttgcggttgg ttttcggacc gactgcgagt ccttttaaat gtactaaact gtacttctct    540
ttgctccaaa agtggtggca ttgctggttg tggacgctgc tattgtagcg agttggcgac    600
cggtttgtag atctgagggt aaatttctag tttttctcct tcattttctt ggttaggacc    660
cttttctctt tttatttttt tgagctttga tctttcttta aactgatcta ttttttaatt    720
gattggttat ggtgtaaata ttacatagct ttaactgata atctgattac tttatttcgt    780
gtgtctatga tgatgatgat agttacagaa ccgacgactc gtccgtcctg tagaaacccc    840
aacccgtgaa atcaaaaaac tcgacggcct gtgggcattc agtctggatc gcgaaaactg    900
tggaattgat cagcgttggt gggaaagcgc gttacaagaa agccgggcaa ttgctgtgcc    960
aggcagtttt aacgatcagt tcgccgatgc agatattcgt aattatgcgg gcaacgtctg   1020
gtatcagcgc gaagtcttta taccgaaagg ttgggcaggc cagcgtatcg tgctgcgttt   1080
cgatgcggtc actcattacg gcaaagtgtg ggtcaataat caggaagtga tggagcatca   1140
gggcggctat acgccatttg aagccgatgt cacgccgtat gttattgccg ggaaaagtgt   1200
acgtatcacc gtttgtgtga acaacgaact gaactggcag actatcccgc cgggaatggt   1260
gattaccgac gaaaacggca agaaaaagca gtcttacttc catgatttct ttaactatgc   1320
cggaatccat cgcagcgtaa tgctctacac cacgccgaac acctgggtgg acctcgagac   1380
cgtggtgacg catgtcgcgc aagactgtaa ccacgcgtct gttaaaccgg tcgccaactc   1440
gctacaatag cagcgtccac aaccagcaat gccaccactt ttggagcaaa gagaagtaca   1500
gtttagtaca tttaaaagga ctcgcagtcg gtccgaaaac caaccgcaag acacttcaca   1560
tctggcatct cctccaccga ctacacggaa ggaagaaagc caagtttgtt gtacggacac   1620
tgatacaggc atacttccag gactaacccg gaagtgcaat atgcgttcaa aatttcgatg   1680
actcactgaa tcctgcaatt cgcattacgt atcgcagttc gcagcgttct tcatcgatgt   1740
gcgagcctag acatccactg ctgaaagttg ctatctagtt aaaagcagag actttcgtcc   1800
ccacagtata atcagtatta agtaaagggt ttaaaataaa aaagctacta gctcagaccg   1860
aagtccaaac gctcgccttt tgatagggct cgcccagcag tagccgccag caataaagcc   1920
agcagccgcc gccaagtaag acccccaact attgggttga aacggttcac gtggaaagtt   1980
tttaggtgtg gtaatgatcc ttccgcaggt tcacctacgg aaagcggccg c             2031
```

<210> SEQ ID NO 9
<211> LENGTH: 26
<212> TYPE: DNA
<213> ORGANISM: Artificial
<220> FEATURE:
<223> OTHER INFORMATION: Primer GUS forward

<400> SEQUENCE: 9
ggtgggaaag cgcgttacaa gaaagc 26

<210> SEQ ID NO 10
<211> LENGTH: 25
<212> TYPE: DNA
<213> ORGANISM: Artificial
<220> FEATURE:
<223> OTHER INFORMATION: Primer GUS reverse

<400> SEQUENCE: 10
gtttacgcgt tgcttccgcc actgg 25

<210> SEQ ID NO 11
<211> LENGTH: 25
<212> TYPE: DNA
<213> ORGANISM: Artificial
<220> FEATURE:
<223> OTHER INFORMATION: Hygromycin PT FP

<400> SEQUENCE: 11
cgtctgtcga gaagtttctg atcga 25

<210> SEQ ID NO 12
<211> LENGTH: 26
<212> TYPE: DNA
<213> ORGANISM: Artificial
<220> FEATURE:
<223> OTHER INFORMATION: Hygromycin PT RP

<400> SEQUENCE: 12
tacttctaca cagccatcgg tccaga 26

<210> SEQ ID NO 13
<211> LENGTH: 440
<212> TYPE: DNA
<213> ORGANISM: Artificial
<220> FEATURE:
<223> OTHER INFORMATION: Cutinase, Phytophthora nicotianae (VZA 1 65R = Pnic Ri)

<400> SEQUENCE: 13
tcataccatc tcgacaatgc ctcgaacttg tccttcggca acggcttcgt catcgcgtcg 60
gcgatcatgt cgtcggtacc aacatggcga atccgtagct gctcgtcctc cactaggtgg 120
cgcaccaagt ggaacttgtt cataatgtgc ttgctcttgc tgtgcttgcc aggcttggca 180
gtcaggtaga tgcacgacat gttatcaccg aatatctccg gagtcgcaaa ctcccagcat 240
agttcgtcac agagtccacg tagccactgt agatctctgg taccttcatt catagcaata 300
tactctgctt ccgtcgtgct ctgtgcgttg atctcttgct ttcttgatcc gtacgaaacc 360
acgttaccat tgacgaacgt cacgaaccca ctaacactct ttcggtcatc agggtcatta 420
gcgtagtcag catcggtgta 440

<210> SEQ ID NO 14
<211> LENGTH: 452
<212> TYPE: DNA
<213> ORGANISM: Artificial
<220> FEATURE:
<223> OTHER INFORMATION: Cutinase, Phytophthora nicotianae (VZA 2 69F = Pnic 21)

<400> SEQUENCE: 14
accatctcga caatgcctcg aacttgtcct tcggcaacgg cttcgtcatc gcgtcggcga 60
tcatgtcgtc ggtaccaaca tggcgaatcc gtagctgctc gtcctccact aggtggcgca 120
ccaagtggaa cttgttcata atatgcttgc tcttgctgtg cttgccaggc ttggcagtta 180
gatagatgca cgacatgtta tcgccgagta tctccggagt cgcaaactcc cagcatagtt 240
cgtcacagag tccacgtagc cactgtagat ctctggtacc ttcattcata gcaatatact 300
ctgcttccgt tgtgctctgt gcgttgatct cttgctttct tgatccgtac gaaaccacat 360
tgccattgac gaacgtcacg aacccgctaa cactctttcg gtcatcaggg tcattagcgt 420
agtcagcatc ggtgtagcac gtcagattca cg 452

<210> SEQ ID NO 15
<211> LENGTH: 388
<212> TYPE: DNA
<213> ORGANISM: Artificial
<220> FEATURE:
<223> OTHER INFORMATION: Cutinase, Phytophthora nicotianae (VZA 3 73F = Pnic 23)

<400> SEQUENCE: 15
tcataccatc tcgacaatgc tcaaacttgt ccttcggcaa cggcttcatc atcgcgtcgg 60
ctatcatgtc gtcggtgcca acatggcgaa tccgtagctg ctcgtcctcc actaggtggc 120
gcaccaagtg aaacttgttc ataatgtgct tgctcttgct gtgcttgcca ggcttggcag 180
tcaggtagat gcacgacttg ttatcgccga gtatctccgg agtcgcaaac tcccagcata 240
gttcttcaca gagtccacgt agccactgta gatatctggt accttcattc atagcaatat 300
actctgcttc cgttgtactc tgtacgttga tctcttgctt ccttgatccg tacgaaacca 360
cattgccatt gacgaacgtc acgaaccc 388

<210> SEQ ID NO 16
<211> LENGTH: 467
<212> TYPE: DNA
<213> ORGANISM: Artificial
<220> FEATURE:
<223> OTHER INFORMATION: Cutinase, Phytophthora nicotianae (VZA 3 73F = Pnic 23)

<400> SEQUENCE: 16
tcataccatc acgacaatgc ctcgaacttg tccttcggca acggcttcgt catcgcgtcg 60
gcgatcatgt cgtcggtacc aacatggcga atccgtagct gctcgtcctc cactaggtgg 120
cgcaccaagt ggaacttgtt cataatatgc ttgctcttgc tgtgcttgcc aggcttggca 180
gttagataga tgcacgacat gttatcgccg agtatctccg gagtcgcaaa ctcccagcat 240
agttcgtcac agagtccacg tagccactgt agatctctgg taccttcatt catagcaata 300
tactctgctt ccgttgtgct ctgtgcgttg atctcttgct ttcttgatcc gtacgaaacc 360
acattgccat tgacgaacgt cacgaacccg ctaacactct ttcggtcatc agggtcatta 420
gcgtagtcag catcggtgta gcacgtcaga ttcacgtcgt tcccggg 467

<210> SEQ ID NO 17
<211> LENGTH: 465
<212> TYPE: DNA
<213> ORGANISM: Artificial
<220> FEATURE:
<223> OTHER INFORMATION: Cutinase, Phytophthora nicotianae (VZA 1 65R = Pnic Ri)

<400> SEQUENCE: 17
tcataccatc tcgacaatgc ctcgaacttg tccttcggca acggcttcgt catcgcgtcg 60
gcgatcatgt cgtcggtacc aacatggcga atccgtagct gctcgtcctc cactaggtgg 120

-continued cgcaccaagt ggaacttgtt cataatatgc ttgctcttgc tgtgcttgcc aggcttggca 180
gttagataga tgcacgacat gttatcgccg agtatctccg gagtcgcaaa ctcccagcat 240
agttcgtcac agagtccacg tagccactgt agatctctgg taccttcatt catagcaata 300
tactctgctt ccgttgtgct ctgtgcgttg atctcttgct ttcttgatcc gtacgaaacc 360
acattgccat tgacgaacgt cacgaacccg ctaacactct ttcggtcatc agggtcatta 420
gcgtagtcag catcggtgta gcacgtcaga ttcacgtcgt tcccg 465

<210> SEQ ID NO 18
<211> LENGTH: 395
<212> TYPE: DNA
<213> ORGANISM: Artificial
<220> FEATURE:
<223> OTHER INFORMATION: Cutinase, Phytophthora capsici (VZA 6 70F = Pcap 30)

<400> SEQUENCE: 18
ccatctcgac aatgcctcga acttgtcctt cggcaacggc ttcgtcatcg cgtcggcgat 60
catgtcgtcg gtaccaacat ggctaatccg tagctgctcg tcctccacta ggtggcgcac 120
caagtggaac ttgttcataa tatgcttgct cttgctgtgc ttgccaggct tggcagttag 180
atagatgcac gacatgttat cgccgagtat ctccggagtc gcaaactccc agcatagttc 240
gtcacagagt ccacgtagcc actgtagatc tctggtacct tcattcatag caatatactc 300
tgcttccgtt gtgctctgtg cgttgatctc ttgctttctt gatccgtacg aaaccacatt 360
gccattgacg aacgtcacga acccgctaac actct 395

<210> SEQ ID NO 19
<211> LENGTH: 395
<212> TYPE: DNA
<213> ORGANISM: Artificial
<220> FEATURE:
<223> OTHER INFORMATION: Cutinase, Phytophthora capsici (VZA 7 72F = Pcap 31)

<400> SEQUENCE: 19
ctataacgac aatgcctcga actgggcctt cggcaacggc ttcgtcatcg cgtcggcgat 60
catgtcgtcg gtaccaacat ggcgaatccg tagctgctcg tcctccacta ggtggcgcac 120
caagtggaac ttgttcataa tatgcttgct cttgctgtgc ttgccaggct tggcagttag 180
atagatgcac gacatgttat cgccgagtat ctccggagtc gcaaactccc agcatagttc 240
gtcacagagt ccacgtagcc actgtagatc tctggtacct tcattcatag caatatactc 300
tgcttccgtt gtgctctgtg cgttgatctc ctgctttctt gatccgtacg aaaccacatt 360
gccattgacg aacgtcacga acccgctaac actct 395

<210> SEQ ID NO 20
<211> LENGTH: 395
<212> TYPE: DNA
<213> ORGANISM: Artificial
<220> FEATURE:
<223> OTHER INFORMATION: Cutinase, Phytophthora capsici (VZA 8 79F = Pcap 28)

<400> SEQUENCE: 20
ctataacgac aatgcctcga actgggcctt cggcaacggc ttcgtcatcg cgtcggcgat 60
catgtcgtcg gtaccaacat ggcgaatccg tagctgctcg tcctccacta ggtggcgcac 120
caagtggaac ttgttcataa tatgcttgct cttgctgtgc ttgccaggct tggcagttag 180
atagatgcac gacatgttat cgccgagtat ctccggagtc gcaaactccc agcatagttc 240

```
gtcacagagt ccacgtagcc actgtagatc tctggtacct tcattcatag caatatactc    300

tgcttccgtt gtgctctgtg cgttgatctc ctgctttctt gatccgtacg aaaccacatt    360

gccattgacg aacgtcacga acccgctaac actct                               395


<210> SEQ ID NO 21
<211> LENGTH: 461
<212> TYPE: DNA
<213> ORGANISM: Artificial
<220> FEATURE:
<223> OTHER INFORMATION: Cutinase, Phytophthora capsici (VZA 9 84F =
      Pcap 01)

<400> SEQUENCE: 21

taataccact cgacaatgca tcgaacttga ccttcggcaa cggcttcgtc atcgcgtcgg     60

catcatgtcg tcggtaccaa catgccgaat ccgtagctgc tcgtcctcca ctaggtggcg    120

caccaagtgg aacttgttca taatatgctt gctcttgctg tgcttgccag gcttggcaat    180

tagatagatg cacgacatgt tatcgccgag tatctccgga gtcgcaaact cccagcatag    240

ttcgtcacag agtccacata gccactgtag atctctggta ccttcattca tagcaatata    300

ctctgcttcc gttgcgctct gtgcgttgaa cccttgcttt cttgatcctc actaaaccac    360

attgccattg acgaacgtca ctaaccctct aacactcttt agatcattaa tatcattagc    420

ctaatcaaca aactcctaat acctcagatt cactacaatc c                        461


<210> SEQ ID NO 22
<211> LENGTH: 467
<212> TYPE: DNA
<213> ORGANISM: Artificial
<220> FEATURE:
<223> OTHER INFORMATION: Cutinase, Phytophthora capsici (VZA 10 87F =
      Pcap 32)

<400> SEQUENCE: 22

tcataccatc tcgacaatgc ctcgaacttg tccttcggca acggcttcgt catcgcgtcg     60

gcgatcatgt cgtcggtacc aacatggcga atccgtagct gctcgtcctc cactaggtgg    120

cgcaccaagt ggaacttgtt cataatatgc ttgctcttgc tgtgcttgcc aggcttggca    180

gttagataga tgcacgacat gttatcgccg agtatctccg gagtcgcaaa ctcccagcat    240

agttcgtcac agagtccacg tagccactgt agatctctgg taccttcatt catagcaata    300

tactctgctt ccgttgtgct ctgtgcgttg atctcttgct ttcttgatcc gtacgaaacc    360

acattgccat tgacgaacgt cacgaacccg ctaacactct ttcggtcatc agggtcatta    420

gcgtagtcag catcggtgta gcacgtcaga ttcacgtcgt tcccggc                 467


<210> SEQ ID NO 23
<211> LENGTH: 416
<212> TYPE: DNA
<213> ORGANISM: Artificial
<220> FEATURE:
<223> OTHER INFORMATION: Cutinase, Phytophthora capsici (VZA 11 89F =
      Pcap 03)

<400> SEQUENCE: 23

tcataccatc tcgacaatgc ctcgaacttg tccttcggca acggcttcgt catcgcgtcg     60

gcgatcatgt cgtcggtacc aacatggcga atccgtagct gctcgtcctc cactaggtgg    120

cgcaccaagt ggaacttgtt cataatatgc ttgctcttgc tgtgcttgcc aggcttggca    180

gttagataga tgcacgacat gttatcgccg agtatctccg gagtcgcaaa ctcccagcat    240
```

agttcgtcac agagtccacg tagccactgt agatctctgg taccttcatt catagcaata 300
tactctgctt ccgttgtgct ctgtgcgttg atctcttgct ttcttgatcc gtacgaaacc 360
acattgccat tgacgaacgt cacgaacccg ctaacactct tcagattcac gtcgtt 416

<210> SEQ ID NO 24
<211> LENGTH: 466
<212> TYPE: DNA
<213> ORGANISM: Artificial
<220> FEATURE:
<223> OTHER INFORMATION: Cutinase, Phytophthora capsici (VZA 12 90F = Pcap 22)

<400> SEQUENCE: 24
tcataccatc tcgacaatgc ctcgaacttg tccttcggca acggcttcgt catcgcgtcg 60
gcgatcatgt cgtcggtacc aacatggcga atccgtagct gctcgtcctc cactaggtgg 120
cgcaccaagt ggaacttgtt cataatatgc ttgctcttgc tgtgcttgcc aggcttggca 180
gttagataga tgcacgacat gttatcgccg agtatctccg gagtcgcaaa ctcccagcat 240
agttcgtcac agagtccacg tagccactgt agatctctgg taccttcatt catagcaata 300
tactctgctt ccgttgtgct ctgtgcgttg atctcttgct ttcttgatcc gtacgaaacc 360
acattgccat tgacgaacgt cacgaacccg ctaacactct ttcggtcatc agggtcatta 420
gcgtagtcag catcggtgta gcacgtcaga ttcacgtcgt tcccgg 466

<210> SEQ ID NO 25
<211> LENGTH: 467
<212> TYPE: DNA
<213> ORGANISM: Artificial
<220> FEATURE:
<223> OTHER INFORMATION: Cutinase, Phytophthora capsici (VZA 13 91F = Pcap 25)

<400> SEQUENCE: 25
tcaaaccatc tcgacaatgc ctcgaacttg tccttcggca acggcttcgt catcgcgtcg 60
gcgatcatgt cgtcggtacc aacatggcaa atccgtagct gctcgtcctc cactaggtgg 120
cgcaccaagt ggaacttgtt cataatatgc ttgctcttgc tgtgcttgcc aggcttggca 180
gttagataga tgcacgacat gttatcgccg agtatctccg gagtcgcaaa ctcccagcat 240
agttcgtcac agagtccacg tagccactgt agatctctgg taccttcatt catagcaata 300
tactctgctt ccgttgtgct ctgtgcgttg atctcttgct ttcttgatcc gtacgaaacc 360
acattgccat tgacgaacgt cacgaacccg ctaacactct ttcggtcatc agggtcatta 420
gcgtagtcag catcggtgta gcacgtcaga ttcacgtcgt tcccggg 467

<210> SEQ ID NO 26
<211> LENGTH: 466
<212> TYPE: DNA
<213> ORGANISM: Artificial
<220> FEATURE:
<223> OTHER INFORMATION: Cutinase, Phytophthora palmivora (VZA 14 81F = Ppal 02)

<400> SEQUENCE: 26
tcataccatc tcgacaatgc ctcgaacttg tccttcggca acggcttcgt catcgcgtcg 60
gcgatcatgt cgtcggtacc aacatggcga atccgtagct gctcgtcctc cactaggtgg 120
cgcaccaagt ggaacttgtt cataatatgc ttgctcttgc tgtgcttgcc aggcttggca 180
gttagataga tgcacgacat gttatcgccg agtatctccg gagtcgcaaa ctcccagcat 240
agttcgtcac agagtccacg tagccactgt agatctctgg taccttcatt catagcaata 300
tactctgctt ccgttgtgct ctgtgcgttg atctcttgct ttcttgatcc gtacgaaacc 360
acattgccat tgacgaacgt cacgaacccg ctaacactct ttcggtcatc agggtcatta 420
gcgtagtcag catcggtgta gcacgtcaga ttcacgtcgt tcccgg 466

<210> SEQ ID NO 27
<211> LENGTH: 465
<212> TYPE: DNA
<213> ORGANISM: Artificial
<220> FEATURE:
<223> OTHER INFORMATION: Cutinase, Phytophthora palmivora (VZA 15 82F = Ppal 10)

<400> SEQUENCE: 27
tcataccatc tcgacaatgc ctcgaacttg tccttcggca acggcttcgt catcgcgtcg 60
gcgatcatgt cgtcggtacc aacatggcga atccgtagct gctcgtcctc cactaggtgg 120
cgcaccaagt ggaacttgtt cataatatgc ttgctcttgc tgtgcttgcc aggcttggca 180
gttagataga tgcacgacat gttatcgccg agtatctccg gagtcgcaaa ctcccagcat 240
agttcgtcac agagtccacg tagccactgt agatctctgg taccttcatt catagcaata 300
tactctgctt ccgttgtgct ctgtgcgttg atctcttgct ttcttgatcc gtacgaaacc 360
acattgccat tgacgaacgt cacgaacccg ctaacactct ttcggtcatc agggtcatta 420
gcgtagtcag catcggtgta gcacgtcaga ttcacgtcgt tcccg 465

<210> SEQ ID NO 28
<211> LENGTH: 467
<212> TYPE: DNA
<213> ORGANISM: Artificial
<220> FEATURE:
<223> OTHER INFORMATION: Cutinase, Phytophthora palmivora (VZA 16 83F = Ppal 11)

<400> SEQUENCE: 28
tcataccatc tcgacaatgc ctcgaacttg tccttcggca acggcttcgt catcgcgtcg 60
gcgatcatgt cgtcggtacc aacatggcga atccgtagct gctcgtcctc cactaggtgg 120
cgcaccaagt ggaacttgtt cataatatgc ttgctcttgc tgtgcttgcc aggcttggca 180
gttagataga tgcacgacat gttatcgccg agtatctccg gagtcgcaaa ctcccagcat 240
agttcgtcac agagtccacg tagccactgt agatctctgg taccttcatt catagcaata 300
tactctgctt ccgttgtgct ctgtgcgttg atctcttgct ttcttgatcc gtacgaaacc 360
acattgccat tgacgaacgt cacgaacccg ctaacactct ttcggtcatc agggtcatta 420
gcgtagtcag catcggtgta gcacgtcaga ttcacgtcgt tcccggc 467

<210> SEQ ID NO 29
<211> LENGTH: 466
<212> TYPE: DNA
<213> ORGANISM: Artificial
<220> FEATURE:
<223> OTHER INFORMATION: Cutinase, Phytophthora palmivora (VZA17 85F = Ppal 04)

<400> SEQUENCE: 29
tcataccatc tcgacaatgc ctcgaacttg tccttcggca acggcttcgt catcgcgtcg 60
gcgatcatgt cgtcggtacc aacatggcga atccgtagct gctcgtcctc cactaggtgg 120
cgcaccaagt ggaacttgtt cataatatgc ttgctcttgc tgtgcttgcc aggcttggca 180
gttagataga tgcacgacat gttatcgccg agtatctccg gagtcgcaaa ctcccagcat 240

```
agttcgtcac agagtccacg tagccactgt agatctctgg taccttcatt catagcaata    300

tactctgctt ccgttgtgct ctgtgcgttg atctcttgct ttcttgatcc gtacgaaacc    360

acattgccat tgacgaacgt cacgaacccg ctaacactct ttcggtcatc agggtcatta    420

gcgtagtcag catcggtgta gcacgtcaga ttcacgtcgt tcccgg                   466


<210> SEQ ID NO 30
<211> LENGTH: 467
<212> TYPE: DNA
<213> ORGANISM: Artificial
<220> FEATURE:
<223> OTHER INFORMATION: Cutinase, Phytophthora palmivora (VZA 18 86F =
      Ppal 05)

<400> SEQUENCE: 30

tcataccatc tcgacaatgc ctcgaacttg tccttcggca acggcttcgt catcgcgtcg     60

gcgatcatgt cgtcggtacc aacatggcga atccgtagct gctcgtcctc cactaggtgg    120

cgcaccaagt ggaacttgtt cataatatgc ttgctcttgc tgtgcttgcc aggcttggca    180

gttagataga tgcacgacat gttatcgccg agtatctccg gagtcgcaaa ctcccagcat    240

agttcgtcac agagtccacg tagccactgt agatctctgg taccttcatt catagcaata    300

tactctgctt ccgttgtgct ctgtgcgttg atctcttgct ttcttgatcc gtacgaaacc    360

acattgccat tgacgaacgt cacgaacccg ctaacactct ttcggtcatc agggtcatta    420

gcgtagtcag catcggtgta gcacgtcaga ttcacgtcgt tcccggg                  467


<210> SEQ ID NO 31
<211> LENGTH: 420
<212> TYPE: DNA
<213> ORGANISM: Artificial
<220> FEATURE:
<223> OTHER INFORMATION: Cutinase, Phytophthora cinnamomi (VZA 19 64R =
      Pcin Ri)

<400> SEQUENCE: 31

tcataccatc tcgacaatgc ctcgaacttg tccttcggca acggcttcgt catcgcgtcg     60

gcgatcatgt cgtcggtacc aacatggcga agccgttgcc tcgtcctcca ctaggtggcg    120

caccaagtgg aacttgttca taatatgctt gctcttgctg tgcttgccag gcttggcagt    180

tagatagatg cacgacatgt tatcgccgag tatctccgga gtcgcaaact cccagcatag    240

ttcgtcacag agtccacgta gccactgtag atctctggta ccttcattca tagcaatata    300

ctctgcttcc gttgtgctct gtgcgttgat ctcttgcttt cttgatccgt acgattcggt    360

catcagggtc attagcgtag tcagcatcgg tgtagcacgt cagattcacg tcgttcccgg    420


<210> SEQ ID NO 32
<211> LENGTH: 459
<212> TYPE: DNA
<213> ORGANISM: Artificial
<220> FEATURE:
<223> OTHER INFORMATION: Cutinase, Phytophthora cinnamomi (VZA 20 77F =
      Pcin 01)

<400> SEQUENCE: 32

atcatctcga caatgcctcg aacttgtcct tcggcaacgg cttcgtcatc gcgtcggcga     60

tcatgtcgtc ggtaccaaca tggcgaagcc gtacctcgtc ctccactagg tggcgcacca    120

agtggaactt gttcataata tgcttgctct tgctgtgctt gccaggcttg gcagttagat    180

agatgcacga catgttatcg ccgagtatct ccggagtcgc aaactcccag catagttcgt    240

cacagagtcc acgtagccac tgtagatctc tggtaccttc attcatagca atatactctg    300
```

cttccgttgt gctctgtgcg ttgatctctt gctttcttga tccgtacgaa accacattgc 360
cattgacgaa cgtcacgaac ccgctaacac tctttcggtc atcagggtca ttagcgtagt 420
cagcatcggt gtagcacgtc agattcacgt cgttcccgg 459

<210> SEQ ID NO 33
<211> LENGTH: 442
<212> TYPE: DNA
<213> ORGANISM: Artificial
<220> FEATURE:
<223> OTHER INFORMATION: Cutinase, Phytophthora citrophthora (VXA 21 63R = Pcto Ri)

<400> SEQUENCE: 33
tcataccatc tcgacaatgc ctcgaacttg tccttcggca acggcttcgt catcgcgtcg 60
gcgatcatgt cgtcggtacc aacgtgggat cggcgttgct cgtcctccac taggtggcgc 120
accaagtgga acttgttcat aatatgcttg ctcttgctgt gcttgccagg cttggcagtt 180
agatagatgc acgacatgtt atcgccgagt atctccggag tcgcaaactc ccagcatagt 240
tcgtcacaga gtccacgtag ccactgtaga tctctggtac cttcattcat agcaatatac 300
tctgcttccg ttgtgctctg tgcgttgatc tcttgctttc ttgatccgta cgaaaccaca 360
ttgccattga cgaacgtcac gaacccgcta acactctttc ggtcatcagg gtcattagcg 420
tagtcagcat cggtgtagca cg 442

<210> SEQ ID NO 34
<211> LENGTH: 442
<212> TYPE: DNA
<213> ORGANISM: Artificial
<220> FEATURE:
<223> OTHER INFORMATION: Cutinase, Phytophthora citricola (VZA 22 66R = Pctr Ri)

<400> SEQUENCE: 34
tcataccatc tcgacaatgc ctcgaacttg tccttcggca acggcttcgt catcgcgtcg 60
gcgatcatgt cgtcggtacc aacgtgggat cggcgttgct cgtcctccac taggtggcgc 120
accaagtgga acttgttcat aatatgcttg ctcttgctgt gcttgccagg cttggcagtt 180
agatagatgc acgacatgtt atcgccgagt atctccggag tcgcaaactc ccagcatagt 240
tcgtcacaga gtccacgtag ccactgtaga tctctggtac cttcattcat agcaatatac 300
tctgcttccg ttgtgctctg tgcgttgatc tcttgctttc ttgatccgta cgaaaccaca 360
ttgccattga cgaacgtcac gaacccgcta acactctttc ggtcatcagg gtcattagcg 420
tagtcagcat cggtgtagca cg 442

<210> SEQ ID NO 35
<211> LENGTH: 469
<212> TYPE: DNA
<213> ORGANISM: Artificial
<220> FEATURE:
<223> OTHER INFORMATION: Cutinase, Phytophthora megakarya (VZA 23 80F = Pmek 01)

<400> SEQUENCE: 35
tcataccatc tcgacaatgc ctcgaacttg tccttcggca acggcttcgt catcgcgtcg 60
gcgatcatgt cgtcggtacc aacatggcga atccgtagct gctcgtcctc cactaggtgg 120
cgcaccaagt ggaacttgtt cataatatgc ttgctcttgc tgtgcttgcc aggcttggca 180
gttagataga tgcacgacat gttatcgccg agtatctccg gagtcgcaaa ctcccagcat 240

-continued agttcgtcac agagtccacg tagccactgt agatctctgg taccttcatt catagcaata 300
tactctgctt ccgttgtgct ctgtgcgttg atctcttgct ttcttgatcc gtacgaaacc 360
acattgccat tgacgaacgt cacgaacccg ctaacactct ttcggtcatc agggtcatta 420
gcgtagtcag catcggtgta gcacgtcaga ttcacgtcgt tcccggcaa 469

<210> SEQ ID NO 36
<211> LENGTH: 463
<212> TYPE: DNA
<213> ORGANISM: Artificial
<220> FEATURE:
<223> OTHER INFORMATION: Cutinase, Phytophthora megasperma/ P. sojae (VZA 24 92F = Pmeg 01)

<400> SEQUENCE: 36
cagaccatct cgacaatgcc tcgaacttgt ccttcggcaa cggcttcgtc atcgcgtcgg 60
cgatcatgtc gtcggtacca acatggctaa tcctagctgc tcatcctcca ctaggtggcg 120
caccaagtgg aacttgttca taatatgctt gctcttgctg tgcttgccag gcttggcagt 180
tagatagatg cacgacatgt tatcgccgag tatctccgga gtcgcaaact cccagcatag 240
ttcgtcacag agtccacgta gccactgtag atctctggta ccttcattca tagcaatata 300
ctctgcttcc gttgtgctct gtgcgttgat ctcttgcttt cttgatccct acgaaaccac 360
attgccattg acgaacgtca cgaacccgct aacactcttt cggtcatcaa ggtcattagc 420
gtagtcagca tcggtgtagc acgtcagatt cacgtcgttc ccg 463

<210> SEQ ID NO 37
<211> LENGTH: 460
<212> TYPE: DNA
<213> ORGANISM: Artificial
<220> FEATURE:
<223> OTHER INFORMATION: Cutinase, Phytophthora heve (VZA 25 93F = Phev 02)

<400> SEQUENCE: 37
tcataccatc tcgacaatgc ctcgaacttg tccttcggca acggcttcgt catcgcgtcg 60
gcgatcatgt cgtcggtgcc aacatgacga atccgtagct gctcgtcctc cactaggtgg 120
cgcaccaagt ggaacttgtt cataatatgc ttgctcttgc tgtgcttgcc aggcttggca 180
gttagataga tgcacgacat gttatcgccg agtatctccg gagtcgcaaa ctcccagcat 240
agttcgtcac agagtccacg tagccactgt agatctctgg taccttcatt catagcaata 300
tactctgctt ccgttgtgct ctgtgcgttg atctcttgct ttcttgatcc gtacgaaacc 360
acattgccat tgacgaacgt cacaaacccg ctaacactct ttcggtcatc agggtcatta 420
gcgtagtcag catcggtgta gcacgtcaga ttcacgtcgt 460

<210> SEQ ID NO 38
<211> LENGTH: 22
<212> TYPE: DNA
<213> ORGANISM: Artificial
<220> FEATURE:
<223> OTHER INFORMATION: M. persicae cathepsin FP

<400> SEQUENCE: 38
gggcccacaa gagcgaagat gc 22

<210> SEQ ID NO 39
<211> LENGTH: 30
<212> TYPE: DNA
<213> ORGANISM: Artificial
<220> FEATURE:

<223> OTHER INFORMATION: M. persicae cathepsin RP

<400> SEQUENCE: 39
atttcacgta aacgcctgac ttgtaactgg 30

<210> SEQ ID NO 40
<211> LENGTH: 21
<212> TYPE: DNA
<213> ORGANISM: Artificial
<220> FEATURE:
<223> OTHER INFORMATION: P. infestans elicitin FP

<400> SEQUENCE: 40
gggcccgccc tcgtcggctc c 21

<210> SEQ ID NO 41
<211> LENGTH: 22
<212> TYPE: DNA
<213> ORGANISM: Artificial
<220> FEATURE:
<223> OTHER INFORMATION: P. infestans rDNA FP

<400> SEQUENCE: 41
gggccctttc cgtaggtgaa cc 22

<210> SEQ ID NO 42
<211> LENGTH: 22
<212> TYPE: DNA
<213> ORGANISM: Artificial
<220> FEATURE:
<223> OTHER INFORMATION: P. infestans rDNA RP

<400> SEQUENCE: 42
aaaccggtcg ccaactcgct ac 22

<210> SEQ ID NO 43
<211> LENGTH: 584
<212> TYPE: DNA
<213> ORGANISM: Artificial
<220> FEATURE:
<223> OTHER INFORMATION: Phialophora gregata rDNA

<400> SEQUENCE: 43
tgcggaagga tcattactag agcaaaggat agggagcacc ccacaggagc ttgctccgtg 60
gcgggctgcc cgtcgagcct ctcgaagaag ctcggtcctg aactccaccc ttgaataaat 120
tacctttgtt gctttggcgg gccgcctcgc gccagcggct tcggctgttg cgtgcccgcc 180
agaggaccac aactcttgtt tttagtgatg tctgagtact atataatagt taaaactttc 240
aacaacggat ctcttggttc tggcatcgat gaagaacgca gcgaaatgcg ataagtaatg 300
tgaattgcag aattcagtga atcatcgaat ctttgaacgc acattgcgcc ctctggtatt 360 ccgggggca tgcctgttcg agcgtcatta taaccactca agctctcgct tggtattggg 420
gttcgcggtt ccgcggcccc taaaatcagt ggcggtgcct gtcggctcta cgcgtagtaa 480
tactcctcgc gattgagtct ggcaggtcta catgccagca acacccaaat ttttacaggt 540
tgacctcgga tcaggtaggg ataccccgct gaacttaagc atat 584

<210> SEQ ID NO 44
<211> LENGTH: 658
<212> TYPE: DNA
<213> ORGANISM: Artificial
<220> FEATURE:
<223> OTHER INFORMATION: Phialophora gregata Genotype B DNA Marker

<400> SEQUENCE: 44
ctccaccaac taagaacggc catgctggac acgaccactc cggtcatgat cactcccacg 60
accacggaaa gggcaaagct atcgatacca gtgaggacaa gaaggatgag gatgaggatg 120
atggagagga ggttgatgct actggacttg aggacaagga tattgagttg gtcatgaccc 180
aagctagcgt ctcacgaaac aaggctgtca aggcattgaa ggagaacgac aatgatatag 240
tcagctctat tatggctcta agcatataga gagttgacct gttatattcg tctggctgct 300
agactgaact tggctcgttg gaggacgttg tatggagcat gcgtaccctg catctctatc 360
tggggatatg tattctgaaa aagcacttgt ggaacttcaa gtccaaattc tcagaaattt 420
gcacacttgc tacccaatcc tcgtgtatat tgtgactacc ctatacctgt ttgttgtggc 480
ggagatgaag tacctaaaag tttgtgcatt tactctgata tttgatgttc gcgactatgt 540
aggctgccag gaactcccca atagtatgaa tcaagaaatc ggtgcaggga cgtgtaccaa 600
gttagagaac taggtagact ttgaacaatc gctgcatggc cgttcttagt tggtggag 658

<210> SEQ ID NO 45
<211> LENGTH: 1096
<212> TYPE: DNA
<213> ORGANISM: Artificial
<220> FEATURE:
<223> OTHER INFORMATION: Sclerotinia sclerotiorum RNA Pol Subunit

<400> SEQUENCE: 45
ctgttccgca gattaacaac agatgtctac aggtacctgc aacgttgcgt ggaaaacaac 60
agagagttca atttgacgct gggtgtgaaa tccacgacga tcacgaacgg tctgaaatat 120
tctttggcta caggtaactg gggtgaccag aagaaggcag caagttctac cgctggtgtt 180
tctcaagtat tgaacagata taccttcgca tcaacacttt ctcatttgcg ccgaaccaat 240
acgcctatcg gacgtgatgg aaagatcgcc aaacctagac aactgcataa tactcattgg 300
ggtctggttt gtccagcaga gacgccagaa ggtcaagctt gtggtttggt caagaattta 360
gctttgatgt gttacgttac agttggtacg ccaagtgatc caatcgttga gttcatgatt 420
caacgaaata tggaagtgct ggaggagtat gaaccgctcc gagcacccaa tgcaacaaag 480
gtcttcgtca atggtgtttg ggttggtgtc catcgagacc ctgcccattt ggttaaatgt 540
gtacaagatc ttcgtagatc acatttgatt tctcatgaag tctcacttat tcgagaaatt 600
cgagacagag agttcaagat tttcactgat gcaggacgag tgtgcagacc tctgttggtc 660
atcgacaatg atccagacag ccccaacaaa ggtaatttgg tactgaacaa ggatcacatc 720
cgccgtttgg aggatgatca atctctgcca tcgaacatgg ataaggatga gaaagtacac 780
catggttatt atggattcca aggtttgatt aatgatggtg tggttgaata tttagacgcc 840
gaggaagagg agactgttat gattaccatg acacctgaag atttggatat ttctcgacag 900
cttcaagctg gttatcaaat tcgtcctgat gacagcggtg atttgaataa gcgtgtcaag 960
gcacctatca atccaactgc gcacgtctgg actcattgtg aaattcatcc aagtatgatt 1020
ctgggtatct gtgcaagcat cattcccttc ccggatcata atcaggtaag ctttaagtcc 1080
aataatgaat ttatta 1096

<210> SEQ ID NO 46
<211> LENGTH: 883
<212> TYPE: DNA
<213> ORGANISM: Artificial
<220> FEATURE:
<223> OTHER INFORMATION: Puccinia hordei 18S ribosomal RNA gene

<400> SEQUENCE: 46
agtgaaactg cgaatggctc attaaatcag ttatagttta tttgatgata ccttactaca 60
tggataactg tggtaattct agagctaata catgctgaaa agccccaacc tttggaaggg 120
gtgtatttat tagataaaaa accaatggcc cttgggtctc cttggtgatt cataataact 180
tctcgaatcg catggccttg tgccggtgat gcttcattca aatatctgcc ctatcaactt 240
tcgatggtag gatagaggcc taccatggtg atgacgggta acggggaata agggttcgat 300
tccggagaga gggcctgaga aacggccctc aaatctaagg attgcagcag gcgcgcaaat 360
tacccaatcc tgacacaggg aggtagtgac aataaataac aatgtatggc tcttttgggt 420
cttacaattg gaatgagtac aatttaaatc tcttaacgag gatcaattgg agggcaagtc 480
tggtgccagc agccgcggta attccagctc caatagcgta tattaaaatt gttgacgtta 540
aaaagctcgt agtcgaactt cggcctctgg cagttggtcc gccttttggt gtgtactgat 600
ttgttggagg cttacctctt ggtgaacttc aatgcacttt actgggtgtt gaaaggaacc 660
aggactttta ctttgaaaaa attagagtgg ttcaaagcag cttatgcctg aatacattac 720
catggaataa taaaatagga cgtgtgattc tattttgttg gtttctagga ttaccgtaat 780
gatgaataag gtcagttggg ggcatttgta ttacatcgtc agaggtgaaa ttcttggatt 840
gatgtaagac aaactactgc gaaagcatct gccaaggatg acc 883

<210> SEQ ID NO 47
<211> LENGTH: 2040
<212> TYPE: DNA
<213> ORGANISM: Artificial
<220> FEATURE:
<223> OTHER INFORMATION: *Sclerotinia sclerotiorum* Hexose Transporter

<400> SEQUENCE: 47
ggagactgct gagtctcctg ttattaccga caagaacctc agcagcgctg aaggaactcc 60
agcagcacac acaccagccg atactcctcg tgtcgtcaga tccttaaatg gttctgcacc 120
agagcatcat gatatagtac ccgaggaagc tctcgacaac ttgcctgtca ccaaattagc 180
tattatgctt ggtgctatcg catctatcgg tggtttcatg ttcggttatg aatctggtca 240
aatttctggt ttcgtccaaa tgtccgactt cttagatcga ttcggtgaaa atggtgaact 300
ttctgctgtc cgtcaaggaa ccatcgtcgc cattctctgc gccggtactc ttgttggatg 360
ccttggatct agttacctct gcgatacaat cggtcgtcgt tacactatct ccagttctgc 420
attcttctac atcatcggtg ttatcatcga aatcacttct tctactcact gggttcaatt 480
cgctatgggg agattcactg ctggtgtgaa tgctcccttt aagtttcaat tttagtatct 540
aaactctgta ttataagttg ggtattggtg ctttgagtac tagtgttcct atgtaccaat 600
ctgagtctgt gccaaagaac attcgtggtg ctgtcgtttc cagttatcag ttgttgatta 660
ctcttggtat ctggactgct tatatgatca actacggaac tcattctgcc tataccaaca 720
gtgcacagtg gcggattcct aacggtctct ccgcactctg ggccatcatc ctcggtaccg 780
ctgtcctctt catgcccgaa tccctcgctt tgcataccgt atcggacgtg aagatgaaag 840
ctcgcaaaaa catggctctc ctcaacggtg ttgaccctta ctccccactt atcgattccg 900
agatccaaga aatcgaacaa aagctcgcag ccgaaagaga aggtggtgat cacccctggt 960
acgaaatctt tactggccct gttgttccat ttctttcatg atgaattcct tttaaccttg 1020
aacgtgatct catagagaat gttgtaccga acacttctcg gaatggttct tcaagctggt 1080
caacaattga ctggtgccaa tttcttcttc tactatggta ctaccatctt caagtctggt 1140

-continued ggtatctccg attcttatgt tacctctatc attctcggta ccgtcaatgt cgtcgctacc 1200
attggtggtc tctggattgt taagaactgc ggtcgtagga aggctctcat ggttggtgct 1260
gccgagatgt ttgtttgcat gttgatctac tctttcgtcg gacacttcaa gatccaaaga 1320
caagcccaat gctcaagccc ctgggctgtt ttgatttgtt tcacctgtat ctacattgtt 1380
ggatctgcta ctacatgggg acctttggtt tgggccattg tcggagaatt atacccagca 1440
cgttacagag cttcttgcat ggctctcgcc accgcatcga actggctctt caacttcctt 1500
atctctttct tcaccacatt tatcaccaac gatatcgatt actactatgg tcttgtcttt 1560
gccggatccc ttttcgctct cttctggatt gtatacttct tcgttatcga gaccaaggat 1620
cgctcccttg aggaaatcga caccatgtac gtcctccacg tcaacccacg aacatcctcc 1680
acttgggacc ccaagtccct cggtgccgaa ggtgtcaaag gtgttgatac cgatggaatg 1740
ttcttgacca ctggagggaa agatattaag aagagtgaga tggctggacg accaatgttg 1800
gaacatgacg agagaaggtt ccctgagacc gctggaggag ctgcttctca ggagcacaaa 1860
cctgagatta tgaatgctta agcttcgctt catttttgat gagcatggat gaaagaaaaa 1920
tgcattttac gaatgtatgt cgttactacg agcaaaaagg ggggtgaaat cagtggatga 1980
taaataaacg atggaatata taatgcatgc atataatggc gtttgggaag cagcatcgtc 2040

<210> SEQ ID NO 48
<211> LENGTH: 883
<212> TYPE: DNA
<213> ORGANISM: Artificial
<220> FEATURE:
<223> OTHER INFORMATION: Fusarium solani pisi cutinase

<400> SEQUENCE: 48
aaccacacat accttcactt catcaacatt cacttcaact tcttcgcctc ttccttttca 60
ctctttatca tcctcaccat gaaattcttc gctctcacca cacttctcgc cgccacggct 120
tcggctctgc ctacttctaa ccctgcccag gagcttgagg cgcgccagct tggtagaaca 180
actcgcgacg atctgatcaa cggcaatagc gcttcctgcc gcgatgtcat cttcatttat 240
gcccgaggtt caacagagac gggcaacttg ggaactctcg gtcctagcat tgcctccaac 300
cttgagtccg ccttcggcaa ggacggtgtc tggattcagg gcgttggcgg tgcctaccga 360
gccactcttg gagacaatgc tctccctcgc ggaacctcta gcgccgcaat cagggagatg 420
ctcggtctct tccagcaggc caacaccaag tgccctgacg cgactttgat cgccggtggc 480
tacagccagg gtgctgcact tgcagccgcc tccatcgagg acctcgactc ggccattcgt 540
gacaagatcg ccggaactgt tctgttcggc tacaccaaga acctacagaa ccgtggccga 600
atccccaact accctgccga caggaccaag gtcttctgca atacagggga tctcgtttgt 660
actggtagct tgatcgttgc tgcacctcac ttggcttatg gtcctgatgc tcgtggccct 720
gcccctgagt tcctcatcga gaaggttcgg gctgtccgtg gttctgcttg aggaggatga 780
gaattttagc aggcgggcct gttaattatt gcgaggtttc aagtttttct tttggtgaat 840
agccatgata gattggttca acactcaatg tactacaatg cct 883

<210> SEQ ID NO 49
<211> LENGTH: 595
<212> TYPE: DNA
<213> ORGANISM: Artificial
<220> FEATURE:
<223> OTHER INFORMATION: Phakopsora pachyrhizi cutinase homolog

<400> SEQUENCE: 49

-continued

```
gagattgtgc tgtgcattgc acagcacagc agcaattcca acatcccccc ttgctcacag     60

tcttcaaggc tttgagcaca gattgagaac tttaagagat ttgaggagtg gtgattttcc    120

cagaggtttg gtgaggaagt cagccaacat atcttcactc ttgacatatg ttaaggatat    180

gtgttgtttc tcaatttctt gcttgacaaa atgaagtctg atgtccatat gttttgtctt    240

gaaggttgag tgactagctt gattatttgc aagttctatt gctccttgat tgtcctcaca    300

gatcgtcgtt ggagtatgaa atggcaggtt gaagaagttg gcgatcaagg ttttgatcca    360

cataacttcc ttggtgacgt cagcaattga cttgtactct gcttctgttg ttgagagaga    420

tattgttggt tgcttttgtg acttccaaga gatgaggttg ccattccata ggaccaagaa    480

tccagatacc gaacgacgag tttgaggaca ggaggcccag tctgcatctg agtaagccaa    540

gagattgttg ccaggaggag actttgtgaa tgtgagacca taggtttttg tatgc         595
```

<210> SEQ ID NO 50
<211> LENGTH: 668
<212> TYPE: DNA
<213> ORGANISM: Artificial
<220> FEATURE:
<223> OTHER INFORMATION: Phakopsora pachyrhizi rDNA

<400> SEQUENCE: 50

```
ggaagtaaaa gtcgtaacaa ggtttccgta ggtgaacctg cggaaggatc attaataaaa     60

agctaaagag tgcactttat tgtggctcaa aactaaactt tttaataaac ccatttaatt    120

ggctcattga ttgataagat ctttgggcaa tggtagcttt gaaaaaagct gcaacccacc    180

tattaatcat aatctttttt tttttaactc aaagtcaaat agaatgtttt ataaatttaa    240

atatatatat ataactttta acaatggatc tctaggctct catatcgatg aagaacacag    300

tgaaatgtga taattaatgt gaattgcaga attcagtgaa tcatcaagtt tttgaacgca    360

ccttgcacct tttggtattc caaaaggtac acctgtttga gtgtcatgaa atcttctcaa    420

cattatttct ttttttttaaa gggaaattgt tggattttga gtgttgctgt tgcttttttt    480

gcagctcact ttaaataaat aaatatatat aagtttcagt atattttgat gtaataataa    540

aatcatttca tcaaaaaaat aaatatatgt gagatttatt ataacattaa ttgaatgtaa    600

attttttttt aagacctcaa atcaggtgag actacccact gaacttaagc atatcaataa    660

gcggagga                                                             668
```

<210> SEQ ID NO 51
<211> LENGTH: 624
<212> TYPE: DNA
<213> ORGANISM: Artificial
<220> FEATURE:
<223> OTHER INFORMATION: Fusarium sambucinum translation elongation
      factor 1 alpha

<400> SEQUENCE: 51

```
tcgtcgtcat cggccacgtc gactctggca agtcgaccac tgtaagttga cccaaatcta     60

agctcgccta caattggcgg ggtagcctca agatacgctt gtgctgacat acatcataga    120

ccggtcactt gatctaccag tgcggtggta tcgacaagcg aaccatcgag aagttcgaga    180

aggttggtct cattttcctc gatcgcgcgc cctactttcc atcgatccat cattcgaatc    240

gctctgatac gactcgacac acgcctgcta ccccgctcga gttcaaaaat tttacgactt    300

tgtcgtaatt tttttggtgg ggctcatacc ccgccacttg agcgacatgc ccttcctcta    360

aagccacggg cgcgcatcat cacgtgttga tcagttacta acaacctgtc aataggaagc    420

cgccgagctc ggtaagggtt ctttcaagta cgcttgggtt cttgacaagc tcaaagccga    480
```

-continued

```
gcgtgagcgt ggtatcacca tcgatatcgc tctctggaag ttcgagactc ctcgctacta    540

tgtcaccgtc attggtatgt tgtcactacc acctccatca cattcccgca ctaactcacc    600

tatcagacgc tcccggtcac cgtg                                           624
```

<210> SEQ ID NO 52
<211> LENGTH: 279
<212> TYPE: DNA
<213> ORGANISM: Artificial
<220> FEATURE:
<223> OTHER INFORMATION: Phytophthora infestans elicitin gene

<400> SEQUENCE: 52

```
gccctcgtcg gctccacttc cgccaccacg tgcaccacct cgcagcagac cgtagcgtac     60

gtggcgctcg taagcatcct ctcggacacg tcgtttaatc agtgctcgac ggactccggc    120

tactcgatgc tgacggccac ctcgctgccc acgacggagc agtacaagct catgtgcgcg    180

tcgacggcgt gcaagacgat gatcaacaag atcgtgtcgc tcaacgctcc cgactgcgag    240

ctgacggtgc caactagtgg cctggtactc aacgtgttc                           279
```

<210> SEQ ID NO 53
<211> LENGTH: 1096
<212> TYPE: DNA
<213> ORGANISM: Artificial
<220> FEATURE:
<223> OTHER INFORMATION: Sclerotinia sclerotiorum RNA Polymerase Subunit

<400> SEQUENCE: 53

```
ctgttccgca gattaacaac agatgtctac aggtacctgc aacgttgcgt ggaaaacaac     60

agagagttca atttgacgct gggtgtgaaa tccacgacga tcacgaacgg tctgaaatat    120

tctttggcta caggtaactg gggtgaccag aagaaggcag caagttctac cgctggtgtt    180

tctcaagtat tgaacagata taccttcgca tcaacacttt ctcatttgcg ccgaaccaat    240

acgcctatcg gacgtgatgg aaagatcgcc aaacctagac aactgcataa tactcattgg    300

ggtctggttt gtccagcaga gacgccagaa ggtcaagctt gtggtttggt caagaattta    360

gctttgatgt gttacgttac agttggtacg ccaagtgatc caatcgttga gttcatgatt    420

caacgaaata tggaagtgct ggaggagtat gaaccgctcc gagcacccaa tgcaacaaag    480

gtcttcgtca atggtgtttg ggttggtgtc catcgagacc ctgcccattt ggttaaatgt    540

gtacaagatc ttcgtagatc acatttgatt tctcatgaag tctcacttat tcgagaaatt    600

cgagacagag agttcaagat tttcactgat gcaggacgag tgtgcagacc tctgttggtc    660

atcgacaatg atccagacag ccccaacaaa ggtaatttgg tactgaacaa ggatcacatc    720

cgccgtttgg aggatgatca atctctgcca tcgaacatgg ataaggatga gaaagtacac    780

catggttatt atggattcca aggtttgatt aatgatggtg tggttgaata tttagacgcc    840

gaggaagagg agactgttat gattaccatg acacctgaag atttggatat ttctcgacag    900

cttcaagctg gttatcaaat tcgtcctgat gacagcggtg atttgaataa gcgtgtcaag    960

gcacctatca atccaactgc gcacgtctgg actcattgtg aaattcatcc aagtatgatt   1020

ctgggtatct gtgcaagcat cattcccttc ccggatcata atcaggtaag ctttaagtcc   1080

aataatgaat ttatta                                                   1096
```

<210> SEQ ID NO 54
<211> LENGTH: 538
<212> TYPE: DNA
<213> ORGANISM: Artificial

<220> FEATURE:
<223> OTHER INFORMATION: tenocarpella maydis rRNA

<400> SEQUENCE: 54
gggggacgat tattctttct gaaccctgtg aactacctaa acgttgcttc ggcgggaata 60
gacggccccg tgaaacgggc cgcccccgcc agaggaccct taactctgtt tctataatgt 120
ttcttctgag taaaacaagc aaataaatta aaactttcaa caacggatct cttggctctg 180
gcatcgatga agaacgcagc gaaatgcgat aagtaatgtg aattgcagaa ttcagtgaat 240
catcgaatct ttgaacgcac attgcgcccg ccagtattct ggcgggcatg cctgttcgag 300
cgtcattaca acctcaggcc cccgggcctg gcgttgggga tcggcggagc cccccgtggg 360
cacacgccgt cccccaaata cagtggcggt cccgccgcag cttccatcgc gtagtagcta 420
acacctcgcg actggagagc ggcgcggcca cgccgtaaaa cacccaactc ttctgaagtt 480
gacctcgaat caggtaccaa tacccgctga acttaagcat atcaataagc cgggagga 538

<210> SEQ ID NO 55
<211> LENGTH: 536
<212> TYPE: DNA
<213> ORGANISM: Artificial
<220> FEATURE:
<223> OTHER INFORMATION: Cercospora zeae-maydis 18s rDNA

<400> SEQUENCE: 55
tccgtaggtg aacctgcgga gggatcatta ccgagtgagg gccttcgggc tcgacctcca 60
accctttgtg aacacaactc gttgcttcgg gggcgaccct gccgtttcga cggcgagcgc 120
ccccggaggc cttcaaacac tgcatctttg cgtcggagtt taagtaaatt aaacaaaact 180
ttcaacaacg gatctcttgg ttctggcatc gatgaagaac gcagcgaaat gcgataagta 240
atgtgaattg cagaattcag tgaatcatcg aatctttgaa cgcacattgc gccctttggt 300
attccgaagg gcatgcctgt tcgagcgtca tttcaccact caagcctagc ttggtattgg 360
gcgccgcggt gttccgcgcg cctcgaagtc tccggctgag ctgtccgtct ccaagcgctg 420
tgatttcatt aatcgcttcg gagcgcgggc ggtcgcggcc gttaaatctt tccaaggttg 480
acctccggat caggtaggga tacccgctga acttaagcat atcaataagc gcagga 536

<210> SEQ ID NO 56
<211> LENGTH: 1017
<212> TYPE: DNA
<213> ORGANISM: Artificial
<220> FEATURE:
<223> OTHER INFORMATION: Myzus persicae cathepsin B protease

<400> SEQUENCE: 56
atggctaggg tattgatgtt attgtctgtg atcttcgtca gcgtttatat gacggaacaa 60
gcatacttct tggaaaaaga tttcattgac aatatcaatg cacaagcgac tacatggaag 120
gctggtgtga acttcgaccc caaaacatca aaggaacata tcatgaaact tttgggatca 180
aggggagtac aaattccaaa caaaaataat atgaatttgt acaagagcga agatgcagag 240
tacgacaaca catacattcc aaggttcttt gacgctagga gaaaatggag acattgtagt 300
acgatcggaa gagtccgtga ccaaggaaac tgtggatctt gttgggctgt ggccactagc 360
tcggctttcg ctgaccgttt gtgtgtagca acaaatgcag acttcaacga attattatcc 420
gccgaagaaa tcactttctg ctgtcataca tgtggcttcg gatgcaacgg tggttacccg 480
attaaagcat ggaaacgttt tagtaaaaaa ggtttagtca ccggaggaga ctacaaatct 540
ggagagggtt gtgaaccata cagagttcca ccttgtccta atgacgacca aggaaataat 600
acatgcgccg gtaaaccaat ggaatcaaac cacaggtgta ccaggatgtg ctacggtgac 660
caggacctcg acttcgacga agaccacaga tacacacgtg attactacta cctaacatac 720
ggtagcatcc aaaaggacgt catgacttac ggaccaattg aagcatcgtt cgatgtatac 780
gacgatttcc ccagttacaa gtcaggcgtt tacgtgaaat cggaaaatgc ttcatacttg 840
ggaggacatg ccgttaaatt gatcggttgg ggtgaagaat acggagtgcc atactggttg 900
atggtcaact catggaacga agattggggt gaccatggtt ttttcaaaat tcaacgaggc 960
acaaacgaat gtggagtcga taattcgaca actgctggtg taccagttac caactaa 1017

<210> SEQ ID NO 57
<211> LENGTH: 248
<212> TYPE: DNA
<213> ORGANISM: Artificial
<220> FEATURE:
<223> OTHER INFORMATION: Leptinotarsa decemlineata cysteine protease

<400> SEQUENCE: 57
attatgggcc cgggggatca aactggaatt cagtgggtgg gattggaata taacatcatt 60
ttcatggatg aagttcttca ttatattctt ttttctctcg ccgcaacaga agctcttagt 120
gataagggag aaatggcaga atttcaaaat caatttctcc aagtcctacc aaaacgtggt 180
agaagaaaaa gggcgtttca atattttcct gtcgaatttg ttgaggatcg aagaacacaa 240
ccaaaatt 248

<210> SEQ ID NO 58
<211> LENGTH: 519
<212> TYPE: DNA
<213> ORGANISM: Artificial
<220> FEATURE:
<223> OTHER INFORMATION: Verticillium dahliae rDNA

<400> SEQUENCE: 58
aggacattac gagtatctac tcataaccct ttgtgaacca tattgttgct tcggcggctc 60
gttctgcgag cccgccggtc catcagtctc tctgtttata ccaacgatac ttctgagtgt 120
tcttagcgaa ctattaaaac ttttaacaac ggatctcttg gctctagcat cgatgaagaa 180
cgcagcgaaa cgcgatatgt agtgtgaatt gcagaattca gtgaatcatc gaatctttga 240
acgcacatgg cgccttccag tatcctggga ggcatgcctg tccgagcgtc gtttcaaccc 300
tcgagcccca gtggcccggt gttggggatc tacgtctgta ggcccttaaa agcagtggcg 360
gacccgcgtg gcccttcctt gcgtagtagt tacagctcgc atcggagtcc cgcaggcgct 420
tgcctctaaa ccccctacaa gcccgcctcg tgcggcaacg gttgacctcg gatcaggtag 480
gaatacccgc tgaacttaag catatcaata agcggagga 519

<210> SEQ ID NO 59
<211> LENGTH: 762
<212> TYPE: DNA
<213> ORGANISM: Artificial
<220> FEATURE:
<223> OTHER INFORMATION: Peronospora manchurica rDNA

<400> SEQUENCE: 59
ctaaaaaaac tttccacgtg aaccgtatca accttttaaa ttggggacaa tgatcttggt 60
ggaggcttct agtcttttgg ctagctgttc actactataa gtgagtccta tcatatcgaa 120
ccattagaca tgaatttgtc atatgaagta gaagaagtta taaaccctta cctaatttac 180
tgattatact gtggggacga aagtctctac ttttattcta gataacaact ttcagcagtg 240
gatgtctagg ctcgcacatc gatgaagaac gctgcgaact gcgatacgta atgcgaattg 300
ctaaattcag tgagtcatcg aaattttgaa cgcatattgc acttctcggg ctagtctcct 360
gaagtatgcc tctatcagtg tccacacaac aaacttggct ttcttttttc cgtgtattcg 420
gtgaaggata tgccagatat gaagtgtctt gccctcaatt ttcgaattgg ccgcaagtcc 480
ttttaaatgt aaagactgta cttattgtgc ttgaaaagcg tgacgatact agtttagaaa 540
ctgttcgttt ggccagtcgg cgacgagttt gttaactata actttatgga gaattattcg 600
atttgcggta tgattggctt cggctgaact acgtttattg gattcttttt gtcggttata 660
gaagtatgaa cttgtgaacc gtagctaagc atgtgatgga tttttttacc tgtgttattg 720
ctgcgaagta aagtgtcaac ttcggttgtc cgataagtcg ac 762

<210> SEQ ID NO 60
<211> LENGTH: 521
<212> TYPE: DNA
<213> ORGANISM: Artificial
<220> FEATURE:
<223> OTHER INFORMATION: Meloidogyne chitwoodi cytochrome oxidase II

<400> SEQUENCE: 60
ggtcaatgtt cagaaatttg tggtgttaat cattctttta tgcctattat aattgaggtt 60
gttttatttg atttttttaa gataagttta attagctttt tattttatta gaatttttta 120
ttgtgattaa aaaagatttg agctaatata ttattttttg ttgttgaaaa aattaaaaaa 180
aaattataag ttataataat taaaattcta aaaaaggatt atttgttttt tagttaaata 240
ttataaatat aatggtttaa aaaagagaaa ttttgattag aataatatta gttttttttt 300
atatttttta taataattgt ttattttttta taattatttt tttttataaa aataatttaa 360
ttattattat tttatttaaa aaaattaatt aaattaattt ttttgttaaa ttagtttaaa 420
tataaaatgt tttttaaaat ctgatgaatt tttggtttta attttttatt tctgctcagt 480
gatttattga atggtatctt tagcgtgatt ggtcaaaggt a 521

<210> SEQ ID NO 61
<211> LENGTH: 1773
<212> TYPE: DNA
<213> ORGANISM: Artificial
<220> FEATURE:
<223> OTHER INFORMATION: Pratylenchus scribneri rDNA

<400> SEQUENCE: 61
gcttgtctca aagattaagc catgcatgta taagtataaa cgctctgaag cgtgaaaccg 60
cgaacggctc attacaacag ctataattta cttgatcttg attacctact tggataactg 120
tggwaattct agagctaata catgcaccaa agctccaacc cgtaagggaa gagcgcatty 180
attagaacaa aaccatgcgg cttcggccgc tcaatgttga ctcagaataa ctaagctgat 240
cgcatggtct tgtaccggcg acgtgtcttt caagtatctg ccttatcaac tttcgatggt 300
actgtcattg actaccatgg tggtgacggg taacggagga tcagggttcg actccggaga 360
aggggcctga gaaatggcca ctacgtctaa ggatggcagc aggcgcgcaa attacccact 420
ctcagaacaa tttgaggagg tagtgacgag aaataacgag accgttctca acagaggccg 480
gtcatcggaa tgggtacwat ttaaaccctt taacgagtat ctatgagagg gcaagcctgg 540
tgccagcagc cgcggtaatt ccagctctca aaatgcatag aattattgct gcggytaaaa 600
agctcgtagt tggatctgtg ccgacagact ggtccatctt cggatgcgta ctggttattg 660
tcggctttcc tgcagttttg cggctcagtg cctctcacgg ggtgcagtgt ccgttgctgc 720
aagtttactt tgaacaaatc agagtgctct aaacaggcgt ttcgcttgaa tgttcgtgca 780
tggaataata gaagaggatt tcggttctat tttattggtt ttatagactg agataatggt 840
taacagagrc aaacgggggc attcgtattg ctacgtgaga ggtgaaattc ttggaccgta 900
gcaagacgaa ctacagcgaa agcatttgcc aagaatgtct tcattaatca agaaygaaag 960
tcagaggttc gaaggcgatc agataccgcc ctagttctga ccgtaaacga tgccaactag 1020
ckatccgccg gcggaattct tgccctggtg gggagcttcc cggaaacgaa agtcttccgg 1080
ttccgggga agtatggttg caaagctgaa acttaaagga attgacggaa gggcaccacc 1140
aggagtggag cctgcggctt aatttgactc aacacgggaa aactcacccg gcccggacac 1200
cgtaaggatt gmcagattga tagctttttc atgattcggt ggatggtggt gcatggccgt 1260
tcttagttcg tggagcgatt tgtctggytt attccgataa cgagcgagac tctggcctac 1320
taaatagtcg gcgcattgtc tctgtgtgca tgacttctta gagggatttt cggtgttcag 1380
ccgcacgaaa ttgagcaata acaggtctgt gatgccctta gatgtccggg gctgcacgcg 1440
cgctacactg gcaaaatcag cgtgcttgtc ctcctccgaa aggagttggt aaaccattga 1500
aaatttgccg tgattgggat cggaaattgc aattattttc cgtgaacgag gaaytccaag 1560
taagtgcgag tcatcaactc gcgttgatta cgtccctgcc ctttgtacac accgcccgtc 1620
gctgcccggg actgagccat ttcgagaaac ttggggaccg ctgatttgca gtctttcggg 1680
cctgcttatt ggtgggaacc aatttaatcg cagtggcttg aaccgggcaa aagtcgtaac 1740
aaggtagctg taggtgaacc tgcagctgga tca 1773

<210> SEQ ID NO 62
<211> LENGTH: 949
<212> TYPE: DNA
<213> ORGANISM: Artificial
<220> FEATURE:
<223> OTHER INFORMATION: Heterodera glycines rDNA

<400> SEQUENCE: 62
gtgattccta ttcaccacct acctgctgtc ctgttgggct agcgttggca ccaccaaatg 60
cccccgtccg ctgatgggca caggtcgttc gagatgactt gtggacgctg cccaacatta 120
cggggcagct gcctcacgag ccatgctttt ggggtgcttc catacgttgg agctgtggta 180
taccgctcag tgctgcacat gtgaaagcct gtgtatggct gctgcgtggc aatgtgtcgg 240
tggcgggccg cctcgcttgg ctggttcgct gcgccaatgt gggatgcacg ctcgtggggc 300
gacctaacgg ctgtgctggc gtctgtgcgt cgttgagcgg ttgttgtggc aggcacataa 360
cacactgact ggggatggtg gtttcgttcc cggtcttacg tgccgtaact agcggtgtgt 420
ttgtgcttgc tgctacgtcc gtggccgtga tgagacgacg cggtagggcc cgtgcttggc 480
ctagcacgtg gcttaagact caatgagtgt cagctcgggc accgccagct ttttcttttt 540
tttttcatta ttttttttta cacttctgtt gaagaatgaa ttctagtctt atccggtgga 600
tcactcggct cgtggatcga tgaagaacgc agccaactgc gataattagt gcgaactgca 660
gaaaccttga acacaaaaca ttcgaatgca cattgcgcca ttggagttac atccattggc 720
acgcctggtt cagggtcgtt accataaaat gcactgcttg tgcgttgctt cgtgggatca 780
tgtacttgta cgtgttctta cgttacttgc tcagctcggc tgtggggttt tggtgtgctg 840
gcgcgaactt gtggttctaa ttcgcgtttt acggaccgta actcgggcgc accaatgctt 900
tgcatgctgt ggcggagtgc ctggattact ggcattacct gctttgatt 949

<210> SEQ ID NO 63
<211> LENGTH: 1120
<212> TYPE: DNA
<213> ORGANISM: Artificial
<220> FEATURE:
<223> OTHER INFORMATION: Magnaporthe grisea RNA polymerase II

<400> SEQUENCE: 63

```
atgaagcctg aggacctaaa gaaaatggac attgccacaa aagacacaga cgcacggcga     60

cctggtcacc ttcgagccct taaccgtagc agcgacaccg atttcaccga ctcccgccta    120

aaaccagaac cgcttcgtct aggtcgcagg gatgtttctg gtgcagaatc gactcacatg    180

tctctcgacg acagtctgat gtcaccagat ccaggggcat tggcaggtga tgaagactca    240

gatctgggaa aatgcgagcg caactgggag gcggagagct taggatcgcc cgtcagcaac    300

ggtatacata gcccatcaca catgggtgag caagcacctc ccttttcgga ctacaaccct    360

tctgaatctc ctccagaagc aatcgtacat cgagagcaag gtgattctgc ccagatggac    420

gcgaaatcct cgtcgcaatc gcggcactct gtctatgcta acttggtagt tcctgagtcc    480

aaaccactaa cccgacaatc cagcctggct cagctccgac agcctattga ggcaaaggca    540

gaagctcgtt ccaggccagc gtccattcta atagttccta cacaggggag tgctacgccc    600

tcgataaata ctcctatatt tgagaaaaga ttggcaacca gaagcccaga gactccgtca    660

attgtacagc cagcaaatat ttcgacgccc agttccatgg ttcataagaa ggagtctgca    720

ggaacccata gtcgaccagc tatacaatcc tctttctccg attcacccaa tgcagcttgg    780

cctggtaatt tgctttcagc caggggtcta gattacaaac tacgatcaag actgtccgag    840

ccagctcttg taagaagcgg ccagaaaaaa ccgtctagtg ttggcgggca tcctggatat    900

accactcccg taccggttac accccaaagg cctgtgacaa agtcttcggt cttacactca    960

agcccggtcc accacctaat gcgctctgca aataccgtgt cttctcgaca ttccattgcg   1020

acaacagata ggcatgctac aaccggtggc gcatctcaga gtgggggtac gagccacaag   1080

ctgggagctc agtcgtgtcc gaaccgagtt gcagagcttc                         1120
```

<210> SEQ ID NO 64
<211> LENGTH: 883
<212> TYPE: DNA
<213> ORGANISM: Artificial
<220> FEATURE:
<223> OTHER INFORMATION: Puccinia hordei 18S rDNA

<400> SEQUENCE: 64

```
agtgaaactg cgaatggctc attaaatcag ttatagttta tttgatgata ccttactaca     60

tggataactg tggtaattct agagctaata catgctgaaa agccccaacc tttggaaggg    120

gtgtatttat tagataaaaa accaatggcc cttgggtctc cttggtgatt cataataact    180

tctcgaatcg catggccttg tgccggtgat gcttcattca aatatctgcc ctatcaactt    240

tcgatggtag gatagaggcc taccatggtg atgacgggta acggggaata agggttcgat    300

tccggagaga gggcctgaga aacggccctc aaatctaagg attgcagcag gcgcgcaaat    360

tacccaatcc tgacacaggg aggtagtgac aataaataac aatgtatggc tcttttgggt    420

cttacaattg gaatgagtac aatttaaatc tcttaacgag gatcaattgg agggcaagtc    480

tggtgccagc agccgcggta attccagctc caatagcgta tattaaaatt gttgacgtta    540

aaaagctcgt agtcgaactt cggcctctgg cagttggtcc gccttttggt gtgtactgat    600

ttgttggagg cttacctctt ggtgaacttc aatgcacttt actgggtgtt gaaaggaacc    660

aggactttta ctttgaaaaa attagagtgg ttcaaagcag cttatgcctg aatacattac    720
```

catggaataa taaaatagga cgtgtgattc tattttgttg gtttctagga ttaccgtaat 780
gatgaataag gtcagttggg ggcatttgta ttacatcgtc agaggtgaaa ttcttggatt 840
gatgtaagac aaactactgc gaaagcatct gccaaggatg acc 883

<210> SEQ ID NO 65
<211> LENGTH: 802
<212> TYPE: DNA
<213> ORGANISM: Artificial
<220> FEATURE:
<223> OTHER INFORMATION: Pseudoperonospora humuli rDNA

<400> SEQUENCE: 65
ccacacctaa aaactttcca cgtgaactgt ttcaacctca ttaattgggg gttttgtttg 60
gcggtgatcg ctagcttaat tgctggttga ttactgctag gcgagcccta tcatggcgag 120
cgtttgggct tcggtctgaa ctagtagctt ttattttaaa ccctttctta attactgatt 180
atactgtggg gacgaaagtc tctgctttta actagatagc aactttcagc agtggatgtc 240
taggctcgca catcgatgaa gaacgctgcg aactgcgata cgtaatgcga attgcaggat 300
tcagtgagtc atcgaaattt tgaacgcata ttgcacttcc gggttagtcc tgggagtatg 360
cctgtatcag tgtccgtaca tcaaacttgg ttttcttctt tccgtgtagt cggtggagga 420
tatgccagat gtgaagtgtc ttgcggctaa ttttagaatt gactgcgagt cctttgaaat 480
gtacagaact gtacttctct ttgctcgaaa agtgtggcgt tgctggttgt gaaggctgtc 540
catgtgacca gtcggcgatc ggtttgtctg ctatggcatt aatggaggaa tatttaattc 600
gcggtatgat tagcttcggc tgaacaggcg cttattgaac gtttttcctg ttgtggcggt 660
atgaactgat gaaccgtagt cgtgtgtgac ttggcttttg aattggcttt gctattgcga 720
agtagagtgg cagtttcgac tgtcgagggt cgacccattt gggaactatg tgttgtgtgg 780
cttcggtcgc gcggcatctc aa 802

<210> SEQ ID NO 66
<211> LENGTH: 1260
<212> TYPE: DNA
<213> ORGANISM: Artificial
<220> FEATURE:
<223> OTHER INFORMATION: Botrytis cinerea cytochrome P450 monoxygenase

<400> SEQUENCE: 66
ctttattcga tattaatagt attatatgtt atacagagac tataaagaaa atatatgttt 60
tcctttttaa tattagattt ttactttttt ataataatga tttattttta ttattatatt 120
agtctcttta atattgaaat aatatttatt agaaacaata taagaaatag ctaacttgaa 180
attaaaaagt ataaaatcta acaaatctat agaatagaat cttgtaaact ttattaaact 240
tgaaagatat ttaaatatat atttaagatc tcctaaacct cctcttttta aatcagtcag 300
tagatctcct atattctaaa aattaagaaa gttagcatgt gaattaatat ttaggcaggt 360
gttccacacg atatctagaa aaggagcttc tagaccctcc cgtctagacc ctcccgttta 420 gaccccccccg tctagaccta ccctccggca aaccttcggg tatttaccga atcaaaaagg 480
ctaggatgtg gggctgagta aactctagat tgtgaccccc actatgggtc tgacagccct 540
agaaacaact taatctgttt ggatattgcg gggtttcact gcggagtctt gtatgtagat 600
cgaaagtcgc caagcccatg aaacatttca aggtgtaaag tatgttacgg atttaagttt 660
gcttccagcc caatcgtaag ccttatctct gacgttgaac tgaagtttag agtttcctgt 720
aagcatatac acttgaaagt acatcctcct caatctgcgg tgattatgcg tttttttttc 780
gcaactcttg taatacgaac acaactactc acaatcactc ttatgaaatt tacttgtccc 840
aaaaggacat catgctgctt agcattaaag acctgtctga aaaatacatc atgctgctcg 900
atgtcaaaga tctgtcgaca ctcaaaacaa ctgttgccgt tctagtgagt ccattattca 960
taccagaggg agggtaattc cttaacatga ccaggtcacg gtagccctta ttgcacaagt 1020
cctttggaaa attttctttc acccgctcag tgcctttcca gggccgtggt tcaacaggat 1080
atccgaaata cccggctcgt gggttattgc aactgggaag cagcactcat attaccggaa 1140
gcttcatgaa aaatatggtg agtaactatt cctgtacctt gctccttctt tcgggaaaca 1200
agttcatact aaaacaaatt caggcccagt tgtgagagtt gccccaaatg agctcagctt 1260

<210> SEQ ID NO 67
<211> LENGTH: 536
<212> TYPE: DNA
<213> ORGANISM: Artificial
<220> FEATURE:
<223> OTHER INFORMATION: Pseudomonas syringae rDNA

<400> SEQUENCE: 67
atcgacgact cagctgcacc ataagcaccc acacgaattg cttgattcat tgaagaagac 60
gatgagaagc agcttttgct ttgcacaccc gattttgggt ctgtagctca gttggttaga 120
gcgcacccct gataagggtg aggtcggcag ttcgaatctg cccagaccca ccagttacct 180
ggtgaagttg gtcagagcgc gtacgacacc cggatacggg gccatagctc agctgggaga 240
gcgcctgcct tgcacgcagg aggtcagcgg ttcgatcccg cttggctcca ccacttactg 300
cttctgtttg aaagcttaga aatgagcatt ccaccctgag agattgaagg gtgcgtgaat 360
gttgatttct agtctttgat tagatcgttc tttaaaaatt tgggtatgtg atagaaagaa 420
atatagaccg ggcacctctt tcactggtgc gtgtccgggc taaggtaaag tttgtgaaat 480
gcaaactttc ggcgaatgtc gtcttcacag tataaccaga ttgcttgggg ttatat 536

<210> SEQ ID NO 68
<211> LENGTH: 983
<212> TYPE: DNA
<213> ORGANISM: Artificial
<220> FEATURE:
<223> OTHER INFORMATION: Clavibacter michiganense michiganense Cel A
gene

<400> SEQUENCE: 68
atgactgttc gacaagttag tgtaccctta gtgtccaagc tcttcctttt ctttgcattg 60
gcggtcggcg ccacgtttgg cgcattcgcg gcgcctgcct tagccgccac cgcagcgggg 120
accggtgcgg tggcctcgcc gcctggatgg ctgcacacgg cgggtgggaa gatcgtcacc 180
gcctccggcg ctccgtacac aatccgtggc atcgcgtggt ttggcatgga gacgtcatcc 240
tgcgcgccgc acggcctgga caccatcacc ctcgcgggtg gcatgcagca catcaagcag 300
ctgggattca cgaccgtgcg gctgccgttc tcgaaccagt gcctcgcggc atctggcgtc 360
acgggtgtcg atgcggaccc atcgcttgcc ggtctcacac cgctgcaggt catggatcac 420
gtcgtggctt cggcgaaggc cgccggactt gacgtgatcc tcgaccagca ccggccggac 480
tcgggcggcc agtccgagct ctggtacacc tcggagtacc ccgagtcacg gtggatctcc 540
gactggcgga tgctcgcgaa gcggtacgcc tccgacccca cggtcatcgg tgtcgatctc 600
cacaacgagc cgcacggggc ggcgacgtgg ggtaccgggg cagccacgac cgactggcgg 660
gcggcggccg agcggggcgg gaacgcggta ttggccgaga acccgaagct cctcgtgctc 720

-continued

```
gtcgagggaa tcgaccacca ggccgacgga accggcacct ggtggggcgg tgcgctggac    780

tccgcggcca ctgcatccgt gcgcttgacc gtcgcgaatc gcgtcgtcta ttccccgcac    840

gactacccct cgaccatcta cggccagccc tggttctccg catcgaatta tccgacgaat    900

cttccgggaa tctgggacgc ccactgggga tacctggcaa agaaggacat cgcccccgtc    960

ctcgtgggcg agttcggtac gaa                                            983


<210> SEQ ID NO 69
<211> LENGTH: 1260
<212> TYPE: DNA
<213> ORGANISM: Artificial
<220> FEATURE:
<223> OTHER INFORMATION: Clavibacter michiganense endo B-glucosidase
      gene

<400> SEQUENCE: 69

ctcagggaac taaccggatg agcactgttt cgggcgtgag gagtgcgtgc gaaaggcgtc     60

tgtggaagtg gttttcagtg cggccggatg gcttccctac gatccttata tgacatttcg    120

ccaagttcgt gcatccttag tgcttcggct cgtccttctc cttgcgttgg tggtcggcac    180

cacgtccgcc gcattcgctg cgcctgtctc agccgccacc gtagcggggc ccgttgcggc    240

ggcctcatcg cctggatggc tgcatacggc gggcgggaag atcgtcaccg cctccggtgc    300

tccgtacacg atccgtggca tcgcttggtt tggcatggag acgtcgtcgt gcgcgccgca    360

tggcctggac accatcaccc tcgcgggcgg tatgcagcac atcaagcaga tggggttcac    420

gaccgtgcgg ttgcccttct cgaaccagtg cctcgccgcg tccggcgtca cgggtgtcag    480

tgcggacccg tcactcgccg ggctcacgcc gctgcaggtc atggaccacg tcgtcgcgtc    540

ggcgaagagc gccggtcttg acgtgatcct cgaccagcac cggccggact cgggcggcca    600

gtctgagctc tggtacacat cgcagtatcc ggagtcgcgg tggatctccg actggaggat    660

gctcgcaaag cgctatgcag ccgaacccac cgtcatcggt gtagacctcc acaacgaacc    720

gcacggtgcg gcgacctggg gtaccggggc ggccaccact gactggcggg cagcggccga    780

gcgtggcggg aatgcggtcc tcgccgagaa cccgaacctc ctcgtgctcg tggagggcat    840

cgaccacgag gccgacggat ctggcacctg gtggggcggc gcgctcgggt tggtaggcaa    900

tgcacctgtg cggctgtcgg tcgcgaatcg cgtcgtctac tccccgcatg actacccctc    960

gaccatttac ggccagtcat ggttctccgc atcaaactat ccggcgaact tgccgggtat   1020

ttgggacgcc cactggggat acctggcgaa gaaggacatt gccccggttc tcgtgggtga   1080

gttcggtacg aagttcgaga cgacgagcga caagcagtgg ctcaacaccc tcgttggata   1140

tctgtcgagc acggggatca gctcgtcgtt ctgggccttc aacccgaata gtggcgacac   1200

cggcggtatc gtgaagtccg actgggtgac cccggagcag gcgaagctcg acgccctggc   1260
```

METHODS AND MATERIALS FOR CONFERRING RESISTANCE TO PESTS AND PATHOGENS OF PLANTS

CROSS-REFERENCE TO RELATED APPLICATIONS

This is a divisional of U.S. patent application Ser. No. 11/256,428 filed 21 Oct. 2005, now U.S. Pat. No. 8,148,604 which claims priority to U.S. Provisional Patent Application Ser. Nos. 60/657,821 filed 1 Mar. 2005 and 60/621,542 filed 21 Oct. 2004, each of which is incorporated by reference herein by its entirety.

BACKGROUND OF THE INVENTION

Plant pests (e.g. fungal pathogens, bacteria, nematodes, insects, viruses, etc.) cause major losses of food and fiber throughout the world, especially in developing countries. Losses include direct production or pre-harvest losses, post-harvest and storage losses, and the diminution of food quality and safety (e.g. by production of mycotoxins). Other resultant losses from plant pests are observed in plants valued for aesthetic, olfactory, or ecologic properties.

Plant pests can sometimes be controlled by application of chemicals (e.g. fungicides, insecticides, nematicides, parasiticidals), manipulation or management of the microenvironment or by genes for resistance to the pathogen.

Discovery and introduction of a "new" gene for resistance frequently causes the development or selection of a new race of the pathogen able to infect plants containing that "new" gene. This has best been demonstrated by the rusts and smuts of cereal crops, but it also occurs with soil borne diseases such as black shank of tobacco and root and stem rot of soybean, caused by *Phytophthora nicotianae* and *P. sojae*, respectively. There are at least two races of *P. nicotianae* and more than 70 races of *P. sojae*, all requiring different genes or combinations of genes for disease resistance.

The fungal genus *Phytophthora* comprises many species of very destructive pathogens which cause serious diseases of plants. These include blights, damping-offs, cankers, fruit rots, root rots, wilts, and many other symptoms that affect a wide variety of food, fiber and oil crops including avocado, cacao, canola, citrus, pepper, potato, soybean, tobacco, tomato, pine, rubber, oak trees, etc.

In the past decade the phenomenon of gene silencing or RNA interference (RNAi) has been described and characterized in organisms as diverse as plants, fungi, nematodes, hydra and humans (Zamore and Haley, 2005). It is considered to be an ancient defense mechanism wherein the host organism recognizes as foreign a double-stranded RNA molecule and hydrolyzes it. The resulting hydrolysis products are small RNA fragments of 21-30 nucleotides in length, called small interfering RNAs (siRNAs). The siRNAs then diffuse or are carried throughout the host, where they hybridize to the mRNA for that specific gene and cause its hydrolysis to produce more siRNAs. This process is repeated each time the siRNA hybridizes to its homologous mRNA, effectively preventing that mRNA from being translated, and thus "silencing" the expression of that specific gene.

Fire et al. (2003) describe a method of administering RNA to a host wherein the RNA is composed of sense and antisense sequences homologous to a gene of that host cell to silence that host cell's gene. See U.S. Pat. No. 6,506,559.

Results by van West et al. (1999) demonstrated internuclear gene silencing in *Phytophthora infestans*. They transformed *P. infestans* with the inf1 elicitin gene in both the sense and antisense orientations. This resulted in silencing of both of the transgenes, as well as the endogenous gene. By somatic fusion of a silenced transgenic strain and a wild-type strain, they demonstrated two essential points; first, that the presence of the transgene itself is not necessary to maintain the silenced state; and second, the involvement of a trans-acting factor capable of transferring the silencing signal between nuclei, later found to be the siRNAs.

Waterhouse et al. (WO9953050A1) have described methods of conferring viral resistance to a plant by transforming the plant with a gene silencing construct directed towards a plant viral gene.

Wang et al. (US20030180945A1) describe a method of gene silencing in a fungus by providing the fungus with a gene silencing construct directed towards a fungal gene.

What is needed in the art is a plant resistance method that is readily adaptable to changes in the biological environment such as a new and serious plant disease. For example, there were no occurrences of Asian rust in soybean in the USA until November 2004. Asian rust is predicted to cause losses estimated at 1 to 7 billion dollars (USDA) in 2005-2006.

The art would also be substantially advanced if there existed a versatile genetic method of conferring resistance to a plant against a spectrum of fungi, insects, nematodes, bacteria, etc.

BRIEF SUMMARY OF THE INVENTION

There is now provided in the present invention a method of conferring pest resistance to a plant comprising the step of transforming a host plant cell with a heterologous polynucleotide, said heterologous polynucleotide comprising:

(a) an antisense sequence having homology to a pest pathogenicity gene, and (b) a sense sequence substantially complementary to said antisense sequence;

wherein a transcript of the heterologous polynucleotide is capable of hybridizing to form a double-stranded region comprising nucleotides encoded by the antisense sequence and the sense sequence;

wherein said sense and antisense sequences are each at least about 19 nucleotides in length; and wherein the antisense sequence is homologous to the pathogenicity gene of at least two pests from different species whereby the plant is resistant to said two pests as compared to substantially the same plant lacking the heterologous polynucleotide.

In another embodiment, the present invention provides a method for conferring pest resistance to a plant comprising a step of transforming a host plant cell with a heterologous polynucleotide, said heterologous polynucleotide comprising:

(a) a first antisense sequence having homology to a first pest pathogenicity gene;

(b) a second antisense sequence having homology to a second pest pathogenicity gene;

(c) a first sense sequence substantially complementary to said first antisense sequence; and (d) a second sense sequence substantially complementary to said second antisense sequence, wherein a transcript of the heterologous polynucleotide is capable of hybridizing to form a double-stranded region comprising nucleotides encoded by the first antisense sequence and the first sense sequence, wherein a transcript of the heterologous polynucleotide is capable of hybridizing to form a double-stranded region comprising nucleotides encoded by the second antisense sequence and the second sense sequence, and wherein said first and second sense sequences and first and second antisense sequences are each at least about 19 nucleotides in length.

Accordingly, a plant can now be made resistant to a plurality of pests belonging to the same or to different members selected from the group consisting of insects, bacteria, fungi, plants, and nematodes.

In another embodiment, the present invention provides a method for conferring pest resistance to a plant comprising a step of transforming a host plant cell with a heterologous polynucleotide, said heterologous polynucleotide comprising:

(a) a first promoter operably linked to an antisense sequence wherein said antisense sequence is homologous to a pest pathogenicity gene and operably linked to a terminator;

(b) a second promoter operably linked to a sense sequence wherein said sense sequence is substantially complementary to said antisense sequence and operably linked to a terminator;

wherein said second promoter is a strong promoter relative to the first promoter, wherein a transcript of the heterologous polynucleotide is capable of hybridizing to form a double-stranded region between sequences encoded by the antisense sequence and the sense sequence, wherein said sense and antisense sequences are each at least about 19 nucleotides in length.

In another embodiment, the present invention provides a method for conferring pest resistance to a plant comprising the step of transforming a host plant cell with a heterologous polynucleotide, said heterologous polynucleotide comprising:

(a) an antisense sequence having homology to a pest pathogenicity gene, and (b) a sense sequence substantially complementary to said antisense sequence, wherein a transcript of the heterologous polynucleotide is capable of hybridizing to form a double-stranded region comprising nucleotides encoded by the antisense sequence and the sense sequence, wherein said sense and antisense sequences are each at least about 19 nucleotides in length, wherein the pest is selected from the group consisting of insects, bacteria, fungi, and nematodes, and wherein the pest pathogenicity gene and the pest are selected from those taught herein.

BRIEF SUMMARY OF THE SEVERAL VIEWS OF THE DRAWINGS

FIG. 4 is autoradiograms showing the siRNAs isolated from transgenic tobacco and from transgenic *Phytophthora nicotianae*.

FIG. 7 shows the results of soybean transformed with pVZA100.

DETAILED DESCRIPTION OF THE INVENTION

Brief Description of the Sequences

Figure 1:
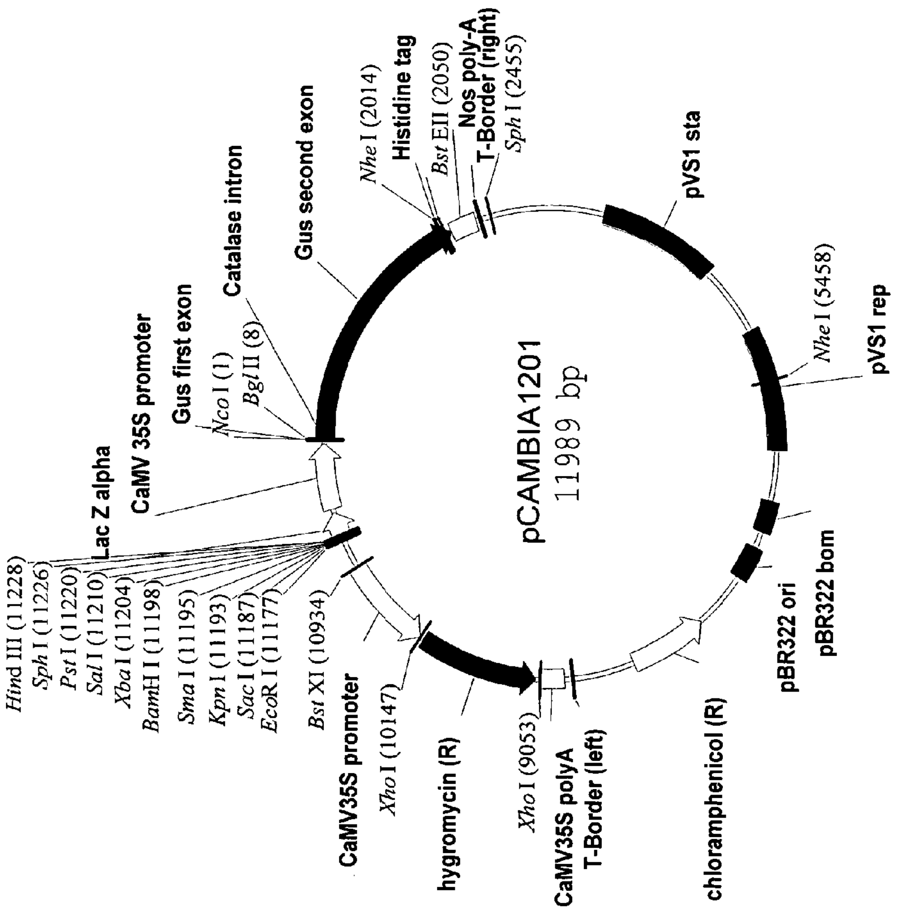
FIG. 1 is the genetic map of the pCAMBIA1201 plant transformation plasmid used as an example throughout this teaching and which is the backbone of pVZA100, pVZA200, pVZA300 and pVZA400.

SEQ ID NO: 1 is the PCR primer VZA 1F as used according to the subject invention.

SEQ ID NO: 2 is the PCR primer VZA 2R as used according to the subject invention.

SEQ ID NO: 3 is the PCR primer VZA 3F as used according to the subject invention.

SEQ ID NO: 4 is the PCR primer VZA 4R as used according to the subject invention.

SEQ ID NO: 5 is the silencing construct pVZA100 used according to the subject invention.

SEQ ID NO: 6 is the silencing construct pVZA200 used according to the subject invention.

SEQ ID NO: 7 is the silencing construct pVZA300 used according to the subject invention.

SEQ ID NO: 8 is the silencing construct pVZA400 used according to the subject invention.

SEQ ID NO: 9 is the forward PCR primer GUS as used according to the subject invention.

SEQ ID NO: 10 is the reverse PCR primer GUS as used according to the subject invention.

SEQ ID NO: 11 is the PCR primer pVZA100 and hygromycin phosphotrasferase as used according to the subject invention.

SEQ ID NO: 12 is the PCR primer pVZA100 and hygromycin phosphotrasferase as used according to the subject invention.

SEQ ID NO. 13 is the primer VZA 1 65R as used according to the subject invention.

SEQ ID NO. 14 is the primer VZA 2 69F as used according to the subject invention.

SEQ ID NO. 15 is the primer VZA 3 73F as used according to the subject invention.

SEQ ID NO. 16 is the primer VZA 3 73F as used according to the subject invention.

SEQ ID NO. 17 is the primer VZA 1 65 as used according to the subject invention.

SEQ ID NO. 18 is the primer VZA 6 70F as used according to the subject invention.

SEQ ID NO. 19 is the PCR primer VZA 7 72F as used according to the subject invention.

SEQ ID NO. 20 is the PCR primer VZA 8 79F as used according to the subject invention.

SEQ ID NO. 21 is the PCR VZA 9 84F primer as used according to the subject invention.

SEQ ID NO. 22 is the PCR VZA 10 87F primer as used according to the subject invention.

SEQ ID NO. 23 is the PCR VZA 11 89F primer as used according to the subject invention.

SEQ ID NO. 24 is the PCR VZA 12 90F primer as used according to the subject invention.

SEQ ID NO. 25 is the PCR VZA 13 91F primer as used according to the subject invention.

SEQ ID NO. 26 is the PCR VZA 14 81F primer as used according to the subject invention.

SEQ ID NO. 27 is the PCR VZA 15 82F primer as used according to the subject invention.

SEQ ID NO. 28 is the PCR primer VZA 6 83F as used according to the subject invention.

SEQ ID NO. 29 is the PCR primer VZA 17 85F as used according to the subject invention.

SEQ ID NO. 30 is the PCR VZA .18 86F primer as used according to the subject invention.

SEQ ID NO. 31 is the PCR VZA 19 64R primer as used according to the subject invention.

SEQ ID NO. 32 is the PCR VZA 20 77F primer as used according to the subject invention.

SEQ ID NO. 33 is the PCR VZA 21 63F primer as used according to the subject invention.

SEQ ID NO. 34 is the PCR VZA 22 66R primer as used according to the subject invention.

SEQ ID NO. 35 is the PCR VZA 23 80F primer as used according to the subject invention.

SEQ ID NO. 36 is the PCR VZA 24 92F primer as used according to the subject invention.

SEQ ID NO. 37 is the PCR primer VZA 25 93F as used according to the subject invention.

SEQ ID NO. 38 is the PCR primer VZA 2R as used according to the subject invention.

SEQ ID NO. 39 is the PCR primer cathepsin as used according to the subject invention.

SEQ ID NO. 40 is the PCR primer elicitin as used according to the subject invention.

SEQ ID NO. 41 is the PCR primer rDNA FP as used according to the subject invention.

SEQ ID NO. 42 is the PCR primer rDNA RP as used according to the subject invention.

SEQ ID NO. 43 is the marker *Phialophora gregata* ribosomal RNA gene (rDNA) as used according to the subject invention.

SEQ ID NO. 44 is the genotype B DNA marker *Phialophora gregata* ribosomal RNA gene (rDNA) as used according to the subject invention.

SEQ ID NO. 45 is the polymerase II subunit *Sclerotinia sclerotiorum* partial rpb2 gene for RNA as used according to the subject invention.

SEQ ID NO. 46 is the ribosomal RNA gene *Puccinia hordei* 18S as used according to the subject invention.

SEQ ID NO. 47 is the hexose transporter (hxt2) gene *Sclerotinia sclerotiorum* as used according to the subject invention.

SEQ ID NO. 48 is *Fusarium solani pisi* cutinase mRNA as used according to the subject invention.

SEQ ID NO. 49 is the genome or conserved protein motif of *Phytophthora nicotianae* as used according to the subject invention.

SEQ ID NO. 50 is a ribosomal DNA sequence found in the *Phakopsora pachyrhizi* genome as used according to the subject invention.

SEQ ID NO. 51 is a *Fusarium sambucinum* translation elongation factor 1 alpha as used according to the subject invention.

SEQ ID NO. 52 is an elicitin gene sequence found in the *Phytophthora infestans* genome as used according to the subject invention.

SEQ ID NO. 53 is a partial rpb2 gene for RNA polymerase II subunit *Sclerotinia sclerotiorum* as used according to the subject invention.

SEQ ID NO. 54 is rRNA *Stenocarpella maydis* as used according to the subject invention.

SEQ ID NO. 55 is the 18S ribosomal RNA from a *Cercospora zeae-maydis* Group II as used according to the subject invention.

SEQ ID NO. 56 is Cathepsin B protease from *Myzus persicae* as used according to the subject invention.

SEQ ID NO. 57 is cysteine protease from *Leptinotarsa decemlineata* as used according to the subject invention.

SEQ ID NO. 58 is *Verticillium dahliae* rDNA as used according to the subject invention.

SEQ ID NO. 59 is partial sequence of 5.8S ribosomal RNA found in the *Peronospora berteroae* genome as used according to the subject invention.

SEQ ID NO. 60 is a genome subunit of cytochrome oxidase *Meloidogyne chitwoodi* as used according to the subject invention.

SEQ ID NO. 61 is ribosomal RNA *P. scribneri* as used according to the subject invention.

SEQ ID NO. 62 is ribosomal RNA *Heterodera glycines* as used according to the subject invention.

SEQ ID NO. 63 is RNA polymerase II sequence *Magnaporthe grisea* as used according to the subject invention.

SEQ ID NO. 64 is rRNA *Puccinia hordei* 18S as used according to the subject invention.

SEQ ID NO. 65 is the partial sequence 5.8S ribosomal RNA *Pseudoperonospora humuli* as used according to the subject invention.

SEQ ID NO. 66 is *Botrytis cinerea* cytochrome P450 monoxygenase as used according to the subject invention.

SEQ ID NO. 67 is rRNA *Pseudomonas syingae* as used according to the subject invention.

SEQ ID NO. 68 is *Clavibacter michiganensis michiganensis* Cel A gene as used according to the subject invention.

SEQ ID NO. 69 is *Clavibacter michiganensis* endo B-glucosidase gene as used according to the subject invention.

Definitions

As used herein, the following definitions apply:

Cell (or host plant cell) means a cell or protoplast of a plant cell and includes isolated cells and cells in a whole plant, plant organ, or fragment of a plant. It also includes non-isolated cells.

Double stranded region means a region of a polynucleotide wherein the nucleotides are capable of hydrogen bonding to each other. Such hydrogen bonding can be intramolecular or intermolecular (e.g. single transcription unit forming a double stranded region with the so-called hairpin or two transcription units that align appropriately for complementary sequences to hydrogen bond). To be a double stranded region, according to the present invention, it is not necessary for 100% of the nucleotides to be complementary and hydrogen bonded within a region. It is merely necessary for sufficient base pairing to occur to give the RNA a substantial double stranded character (e.g. an indicative melting point).

Exogenous gene means a gene that is not normally present in a given host genome in the present form. In this respect, the gene itself may be native to the host genome, however the exogenous gene will comprise the native gene altered by the addition or deletion of one or more different regulatory elements or additional genes.

Gene or genes means nucleic acid sequences (including both RNA or DNA) that encode genetic information for the synthesis of a whole RNA, a whole protein, or any functional portion of such whole RNA or whole protein sufficient to possess a desired characteristic.

Heterologous polynucleotide means any polynucleotide that is not found in a non-transformed host plant. A polynucleotide is not excluded from being a heterologous polynucleotide by the presence of endogenous polynucleotide sequences.

Homologous, in the context of the relationship between the antisense sequence and a pest pathogenicity gene (i.e. the DNA strand that binds RNA polymerase and directs transcription of the pest pathogenicity gene mRNA which is the antisense strand), means having sequence similarity sufficient to allow hybridization in vivo, in vitro, and/or ex vivo under low stringency conditions between the antisense sequence and the pest pathogenicity gene mRNA.

Host plant cell resistance means that a plant is less susceptible to the deleterious effects of a plant pest when compared to a host plant cell not transformed with said construct.

Inhibition of gene expression means a decrease in the level of protein and/or mRNA product from a target gene. The consequences of inhibition can be confirmed by examination of the outward properties of the cell or organism (as presented below in the examples) or by biochemical techniques such as RNA solution hybridization, nuclease protection, Northern hybridization, polymerase chain reaction (PCR), reverse transcription (RT) reverse transcription PCR(RT/PCR), gene expression monitoring with a microarray, antibody binding, enzyme linked immunosorbent assay (ELISA), Western blotting, radioimmunoassay (RIA), other immunoassays, and fluorescence activated cell analysis (FACS).

Marker gene means a gene that imparts a distinct phenotype to a cell expressing the marker gene and thus allows such transformed cells to be distinguished from cells that do not contain the gene.

Operably linked means joined as part of the same nucleic acid molecule, suitably positioned and oriented for transcription to be initiated from the promoter.

Pest pathogenicity gene means any pest gene that serves a role in such a pest's deleterious effects on a host plant. Deleterious effects means, by way of example, a negative effect on plant growth (numbers and/or size of the plant), development, quality, and/or reproduction. By way of example only, a pest pathogenicity gene may be one that serves a role in any of pest growth, development, replication and/or reproduction, or pest invasion or infection of the host plant.

Pathogenic, in reference to a pest, means a pest's ability to cause deleterious effects on a plant. Pathogenicity is augmented by any pest pathogenicity genes.

Plant pest means any living organism that is deleterious to plant growth (numbers and/or size of the plant), development, quality, yield, and/or reproduction. Non-limiting examples of such pests are insects, fungi, nematodes, bacteria, and viruses.

Quality means any aspect of a plant that can be considered desirable. By way of non-limiting example, quality can refer to a plant's appearance, yield, flavor, nutritional value, aroma, or content.

Substantially complementary, with respect to the sense and antisense sequences means sufficiently complementary to allow for formation of a double stranded molecule.

Transformation means a process of introducing an exogenous DNA sequence (e.g., a vector, a recombinant DNA molecule) into a cell or protoplast in which that exogenous DNA is incorporated into a chromosome or is capable of autonomous replication in a manner such that a heterologous RNA is transcribed.

Transcript means RNA encoded by DNA. In context of sense and antisense transcripts of the present invention, such sense and antisense transcripts can be part of the same polynucleotide or they can be 2 separate polynucleotides (i.e., each having its own 5' and 3' end).

Treating a plant pest means a method to reduce, eliminate, reverse, or prevent the deleterious effects of a plant pest on the plant.

Vector means a DNA molecule capable of replication in a host cell and/or to which another DNA segment can be operatively linked so as to bring about replication of the attached segment. A plasmid is an exemplary vector.

Underlying the various embodiments of the present invention is treating a plant to confer pest resistance by transforming a host plant cell with a heterologous polynucleotide comprising:

(a) an antisense sequence having homology to a pest pathogenicity gene, and (b) a sense sequence substantially complementary to said antisense sequence;

wherein said sense and antisense sequences are capable of hybridizing to each other to form a double-stranded region and wherein said sense and antisense sequences are each at least about 19 nucleotides in length.

Without being bound by theory, it is believed that plants transformed according to the present invention transcribe an RNA molecule(s) with a region homologous to and a region complementary to the pest pathogenicity gene, and wherein the transcript(s) form a double stranded RNA (dsRNA) molecule. The plant recognizes the dsRNA as a potential foreign substance (e.g. a substance of viral origin). The dicer enzyme of the plant cuts the double stranded RNA into pieces of single-stranded RNA of about 23 nucleotides in length, called small interfering RNAs (siRNAs). These siRNAs are consumed by invading pests that have entered the plant via the digestion of plant cells (e.g. cutin). Once absorbed, the siRNAs can be incorporated into the pest's RNA-induced silencing complexes (RISC). The RISC complex can then digest the mRNA of the pest's homologous gene limiting the pest's ability to harm the plant.

In one embodiment, pest resistance is conferred to a plant comprising the step of transforming a host plant cell with a heterologous polynucleotide, said heterologous polynucleotide comprising:

(a) an antisense sequence having homology to a pest pathogenicity gene, and (b) a sense sequence substantially complementary to said antisense sequence, wherein a transcript of the heterologous polynucleotide is capable of hybridizing to form a double-stranded region comprising nucleotides encoded by the antisense sequence and the sense sequence, wherein said sense and antisense sequences are each at least about 19 nucleotides in length, wherein said pest pathogenicity gene is selected from the group consisting of cutinases, kinases, ribosomal RNAs, adhesins, elicitins, and G-proteins; and wherein said pest is a fungus.

In one embodiment, pest resistance is conferred to a plant comprising the step of transforming a host plant cell with a heterologous polynucleotide, said heterologous polynucleotide comprising:

(a) an antisense sequence having homology to a pest pathogenicity gene; and (b) a sense sequence substantially complementary to said antisense sequence, wherein a transcript of the heterologous polynucleotide is capable of hybridizing to form a double-stranded region comprising nucleotides encoded by the antisense sequence and the sense sequence, wherein said sense and antisense sequences are each at least about 19 nucleotides in length, wherein said pest pathogenicity gene is selected from the group consisting of kinases, ribosomal RNAs, G-proteins, moulting factors, serine proteases, cysteine proteases, and juvenile hormone esterases; and wherein said pest is an insect.

In one embodiment, pest resistance is conferred to a plant comprising the step of transforming a host plant cell with a heterologous polynucleotide, said heterologous polynucleotide comprising:

(a) an antisense sequence having homology to a pest pathogenicity gene; and (b) a sense sequence substantially complementary to said antisense sequence, wherein a transcript of the heterologous polynucleotide is capable of hybridizing to form a double-stranded region comprising nucleotides encoded by the antisense sequence and the sense sequence, wherein said sense and antisense sequences are each at least about 19 nucleotides in length;

wherein said pest pathogenicity gene is selected from the group consisting of kinases, ribosomal RNAs, G-proteins, cuticle collagen proteins, and cathepsin proteases, and wherein said pest is a nematode.

In one embodiment, pest resistance is conferred to a plant comprising the step of transforming a host plant cell with a heterologous polynucleotide, said heterologous polynucleotide comprising:

(a) an antisense sequence having homology to a pest pathogenicity gene; and (b) a sense sequence substantially complementary to said antisense sequence, wherein a transcript of the heterologous polynucleotide is capable of hybridizing to form a double-stranded region comprising nucleotides encoded by the antisense sequence and the sense sequence, wherein said sense and antisense sequences are each at least about 19 nucleotides in length, wherein said pest pathogenicity gene is selected from the group consisting of cutinases, mascerating enzymes, kinases, ribosomal RNAs, adhesins, and G-proteins; and wherein said pest is a bacterium.

In one embodiment, the host plant is a soybean and the pest is one member selected from the group consisting of *Fusarium solani* (e.g., sudden death), *Sclerotinia sclerotiorum* (e.g., white mold), *Phialophora gregata* (e.g., brown stem rot), *Phakospora pachyrhizi* (e.g., Asian rust) and *Phytophthora sojae* (e.g., root and stem rot).

In one embodiment, the host plant is a cruciferous plant and the pest is *Alubgo* (e.g., white rust).

In one embodiment, the host plant is tobacco and the pest is *Phytophthora* (e.g., stem rot, root rot).

In one embodiment, the host plant is potato and the pest is *Phytophthora* (e.g., late blight).

In one embodiment, the host plant is broccoli and the is *Pythium* (e.g., damping-off).

In one embodiment, the host plant is pea and/or sugar beet and the pest is *Aphanomyces* (e.g., root rot).

In one embodiment, the host plant is tobacco and the pest is *Peronospora* (e.g., blue mold).

It has further been discovered that gene silencing in the pest according to the present invention, can be conferred upon the progeny of the pest—progeny that never had direct contact with the transformed host plant.

In one embodiment, the invention further comprises the step of cultivating a pest with the transformed host plant cell.

In one embodiment, a transformed host plant cell of the present invention is co-cultivated with a pest.

Optionally, progeny of the pest are less pathogenic to a plant cell other than the transformed host plant cell.

In one embodiment, a plant regenerated from a host plant cell transformed according to the present invention, is cultivated in soil contaminated with a pest.

In another embodiment, a plant regenerated from a host plant cell transformed according to the present invention, is cultivated in soil at risk of being contaminated with a pest.

In another embodiment, a pest is co-cultivated with a plant regenerated from a host plant cell transformed according to the present invention and then cultivated in soil contaminated with a pest.

In another embodiment, a pest is co-cultivated with a plant regenerated from a host plant cell transformed according to the present invention and then cultivated in soil at risk of being contaminated with a pest.

In one embodiment, a pest is co-cultivated with the transformed plant and then cultivated in soil at risk of being contaminated with a pest.

Pest Pathogenicity Gene Homology

It has been further discovered that gene silencing according to the present invention can confer resistance to a surprisingly broad range of pests and that exact identity between a region of the sense sequence and the pest infectious gene is not required for the present invention to be effective.

In one embodiment of the present invention, the pest pathogenicity gene is a gene that provides for cross-resistance. Such a pest gene is conserved within the pest phylum such that when used with the present invention, a plant is made resistant to a plurality of members of the pest phylum (i.e. cross-resistance). Moreover, pest pathogenicity genes can be chosen according to the present invention by bioinformatic homology analysis as known to those skilled in the art to provide cross-resistance that is cross-species, cross-genus, cross-family, or cross-order resistance. For example, as will become clear from the examples herein, a cutinase gene is useful in plants to confer resistance to a plurality of fungi species. The gene for rDNA is useful in the pests of the present invention (i.e. insects, bacteria, fungi, and nematodes). Other non-limiting examples of such conserved genes are kinases, adhesions, G-proteins, elicitins, macerating enzymes, DNA and RNA polymerases, elongation factors, moulting factors, serine proteases, cysteine proteases, juvenile hormone esterase, cuticle collagen proteins, and cathepsin proteases and others set forth below. In another embodiment, a pest pathogenicity gene is selected to lack sufficient homology with a plant gene to cause harmful effects of the heterologous polynucleotide on the host plant (e.g. prevent silencing of a plant gene). For example, in one embodiment, the homology between the antisense sequence and the pest pathogenicity gene is less than about 70%.

In one embodiment, the antisense sequence is homologous to the pest pathogenicity gene by at least about 70%.

Optionally, the homology is at least about 75%.

Optionally, the homology is at least about 80%.

Optionally, the homology is at least about 85%.

Optionally, the homology is at least about 90%.

Optionally, the homology is at least about 95%.

In one embodiment, a transcript of the sense sequence is homologous to a transcript of the pest pathogenicity gene (e.g. pest pathogenicity gene mRNA) by at least about 70%.

Optionally, the homology is at least about 75%.

Optionally, the homology is at least about 80%.

Optionally, the homology is at least about 85%.

Optionally, the homology is at least about 90%.

Optionally, the homology is at least about 95%.

The above-mentioned homology can optionally extend over a stretch of at least about 20 nucleotides, or at least about 25 nucleotides, or at least about 50 nucleotides, or at least about 100 nucleotides.

Optionally, homology can be demonstrated between the antisense sequence and the pest pathogenicity gene (i.e. the DNA strand that binds RNA polymerase and directs transcription of the pest pathogenicity gene mRNA) in any of at least three ways.

(1) hybridization between the antisense sequence and corresponding region of the pest gene sense strand.

(2) hybridization between the antisense transcript and the corresponding region of the pest pathogenicity gene.

(3) hybridization between a transcript of a DNA complentary to the antisense sequence (i.e. antisense cDNA) and a corresponding region of the pest pathogenicity gene mRNA.

Hybridization, as set forth above, can be demonstrated under conditions of low stringency. Optionally, the conditions are ones of moderate to high stringency by techniques well known in the art, as described, for example, in Keller, G. H., M. M. Manak (1987) DNA Probes, Stockton Press, New York, N.Y., pp. 169-170.

Examples of moderate to high stringency conditions are provided herein. Specifically, hybridization of immobilized DNA on Northern blots with 32P-labeled gene-specific probes is performed using standard methods (Maniatis et al.). In general, hybridization and subsequent washes are carried out under moderate to high stringency conditions that allowed for detection of target sequences with homology to sequences exemplified herein. For double-stranded DNA gene probes, hybridization was carried out overnight at 20-25° C. below the melting temperature (Tm) of the DNA hybrid in 6×SSPE, 5×Denhardt's solution, 0.1% SDS, 0.1 mg/ml denatured DNA. The melting temperature is described by the following formula from Beltz et al. (1983): Tm=81.5° C.+16.6 Log $[Na^+]$+0.41(% G+C)−0.61(% formamide)-600/length of duplex in base pairs.

Washes are typically carried out as follows:

(1) Twice at room temperature for 15 minutes in 1×SSPE, 0.1% SDS (low stringency wash).

(2) Once at Tm-20° C. for 15 minutes in 0.2×SSPE, 0.1% SDS (moderate stringency wash).

For oligonucleotide probes, hybridization was carried out overnight at 10-20° C. below the melting temperature (Tm) of the hybrid in 6×SSPE, 5×Denhardt's solution, 0.1% SDS, 0.1 mg/ml denatured DNA. Tm for oligonucleotide probes was determined by the following formula from Suggs et al. (1981): Tm (° C.)=2(number T/A base pairs)+4(number G/C base pairs).

Washes were typically carried out as follows:

(1) Twice at room temperature for 15 minutes 1×SSPE, 0.1% SDS (low stringency wash).

(2) Once at the hybridization temperature for 15 minutes in 1×SSPE, 0.1% SDS (moderate stringency wash).

In general, salt and/or temperature can be altered to change stringency. With a labeled DNA fragment of greater than about 70 or so bases in length, the following conditions can be used:

Low: 1 or 2×SSPE, room temperature

Low: 1 or 2×SSPE, 42° C.

Moderate: 0.2× or 1×SSPE, 65° C.

High: 0.1×SSPE, 65° C.

Duplex formation and stability depend on substantial complementarity between the two strands of a hybrid, and, as noted above, a certain degree of mismatch can be tolerated. Therefore, polynucleotide sequences useful in the subject invention include mutations (both single and multiple), deletions, and insertions in the described sequences, and combinations thereof, wherein said mutations, insertions, and deletions permit formation of stable hybrids with a target polynucleotide of interest. Mutations, insertions, and deletions can be produced in a given polynucleotide sequence using standard methods known in the art. Other methods may become known in the future.

The mutational, insertional, and deletional variants of the polynucleotide sequences of the invention can be used in the same manner as the exemplified polynucleotide sequences so long as the variants have substantial sequence similarity with the original sequence. As used herein, substantial sequence similarity refers to the extent of nucleotide similarity that is sufficient to enable the variant polynucleotide to function in the same capacity as the original sequence. Preferably, this similarity is greater than 75%; more preferably, this similarity is greater than 90%; and most preferably, this similarity is greater than 95%. The degree of similarity needed for the variant to function in its intended capacity will depend upon the intended use of the sequence. It is well within the skill of a person trained in this art to make mutational, insertional, and deletional mutations that are designed to improve the function of the sequence or otherwise provide a methodological advantage.

Vectors

Those skilled in the art are well able to construct vectors of the present invention (including those based on naked DNA) and design protocols for recombinant gene expression. For further details see, for example, Molecular Cloning: a Laboratory Manual: 2nd edition, Sambrook et al, 1989, Cold Spring Harbor Laboratory Press. Such applicable techniques and protocols for manipulation of nucleic acid, for example in preparation of nucleic acid constructs, mutagenesis, sequencing, introduction of DNA into cells and gene expression, and analysis of proteins, are described in detail in Protocols in Molecular Biology, Second Edition, Ausubel et al. eds., John Wiley & Sons, 1992.

Specific procedures and vectors previously used with wide success upon plants are described by Bevan, Nucl. Acids Res. (1984) 12, 8711-8721), and Guerineau and Mullineaux, (1993). Plant transformation and expression vectors. In: Plant Molecular Biology Labfax (Croy RRD ed). Oxford, BIOS Scientific Publishers, pp 121-148.

Vectors according to the present invention may be provided isolated and/or purified (i.e. from their natural environment), in substantially pure or homogeneous form, or free or substantially free of other nucleic acid. Nucleic acid according to the present invention may be wholly or partially synthetic.

Host Plants

The present invention may be used for transformation of any plant, including, but not limited to, corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassaya (*Manihot esculenta*), coffee (*Cofea* ssp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidental*), *macadamia* (*Macadamia integrifolia*), almond (*Prunus amygdalus*), sugar beets (*Beta vulgaris*), oats, barley, vegetables, ornamentals, and conifers.

Optionally, plants of the present invention are crop plants (for example, cereals and pulses, maize, wheat, potatoes, tapioca, rice, sorghum, millet, cassaya, barley, pea, and other root, tuber, or seed crops. Important seed crops for the present invention are oil-seed rape, sugar beet, maize, sunflower, soybean, and sorghum. Horticultural plants to which the present invention may be applied may include lettuce, endive, and vegetable brassicas including cabbage, broccoli, and cauliflower, and carnations, geraniums, petunias, and begonias. The present invention may be applied to tobacco, cucurbits, carrot, strawberry, sunflower, tomato, pepper, chrysanthemum, poplar, eucalyptus, and pine.

Optionally, plants of the present invention include grain seeds, such as corn, wheat, barley, rice, sorghum, rye, etc.

Optionally, plants of the present invention include oil-seed plants. Oil seed plants include canola, cotton, soybean, safflower, sunflower, *Brassica*, maize, alfalfa, palm, coconut, etc.

Optionally, plants of the present invention include leguminous plants. Leguminous plants include beans and peas. Beans include guar, locust bean, fenugreek, soybean, garden beans, cowpea, mung bean, lima bean, fava bean, lentils, chickpea, etc.

Host plants useful in the present invention are row crops and broadcast crops. Non limiting examples of useful row crops are corn, soybeans, cotton, amaranth, vegetables, rice, sorghum, wheat, milo, barley, sunflower, durum, and oats.

Non-limiting examples of useful broadcast crops are sunflower, millet, rice, sorghum, wheat, milo, barley, durum, and oats.

Host plants useful in the present invention are monocots and dicots.

Non-limiting examples of useful monocots are rice, corn, wheat, palm trees, turf grasses, barley, and oats.

Non-limiting examples of useful dicots are soybean, cotton, alfalfa, canola, flax, tomato, sugar beet, sunflower, potato, tobacco, corn, wheat, rice, lettuce, celery, cucumber, carrot, cauliflower, grape, and turf grasses.

Host plants useful in the present invention include plants cultivated for aesthetic or olfactory benefits. Non limiting examples include flowering plants, trees, grasses, shade plants, and flowering and non-flowering ornamental plants.

Host plants useful in the present invention include plants cultivated for nutritional value.

Host Cell Types

One skilled in the art will recognize the wide variety of host cells that can be contacted with the heterologous polynucleotides according to the present invention. Non-limiting examples of such cells are those in embryogenic tissue, callus tissue types I, II, and III, hypocotyl, meristem, root tissue, tissues for expression in phloem, and the like.

Host plant cells can optionally be enriched for cells with a higher potential to be transformed and/or a higher potential to regenerate mature plants. Manual selection of host plant cells, e.g., by selecting embryogenic cells from the surface of a Type II callus, is one means that may be used to enrich for host plant cells prior to culturing (whether cultured on solid media or in suspension). Optionally, cells can be selected from those located at the surface of a cell cluster, and may further be identifiable by their lack of differentiation, their size and dense cytoplasm. In one embodiment, host plant cells are less differentiated, or not yet committed to differentiation. Thus, in one embodiment, cells are identified and selected from those cells which are cytoplasmically dense, relatively unvacuolated with a high nucleus to cytoplasm ratio (e.g., determined by cytological observations), small in size (e.g., 10-20 μm), and capable of sustained divisions and somatic proembryo formation.

Optionally, host plant cells are identified through the use of dyes, such as Evan's blue, which are excluded by cells with relatively non-permeable membranes, such as embryogenic cells, and taken up by relatively differentiated cells such as root-like cells and snake cells (so-called due to their snake-like appearance).

Optionally, host plant cells are identified through the use of isozyme markers of embryogenic cells, such as glutamate dehydrogenase, which can be detected by cytochemical stains (Fransz et al., 1989). One skilled in the art will recognize that isozyme markers such as glutamate dehydrogenase may lead to some degree of false positives from non-embryogenic cells such as rooty cells which nonetheless have a relatively high metabolic activity.

Almost all plant tissues may be transformed during dedifferentiation using appropriate techniques described herein. Recipient cell targets include, but are not limited to, meristem cells, Type I, Type II, and Type III callus, immature embryos and gametic cells such as microspores, pollen, sperm, and egg cells. It is contemplated that any cell from which a fertile plant may be regenerated is useful as a recipient cell. Type I, Type II, and Type III callus may be initiated from tissue sources including, but not limited to, immature embryos, immature inflorescenses, seedling apical meristems, microspores, and the like.

Those cells that are capable of proliferating as callus also are recipient cells for genetic transformation. The present invention provides techniques for transforming immature embryos and subsequent regeneration of fertile transgenic plants. Direct transformation of immature embryos obviates the need for long term development of recipient cell cultures. Pollen, as well as its precursor cells, microspores, may be capable of functioning as recipient cells for genetic transformation, or as vectors to carry foreign DNA for incorporation during fertilization. Direct pollen transformation would obviate the need for cell culture.

Meristematic cells (i.e., plant cells capable of continual cell division and characterized by an undifferentiated cytological appearance, normally found at growing points or tissues in plants such as root tips, stem apices, lateral buds, etc.) may represent another type of recipient plant cell. Because of their undifferentiated growth and capacity for organ differentiation and totipotency, a single transformed meristematic cell could be recovered as a whole transformed plant. In fact, it is proposed that embryogenic suspension cultures may be an in vitro meristematic cell system, retaining an ability for continued cell division in an undifferentiated state, controlled by the media environment.

Pests

Plant pests useful in the present invention (i.e., can be rendered non-pathogenic according to the present invention), include fungi, nematodes, insects, bacteria, and parasitic plants such as striga, dodder and mistletoe.

Non-limiting examples of useful fungi include those set forth in Table 4.

Non-limiting examples of such useful nematodes include those set forth in Table 3.

Non-limiting examples of such useful insects include aphids, leafhoppers, planthoppers, mealy bugs, and Lepidoptera larvae.

Plant pests usefully treated by the present invention include bacteria. Non-limiting examples of such bacteria are shown in Table 1.

Plant pests usefully treated by the present invention includes rusts. Non-limiting examples of such rust are shown in Table 5.

Plant pests usefully treated by the present invention include the downy mildews. Non-limiting examples of such are shown in Table 2.

TABLE 1

| Pests - Bacteria | |
|---|---|
| Disease | Causative Agent |
| Bacterial leaf blight and stalk rot | *Pseudomonas avenae* subsp. *avenae* |
| Bacterial leaf spot | *Xanthomonas campestris* pv. *holcicola* |
| Bacterial stalk rot | *Enterobacter dissolvens* = *Erwinia dissolvens* |
| Bacterial stalk and top rot | *Erwinia carotovora* subsp. *carotovora*, *Erwinia chrysanthemi* pv. *Zeae* |
| Bacterial stripe | *Pseudomonas andropogonis* |
| Chocolate spot | *Pseudomonas syringae* pv. *Coronafaciens* |
| Goss's bacterial wilt and blight(leaf freckles and wilt) | *Clavibacter michiganensis* subsp. *nebraskensis* = *Corynebacterium michiganense* pv. *Nebraskense* |
| Holcus spot | *Pseudomonas syringae* pv. *Syringae* |
| Purple leaf sheath | Hemiparasitic bacteria + (See under Fungi) |
| Seed rot-seedling blight | *Bacillus subtilis* |
| Stewart's disease (bacterial wilt) | *Pantoea stewartii* = *Erwinia stewartii* |
| Corn stunt (Mesa Central or Rio Grande stunt) | achapparramiento, stunt, *Spiroplasma kunkelii* |

TABLE 2

| Pests - Downy Mildews | |
|---|---|
| Disease | Causative Agent |
| Brown stripe downy mildew | *Sclerophthora rayssiae* var. *zeae* |
| Crazy top downy mildew | *Sclerophthora macrospora* = *S. macrospore* |
| Green ear downy mildew | *Sclerospora graminicola* |
| Java downy mildew | *Peronosclerospora maydis* = *Sclerospora maydis* |
| Philippine downy mildew | *Peronosclerospora philippinensis* = *Sclerospora philippinensis* |
| *Sorghum* downy mildew | *Peronosclerospora sorghi* = *Sclerospora sorghi* |
| *Spontaneum* downy mildew | *Peronosclerospora spontanea* = *Sclerospora spontanea* |
| Sugarcane downy mildew | *Peronosclerospora sacchari* = *Sclerospora sacchari* |
| Dry ear rot (cob, kernel and stalk rot) | *Nigrospora oryzae* (teleomorph: *Khuskia oryzae*) |
| Ear rots, minor | *Aspergillus glaucus*, *A. niger*, *Aspergillus* spp., *Cunninghamella* sp., *Curvularia pallescens*, *Doratomyces stemonitis* = *Cephalotrichum stemonitis*, *Fusarium culmorum*, *Gonatobotrys simplex*, *Pithomyces maydicus*, *Rhizopus microsporus*, *R. stolonifer* = *R. nigricans*, *Scopulariopsis brumptii* |
| Ergot (horse's tooth, diente del caballo) | *Claviceps gigantea* (anamorph: *Sphacelia* sp.) |
| Eyespot | *Aureobasidium zeae* = *Kabatiella zeae* |
| *Fusarium* ear and stalk rot | *Fusarium subglutinans* = *F. moniliforme* var. *subglutinans* |
| *Fusarium* kernel, root and stalk rot, seed rot and seedling blight | *Fusarium moniliforme* teleomorph: *Gibberella fujikuroi*) |
| *Fusarium* stalk rot, seedling root rot | *Fusarium avenaceum* (teleomorph: *Gibberella avenacea*) |
| *Gibberella* ear and stalk rot | *Gibberella zeae* (anamorph: *Fusarium graminearum*) |
| Gray ear rot | *Botryosphaeria zeae* = *Physalospora zeae* (anamorph: *Macrophoma zeae*) |
| Gray leaf spot | *Cercospora* leaf spot) *Cercospora sorghi* = *C. sorghi* var. *maydis*, *C. zeae-maydis* |
| *Helminthosporium* root rot | *Exserohilum pedicellatum* = *Helminthosporium pedicellatum* (teleomorph: *Setosphaeria* |
| *Hormodendrum* ear rot | (*Cladosporium Cladosporium cladosporioides* = *Hormodendrum cladosporioides*, rot), *C. herbarum* (teleomorph: *Mycosphaerella tassiana*) |
| *Hyalothyridium* leaf spot | *Hyalothyridium maydis* |
| Late wilt | *Cephalosporium maydis* |
| Leaf spots, minor | *Alternaria alternata*, *Ascochyta maydis*, *A. tritici*, *A. zeicola*, *Bipolaris victoriae* = *Helminthosporium victoriae* (teleomorph: *Cochliobolus victoriae*), *C. sativus* (anamorph: *Bipolaris sorokiniana* = *H. sorokinianum* =*H. sativum*), *Epicoccum nigrum*, *Exserohilum prolatum* = *Drechslera prolata* (teleomorph: *Setosphaeria prolata*) *Graphium penicillioides*, *Leptosphaeria maydis*, *Leptothyrium zeae*, *Ophiosphaerella herpotricha*, |

TABLE 2-continued

| Pests - Downy Mildews | |
|---|---|
| Disease | Causative Agent |
| | (anamorph: *Scolecosporiella* sp.), *Paraphaeosphaeria michotii*, *Phoma* sp., *Septoria zeae*, *S. zeicola*, *S. zeina* |
| Northern corn leaf blight | *Exserohilum turcicum* = *Helminthosporium turcicum*, *Setosphaeria turcica* |
| Northern corn leaf spot | *Cochliobolus carbonum* |
| *Helminthosporium* ear rot (race 1) | *Bipolaris zeicola* = *Helminthosporium carbonum* |
| *Penicillium* ear rot (blue eye, blue mold) | *Penicillium* spp., *P. chrysogenum*, *P. expansum*, *P. oxalicum* |
| *Phaeocytostroma* stalk rot and root rot | *Phaeocytostroma ambiguum*, *Phaeocytosporella zeae* |
| *Phaeosphaeria* leaf spot | *Phaeosphaeria maydis*, *Sphaerulina maydis* |
| *Physalospora* ear rot | *Botryosphaeria Botryosphaeria festucae* = *Physalospora zeicola*, (anamorph: *Diplodia frumenti*) |
| Purple leaf sheath | Hemiparasitic bacteria and fungi |
| *Pyrenochaeta* stalk rot and root rot | *Phoma terrestris*, *Pyrenochaeta terrestris* |
| *Pythium* root rot | *Pythium* spp., *P. arrhenomanes*, *P. graminicola* |
| *Pythium* stalk rot | *Pythium aphanidermatum* = *P. butleri L.* |
| Red kernel disease (ear mold, leaf and seed rot) | *Epicoccum nigrum* |
| *Rhizoctonia* ear rot | *Rhizoctonia zeae* (teleomorph: *Waitea circinata*) |
| *Rhizoctonia* root rot and stalk rot | *Rhizoctonia solani*, *Rhizoctonia zeae* |
| Root rots, minor | *Alternaria alternata*, *Cercospora sorghi*, *Dictochaeta fertilis*, *Fusarium acuminatum* (teleomorph: *Gibberella acuminata*), *F. equiseti* (teleomorph: *G. intricans*), *F. oxysporum*, *F. pallidoroseum*, *F. poae*, *F. roseum*, *F. cyanogena*, (anamorph: *F. sulphureum*), *Microdochium bolleyi*, *Mucor* sp., *Periconia circinata*, *Phytophthora cactorum*, *P. drechsleri*, *P. nicotianae* var. *parasitica*, *Rhizopus arrhizus* |
| *Rostratum* leaf spot (leaf disease, ear and stalk rot) | *Setosphaeria rostrata*, *Helminthosporium* (anamorph: *Exserohilum rostratum* = *Helminthosporium rostratum*) |
| Rust, common corn | *Puccinia sorghi* |
| Rust, southern corn | *Puccinia polysora* |
| Rust, tropical corn | *Physopella pallescens*, *P. zeae* = *Angiopsora zeae* |
| *Sclerotium* ear rot (southern blight) | *Sclerotium rolfsii* (teleomorph: *Athelia rolfsii*) |
| Seed rot-seedling blight | *Bipolaris sorokiniana*, *B. zeicola* = *Helminthosporium carbonum*, *Diplodia maydis*, *Exserohilum pedicillatum*, *Exserohilum turcicum* = *Helminthosporium turcicum*, *Fusarium avenaceum*, *F. culmorum*, *F. moniliforme*, *Gibberella zeae* (anamorph: *F. graminearum*), *Macrophomina phaseolina*, *Penicillium* spp., *Phomopsis* sp., *Pythium* spp., *Rhizoctonia solani*, *R. zeae*, *Sclerotium rolfsii*, *Spicaria* sp. |
| *Selenophoma* leaf spot | *Selenophoma* sp. |
| Sheath rot | *Gaeumannomyces graminis* |
| Shuck rot | *Myrothecium gramineum* |
| Silage mold | *Monascus purpureus*, *M. rubber* |
| Smut, common | *Ustilago zeae* = *U. maydis* |
| Smut, false | *Ustilaginoidea virens* |
| Smut, head | *Sphacelotheca reiliana* = *Sporisorium holci-sorghi* |
| Southern corn leaf blight and stalk rot | *Cochliobolus heterostrophus* (anamorph: *Bipolaris maydis* = *Helminthosporium maydis*) |
| Southern leaf spot | *Stenocarpella macrospora* = *Diplodia macrospora* |
| Stalk rots, minor | *Cercospora sorghi*, *Fusarium episphaeria*, *F. merismoides*, *F. oxysporum*, *F. poae*, *F. roseum*, *F. solani* (teleomorph: *Nectria haematococca*), *F. tricinctum*, *Mariannaea elegans*, *Mucor* sp., *Rhopographus zeae*, *Spicaria* sp. |
| Storage rots | *Aspergillus* spp., *Penicillium* spp. and other fungi |
| Tar spot | *Phyllachora maydis* |
| *Trichoderma* ear rot and root rot | *Trichoderma viride* = *T. lignorum* teleomorph: *Hypocrea* sp. |
| White ear rot, root and stalk rot | *Stenocarpella maydis* = *Diplodia zeae* |
| Yellow leaf blight | *Ascochyta ischaemi*, *Phyllosticta maydis* (teleomorph: *Mycosphaerella zeae-maydis*) |
| Zonate leaf spot | *Gloeccercospora sorghi* |

TABLE 3

| Pests - Parasitic Nematodes | |
|---|---|
| Disease | Pathogen |
| Awl | *Dolichodorus* spp., *D. heterocephalus* |
| Bulb and stem (Europe) | *Ditylenchus dipsaci* |
| Burrowing | *Radopholus similes* |
| Cyst | *Heterodera avenae*, *H. zeae*, *Punctodera chalcoensis* |
| Dagger | *Xiphinema* spp., *X. americanum*, *X. Mediterraneum* |
| False root-knot | *Nacobbus dorsalis* |
| Lance, Columbia | *Hoplolaimus Columbus* |
| Lance | *Hoplolaimus* spp., *H. galeatus* |
| Lesion | *Pratylenchus* spp., *P. brachyurus*, *P. crenatus*, *P. hexincisus*, *P. neglectus*, *P. penetrans*, *P. scribneri*, *P. thornei*, *P. zeae* |
| Needle | *Longidorus* spp., *L. breviannulatus* |
| Ring | *Criconemella* spp., *C. ornata* |
| Root-knot | *Meloidogyne* spp., *M. chitwoodi*, *M. incognita*, *M. javanica* |
| Spiral | *Helicotylenchus* spp. |
| Sting | *Belonolaimus* spp., *B. longicaudatus* |
| Stubby-root | *Paratrichodorus* spp., *P. christiei*, *P. minor*, *Quinisulcius acutus*, *Trichodorus* spp. |
| Stunt | *Tylenchorhynchus dubius* |

TABLE 4

| Pests - Fungal | |
|---|---|
| Disease | Fungal Pest |
| Anthracnose leaf blight and anthracnose stalk rot | *Colletotrichum graminicola* (teleomorph: *Glomerella graminicola*), *Glomerella tucumanensis* (anamorph: *Glomerella falcatum*) |
| *Aspergillus* ear and kernel rot | *Aspergillus flavus* |
| Banded leaf and sheath spot | *Rhizoctonia solani* = *Rhizoctonia microsclerotia* (teleomorph: *Thanatephorus cucumeris*) |
| Black bundle disease | *Acremonium strictum* = *Cephalosporium acremonium* |
| Black kernel rot | *Lasiodiplodia theobromae* = *Botryodiplodia theobromae* |
| Borde blanco | *Marasmiellus* sp. |
| Brown spot (black spot, stalk rot) | *Physoderma maydis* |
| *Cephalosporium* kernel rot | *Acremonium strictum* = *Cephalosporium acremonium* |
| Charcoal rot | *Macrophomina phaseolina* |
| *Corticium* ear rot | *Thanatephorus cucumeris* = *Corticium sasakii* |
| *Curvularia* leaf spot | *Curvularia clavata*, *C. eragrostidis*, = *C. maculans* (teleomorph: *Cochliobolus eragrostidis*), *Curvularia inaequalis*, *C. intermedia* (teleomorph: *Cochliobolus intermedius*), *Curvularia lunata* (teleomorph: *Cochliobolus lunatus*), *Curvularia pallescens* (teleomorph: *Cochliobolus pallescens*), *Curvularia senegalensis*, *C. tuberculata* (teleomorph: *Cochliobolus tuberculatus*) |
| *Didymella* leaf spot | *Didymella exitalis* |
| *Diplodia* ear rot and stalk rot | *Diplodia frumenti* (teleomorph: *Botryosphaeria festucae*) |
| *Diplodia* ear rot, stalk rot, seed rot and seedling blight | *Diplodia maydis* = *Stenocarpella maydis* |
| *Diplodia* leaf spot or leaf streak | *Stenocarpella macrospora* = *Diplodia macrospore* |

TABLE 5

| Pests - Rusts | | |
|---|---|---|
| Host plant | Common disease name | Rust Species |
| Barley | Crown rust | *Puccinia coronate* |
| | Leaf rust | *Puccinia hordei* |
| | Stem rust | *Puccinia graminis* |
| | Stripe (yellow) rust | *Puccinia striiformis* |
| Corn | Common rust | *Puccinia sorghi* |
| | Southern rust | *Puccinia polysora* |
| | Tropical rust | *Physopella pallescens*, *P. zeae* = *Angiopsora zeae* |
| Oats | Crown rust | *Puccinia coronata* |
| | Stem Rust | *Puccinia graminis* |
| Rye | Stem rust | *Puccinia gramminis*. = *P. graminis f.* sp. *secalis* |
| | Leaf (brown) rust | *Puccinia recondita* (anamorph: *Aecidium clematidis*) |
| *Sorghum* | Rust | *Puccinia purpurea* |
| Sugarcane | Common Rust | *Puccinia melanocephala*. = *P. erianthi* |
| | Orange Rust | *Puccinia kuehnii* |
| Wheat | Leaf (brown) rust | *Puccinia triticina*. = *P. Recondita f.* Sp. *tritici* = *P. tritici-duri* |
| | Stem (black) rust | *Puccinia gramminis* = *P. graminis f.* sp. *tritici* |
| | Stripe (yellow) rust | *Puccinia striiformis* (anamorph: *P. uredoglumarum*) |
| Apple | American hawthorne rust | *Gymnosporangium globosum* |
| | Cedar apple rust | *Gymnosporangium juniperi-virginianae* |
| | Japanese apple rust | *Gymnosporangium yamadae miyabe* ex *yamada* |
| | Pacific Coast pear rust | *Gymnosporangium libocedri* |
| | Quince rust | *Gymnosporangium clavipes* |
| Asparagus | Rust | *Puccinia asparagi* |
| Banana | Leaf rust | *Uredo musae*, *uromyces musae* |
| Bean | Rust | *Uromyces appendiculatus* |

TABLE 5-continued

| Pests - Rusts | | |
|---|---|---|
| Host plant | Common disease name | Rust Species |
| Beet | Seedling rust. | *Puccinia subnitens* |
| Carrot | Rust | *Aecidium foeniculiuromyces graminis*, *Uromyces lineolatus* subsp. *nearcticus* |
| Chickpea | Rust | *Uromyces ciceris-arietini*, *Uromyces striatus* |
| Coffee | Rust (orange or leaf rust) | *Hemileia vastatrix* |
| | Rust (powdery or grey rust) | *Hemileia coffeicola* |
| Cotton | Cotton rust | *Puccinia schedonnardi* |
| | Southwestern rust | *Puccinia cacabata* |
| | Tropical rust | *Phakopsora gossypii* |
| *Eucalyptus* | rust | *Puccini apsidii* |
| Flax | Rust | *Melampsora lini* |
| Crape | Rust | *Physopella ampelopsidis* |
| Lettuce | Rust | *Puccinia dioicae* = *P. extensicola* var. *hieraciata* |
| Asparagus | Asparagus rust | *Puccinia asparagi* |
| Onion | Onion rust | *Puccinia allii* |
| Pea | Rust | *Uromyces fabae* |
| peanut | Rust | *Puccinia arachidis* |
| Pear | American hawthome rust | *Gymnosporangium globosum* |
| | Kern's pear rust | *Gymnosporangium kernianum* |
| | Pacific Coast pear rust | *Gymnosporangium libocedri* |
| | Pear trellis rust | *Gymnosporangium fuscum* |
| | Rocky Mountain pear rust | *Gymnosporangium nelsonii* |
| Poplar | European Poplar rust | *Melampsora larici-populinakle* |
| | American leaf rust | *Melampsora medusae* |
| Potato | Common rust | *Puccinia pittierianap* |
| | Deforming rust | *Aecidium cantensis* |
| Red clover | Rust | *Uromyces trifolii-repentis* |
| Soybean | Rust | *Phakopsora pachyrhizi* |
| Strawberry | Leaf rust | *Phragmidium potentillae* = *Frommea obtusa* |
| Sunflower | Rust | *Puccinia helianthi*, *P. xanthii*, *Uromyces junci* |
| Sweet potato | Red rust | *Coleosporium ipomoeae* |

Pest Pathogenicity Genes

The skilled artisan can readily identify pest genes to target in the present invention. Such a gene could be any pest gene that serves a direct or indirect role in such a pest's deleterious effects on a host plant. By way of example only, such a gene may be one that serves a role in pest growth, development, replication and reproduction, and invasion or infection.

In one embodiment, the host plant does not contain a gene that is more than about 70% homologous to the pest pathogenicity gene.

Optionally, the homology is not more than about 60%.

Optionally, the homology is not more than about 50%.

In one embodiment, the host plant does not contain a gene that contains a 25 nucleotide stretch that is more than about 70% homologous to the pest pathogenicity gene.

In one embodiment, the host plant does not contain a gene that contains a 25 nucleotide stretch that is more than about 60% homologous to the pest pathogenicity gene.

In one embodiment, the host plant does not contain a gene that contains a 25 nucleotide stretch that is more than about 50% homologous to the pest pathogenicity gene.

In one embodiment, the host plant does not contain more than one gene that contains a nucleotide stretch that is more than about 70% homologous to the pest pathogenicity gene.

In one embodiment, the host plant does not contain more than one gene that contains a 25 nucleotide stretch that is more than about 60% homologous to the pest pathogenicity gene.

In one embodiment, the host plant does not contain more than one gene that contains a 25 nucleotide stretch that is more than about 50% homologous to the pest pathogenicity gene.

TABLE 6

| Pests, Pest pathogenicity genes, and Host Plants | | |
|---|---|---|
| Pest or pathogen group | Pest pathogenicity gene | Host Plants |
| Fungi | Cutinases | All |
| | Kinases | All |
| | Ribosomal RNAs | All |
| | Adhesins | All |
| | G-proteins | All |
| | Elicitins | All |
| Bacteria | Cutinases | All |
| | Mascerating enzymes | All |
| | Kinases | All |
| | Ribosomal RNAs | All |
| | Adhesins | All |
| | G-proteins | All |
| Insects | Kinases | All |
| | Ribosomal RNAs | All |
| | G-proteins | All |
| | Moulting factors | All |
| | Serine proteases | All |
| | Cysteine proteases | All |
| | Juvenile hormone esterase | All |
| Nematodes | Kinases | All |
| | Ribosomal RNAs | All |
| | G-proteins | All |
| | Cuticle collagen proteins | All |
| | Cathepsin proteases | All |

By way of example, cutinase is a gene useful according to the present invention. When a fungal hypha invades a plant cell and absorbs nutrients, it absorbs the siRNAs from the plant and silences the fungus' essential and constitutive cutinase.

By way of example only, such a gene may be one that serves a role in pest growth, development, replication and reproduction, and invasion or infection. Other non limiting examples include those in Table 6.

Sense (and Antisense) Sequences

Sense and antisense sequences according to the present invention can be any sequence with homology to a sense and antisense strand (respectively) of pest pathogenicity gene.

The sense and antisense sequences can be on the same DNA strand or on different DNA strands. When the sense and antisense sequences are on the same DNA strand, transcription of these sequences can be driven off the same promoter or off of different promoters (e.g. different copies of the same promoter or different promoter). When the sense and antisense sequences are on different DNA strands, transcription of these sequences is driven off of different promoters.

The sense and antisense sequences can be arranged in DNA as complementary, duplex DNA or the sequences can be in different regions of the DNA (i.e. not forming duplex DNA with each other).

Each of the sense and antisense sequences comprise at least about 19 nucleotides. Optionally, each sequence comprises at least about 50 nucleotides, optionally at least about 100 nucleotides, optionally at least about 150 nucleotides, optionally at least about 250 polynucleotides, optionally at least about 500 nucleotides, optionally at least about 600 polynucleotides.

In one embodiment, the sequences are modified from the pest pathogenicity gene to create or increase homology to the pathogenicity gene of more than one pest.

In another embodiment the sequences are modified from the pest pathogenicity gene to shorten an open reading frame.

In another embodiment the sequences are modified from the pest pathogenicity gene to result in less homology with a plant, animal, or human gene.

In another embodiment, sense and antisense sequences comprise duplicative regions of a pest pathogenicity gene. Selection of such regions is made according to the teachings of the invention herein (e.g. highly conserved regions).

In other embodiments, regions of a pest pathogenicity gene or even the entire coding region of a pest pathogenicity gene may be duplicated to comprise sense and antisense sequences to increase the length of the double stranded region formed by the sense and antisense sequences. While not bound by theory, it is believed that in some embodiments of the present invention, a threshold level of siRNA's must be formed to elicit useful gene silencing in the pest and to confer pest resistance to the plant. Duplication of gene sequences is one useful way of increasing the length of the double stranded region and increasing the number of siRNA.

This (gene duplication) approach is demonstrated in examples herein using the heterologous polynucleotide pVZA300 (SEQ ID 7) comprising the elicitin INF1 of *Phytophthora infestans* (GenBank locus AY766228). This sequence was selected because of its high homology to many other elicitin genes expressed by the genus *Phytophthora*, suggesting that it could silence many other elicitin genes and thereby provide resistance to many species of *Phytophthora*. The sequence selected was 282 nt long, therefore the sequence was repeated (=564 nt) in both the sense and antisense orientations to approximate the lengths of the sense and antisense portions of pVZA100 (SEQ ID 5), pVZA200 (SEQ ID 6) and pVZA400 (SEQ ID 8) that have been remarkably successful.

The success of this approach was demonstrated by the dramatic effect of pVZA300 in reducing the growth and causing malformation of hyphae of transformed *Phytophthora nicotianae* and *Phytophthora sojae* (FIG. 14 D, F) as compared to the effects of transformations with pCAMBIA1201, pVZA100, or pVZA200. The plasmids pVZA200 and pVZA300 are partially identical with both containing a cathepsin gene, but pVZA300 also contains the repeated elicitin gene. Therefore, the deleterious impact of pVZA300 on the fungi must be due to the elecitin gene. This has very positive implications for developing *Phytophthora* resistant plants and application of this approach to depathogenization of *Phytophthora* contaminated soils.

Transforming Methods

A wide variety of methods are available for introducing heterologous polynucleotides of the present invention into the target host under conditions that allow for stable maintenance and expression of the polynucleotide. The particular choice of a transformation technology will be determined by its efficiency to transform certain plant species as well as the experience and preference of the person practicing the invention with a particular methodology of choice. It will be apparent to the skilled person that the particular choice of a transformation system to introduce nucleic acid into plant cells is not essential to or a limitation of the invention, nor is the choice of technique for plant regeneration.

While various transformation methods are taught herein as separate methods, the skilled artisan will readily recognize that certain methods can be used in combination to enhance the efficiency of the transformation process. Non-limiting examples of such methods include bombardment with *Agrobacterium* coated microparticles (EP-A-486234) or microprojectile bombardment to induce wounding followed by cocultivation with *Agrobacterium* (EP-A-486233).

Direct delivery can be used to transform plant hosts according to the present invention. By way of non-limiting example, such direct delivery methods include polyethylene glycol treatment, electroporation, liposome mediated DNA uptake (e.g. Freeman et al. Plant Cell Physiol. 29: 1353 (1984)), or the vortexing method (e.g. Kindle, PNAS U.S.A. 87: 1228 (1990d). One form of direct DNA delivery is direct gene transfer into protoplasts from, for example, embryogenic cell suspension cultures (Lazzeri and Lorz (1988) Advances in Cell Culture, Vol. 6, Academic press, p. 291; OziasAkins and Lorz (1984) Trends in Biotechnology 2: 1 19).

Pollination Pathway

The skilled artisan is aware of certain challenges of genotype-dependant transformation arising from low regeneration potential of cereals. Accordingly, in one embodiment of the present invention, transformation is accomplished by a genotype-independent transformation approach based on the pollination pathway (Ohta Y., 1986). In maize, high efficiency genetic transformation can be achieved by a mixture of pollen and exogenous DNA (Luo Z. X. and Wu R., 1988, Proc. Natl. Acad. Sci. USA 83:715-719). Maize can be bred by both self-pollination and cross-pollination techniques. Maize has separate male and female flowers on the same plant, located on the tassel and the ear, respectively. Natural pollination occurs in maize when wind blows pollen from the tassels to the silks that protrude from the tops of the ears.

Transformation of rice according to the present invention can also be accomplished via the pollen-tube pathway (Plant Molecular Biology Reporter 6:165-174). The major potential advantages of the pollen-tube pathway approach include: (a) genotype independence; (b) lack of mosaicism; (c) no need for complicated cell and tissue culture techniques.

Transformation of tomato and melon with heterologous polynucleotides according to the present invention can be accomplished into intact plants via pollination pathway (Chesnokov, Yu. V., et al, 1992, USSR Patent No. 1708849;

Bulletin of the USSR Patents, No. 4; Chesnokov Yu. V. & Korol A. B. 1993; Genetika USSR, 29:1345-1355). The procedures of genetic transformation based on the pollination-fecundation pathway include: (i) employment of a mixture (paste) of the pollen and transforming DNA; (ii) delivery of the alien DNA into the pollen tube, after pollination; and (iii) microparticle bombardment of microspores or pollen grains.

*Agrobacterium* Technology

In one embodiment of the present invention, host plants are transformed using *Agrobacterium* technology. *Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation can efficiently be used with dicotyledonous host plants of the present invention including, by way of non-limiting example, *Arabidopsis*, corn, soybean, cotton, canola, tobacco, tomato, and potato.

*Agrobacterium*-mediated transformation is also applicable to nearly all monocotyledonous plants of the present invention. By non-limiting example, such monocotyledonous plant technologies are adaptable to rice (Hiei et al., 1997; Zhang et al., 1997; (Ishida et al., 1996); U.S. Pat. No. 5,591,616, specifically incorporated herein by reference in its entirety), wheat (McCormac et al., 1998), and barley (Tingay et al., 1997; McCormac et al., 1998).

*Agrobacterium*-mediated transformation, according to the present invention, can be accomplished with cultured isolated protoplasts and by transformation of intact cells or tissues.

*Agrobacterium*-mediated transformation in dicotyledons facilitates the delivery of larger pieces of heterologous nucleic acid as compared with other transformation methods such as particle bombardment, electroporation, polyethylene glycol-mediated transformation methods, and the like. In addition, *Agrobacterium*-mediated transformation appears to result in relatively few gene rearrangements and more typically results in the integration of low numbers of gene copies into the plant chromosome.

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

When *Agrobacterium* (e.g. *A. tumefaciens* and *A. rhizogenes*) is used to transform plant cells according to the present invention, the DNA to be inserted can be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation).

Binary vectors can replicate themselves both in *E. coli* and in Agrobacteria. Such vectors can comprise a selection marker gene and a linker or polylinker which are framed by the right and left T-DNA border regions. They can be transformed directly into Agrobacteria (Holsters et al. [1978] *Mol. Gen. Genet.* 163:181-187). The *Agrobacterium* used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted heterologous polynucleotides. No special demands are made of the plasmids in the case of injection and electroporation. It is possible to use ordinary plasmids, such as, for example, pUC derivatives.

Other transformation technology includes whiskers technology. See U.S. Pat. Nos. 5,302,523 and 5,464,765, both to Zeneca.

Microprojectile Bombardment

Optionally, host plant cells are transformed in accordance with the invention by microprojectile bombardment (U.S. Pat. Nos. 5,550,318; 5,538,880; 5,610,042; and 5,590,390; each of which is specifically incorporated herein by reference in its entirety). In this embodiment, particles are coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells are arranged on solid culture medium. The cells to be bombarded are positioned at an appropriate distance below the microprojectile stopping plate.

An illustrative embodiment of a transforming method for delivering subject vectors into plant cells is by acceleration is the Biolistics Particle Delivery System (BioRad, Hercules, Calif.), which is used to propel particles coated with DNA or cells through a screen, such as a stainless steel or Nytex screen, onto a filter surface covered with plant cells cultured in suspension. The screen disperses the particles so that they are not delivered to the recipient cells in large aggregates. While not bound by theory, it is believed that a screen intervening between the projectile apparatus and the cells to be bombarded reduces the size of projectiles aggregate and may contribute to a higher frequency of transformation by reducing the damage inflicted on the recipient cells by projectiles that are too large.

For the bombardment, cells in suspension are preferably concentrated on filters or solid culture medium. Alternatively, immature embryos or other target cells may be arranged on solid culture medium. The cells to be bombarded are positioned at an appropriate distance below the microprojectile stopping plate. If desired, one or more screens may be positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from 1 to 10 and average 1 to 3.

One skilled in the art can optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that the skilled artisan can adjust the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Results from such small scale optimization studies are disclosed herein and the execution of other routine adjustments will be known to those of skill in the art in light of the present disclosure.

Transformation by microprojectile bombardment is widely applicable, and can be used to transform virtually any plant species. Monocots are optionally transformed by bombardment according to the present invention, for example maize (U.S. Pat. No. 5,590,390), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991);

Dicots are optionally transformed by bombardment according to the present invention, for example, tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (Van Eck et al. 1995), and legumes in general (U.S. Pat. No. 5,563,055, specifically incorporated herein by reference in its entirety).

Electroporation

In one embodiment, plant cells are transformed using the method of electroporation, See, for example, WO 87/06614 to Boyce Thompson Institute; U.S. Pat. Nos. 5,472,869 and 5,384,253, both to Dekalb; and WO 92/09696 and WO 93/21335, both to Plant Genetic Systems.

The method of Krzyzek et al. (U.S. Pat. No. 5,384,253, incorporated herein by reference in its entirety), is well suited for the present invention. In this method, certain cell wall-degrading enzymes, such as pectin-degrading enzymes, are employed to render the target recipient cells more susceptible to transformation by electroporation than untreated cells. Alternatively, recipient cells are made more susceptible to transformation by mechanical wounding.

The method of Tada, Y., et al (Efficient gene introduction to rice by electroporation and analysis of transgenic plants: Use of electroporation buffer lacking chloride ions, Theor Appl Genet, Vol. 80: 475-480, 1990) is, for example, suitable for transforming rice.

In one embodiment, to effect transformation by electroporation, friable tissues, such as a suspension culture of cells or embryogenic callus are used.

Optionally, immature embryos or other organized tissue are transformed directly. In this technique, cell walls are partially degraded by exposing them to pectin-degrading enzymes (pectolyases) or mechanically wounding in a controlled manner.

Non-limiting examples plant cell hosts that can be transformed by electroporation of intact cells according to the present invention are wheat (according to, for example, Zhou et al., 1993), tomato (according to, for example Hou and Lin, 1996), soybean (according to, for example Christou et al., 1987) and tobacco (Lee et al., 1989). See also U.S. Pat. No. 5,384,253; Rhodes et al., 1995; and D'Halluin et al., 1992

In one embodiment, plants are transformed for electroporation of protoplasts (according to, for example, Bates, 1994; Lazzeri, 1995). Non-limiting examples of plant cell hosts that can be transformed by electroporation of protoplasts cells according to the present invention are soybean plants (according to, for example, Dhir and Widholm in PCT Publication No. WO 92/17598, specifically incorporated herein by reference), barley (e.g., Lazerri, 1995), sorghum (e.g., Battraw et al., 1991), (e.g., Bhattacharjee et al., 1997), wheat (e.g., He et al., 1994) and tomato (e.g. Tsukada, 1989).

Viral Vectors

Furthermore, viral vectors can also be used to transform plants according to the present invention. For example, monocotyledonous plants can be transformed with a viral vector using the methods described in U.S. Pat. No. 5,569,597 to Mycogen Plant Science and Ciba-Giegy, now Novartis.

U.S. Pat. No. 5,589,367 also describes plant transformation with a viral vector.

U.S. Pat. No. 5,316,931 describes plant transformation with a viral vector.

A large number of cloning vectors useful for higher plants (including monocots and dicots) according to the present invention comprise a replication system in *E. coli* and a marker that permits selection of the transformed cells. These vectors comprise, for example, pBR322, pUC series, M13 mp series, pACYC184, etc., and pCAMBIA 1201. Accordingly, the sequence comprising a heterologous polynucleotide of the present invention can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, are joined as the flanking region of the genes to be inserted (FIG. 1).

The use of T-DNA for the transformation of plant cells is described in EP 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1-46; An et al. (1985) *EMBO J.* 4:277-287; and many subsequent references widely known and available to those skilled in the art.

Marker Genes

In order to improve the ability to identify transformants, one may desire to employ one or more marker genes into a heterologous polynucleotide of the present invention.

Marker genes, according to the present invention, include those that encode a selectable marker and those that encode a screenable marker, depending on whether the marker confers a trait that one can "select" for by chemical means, i.e., through the use of a selective agent (e.g., a herbicide, antibiotic, or the like), or whether it is simply a "reporter" trait that one can identify through observation or testing, i.e., by "screening". Of course many examples of suitable marker genes or reporter genes are known to the art and can be employed in the practice of the invention.

Included within the terms selectable or screenable marker genes are also genes that encode a "secretable marker" whose secretion can be detected as a means of identifying or selecting for transformed cells. Examples include markers that encode a secretable antigen that can be identified by antibody interaction, or even secretable enzymes that can be detected by their catalytic activity. Secretable proteins fall into a number of classes, including small, diffusible proteins detectable, e.g., by ELISA, and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

One example of a protein suitable for modification in this manner is extensin, or hydroxyproline rich glycoprotein (HPRG). The use of the HPRG (Stiefel et al., 1990) is well characterized in terms of molecular biology, expression, and protein structure. However, any one of a variety of extensins and/or glycine-rich wall proteins (Keller et al., 1989) could be modified by the addition of an antigenic site to create a screenable marker.

Elements of the present disclosure are exemplified in detail through the use of particular marker genes. However in light of this disclosure, numerous other possible selectable and/or screenable marker genes will be apparent to those of skill in the art in addition to the one set forth herein below. Therefore, it will be understood that the following discussion is exemplary rather than exhaustive.

Selectable Markers

Selectable markers for use in connection with the present invention include, but are not limited to, a neo gene (Potrykus et al., 1985) that codes for kanamycin resistance and can be selected for using kanamycin, G418, and the like; a bar gene that codes for bialaphos resistance; a gene that encodes an altered EPSP synthase protein (Hinchee et al., 1988) thus conferring glyphosate resistance; a nitrilase gene such as bxn from *Klebsiella ozaenae* that confers resistance to bromoxynil (Stalker et al., 1988); a mutant acetolactate synthase gene (ALS) or acetohydroxyacid synthase gene (AHAS) that confers resistance to imidazolinone, sulfonylurea, or other ALS-inhibiting chemicals (European Patent Application 154,204); a methotrexate-resistant DHFR gene (Thillet et al., 1988); a dalapon dehalogenase gene that confers resistance to the herbicide dalapon (U.S. Pat. No. 5,780,708); or a mutated anthranilate synthase gene that confers resistance to 5-methyl tryptophan (PCT Publication No. WO 97/26366). Where a mutant EPSP synthase gene is employed, additional benefit may be realized through the incorporation of a suitable chloroplast transit peptide, CTP (U.S. Pat. No. 4,940,835). See also, Lundquist et al., U.S. Pat. No. 5,508,468.

An illustrative embodiment of a selectable marker gene capable of being used in embodiments of the present invention to select transformants are those that encode the enzyme phosphinothricin acetyltransferase, such as the bar gene from *Streptomyces hygroscopicus* or the pat gene from *Streptomyces viridochromogenes* (U.S. Pat. No. 5,550,318, which is incorporated by reference herein). The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

Suitable selectable marker genes contemplated herein include an aminoglycoside phosphotransferase gene, neomycin phosphotransferase gene, G418 resistance gene, glyphosate resistance gene, hygromycin resistance gene, methotrexate resistance gene, imidazolinones resistance gene, sulfonylureas resistance gene, triazolopyrimidine herbicide resistance gene, ampicillin resistance gene, tetracycline resistance gene, bacterial kanamycin resistance gene, phosphinothricin resistance gene, chloramphenicol acetyltransferase (CAT) gene and luciferase gene, amongst others.

Screenable Markers

Screenable markers that may be employed include, but are not limited to, a beta-glucuronidase or uidA gene (GUS) that encodes an enzyme for which various chromogenic substrates are known; an R-locus gene, which encodes a product that regulates the production of anthocyanin pigments (red color) in plant tissues (Dellaporta et al., 1988); a beta-lactamase gene (Sutcliffe, 1978), which encodes an enzyme for which various chromogenic substrates are known (e.g., PADAC, a chromogenic cephalosporin); a xyle gene (Zukowsky et al., 1983), which encodes a catechol dioxygenase that can convert chromogenic catechols; an alpha-amylase gene (Ikuta et al., 1990); a tyrosinase gene (Katz et al., 1983), which encodes an enzyme capable of oxidizing tyrosine to DOPA and dopaquinone which in turn condenses to form the easily detectable compound melanin; a beta-galactosidase gene, which encodes an enzyme for which there are chromogenic substrates; a luciferase (lux) gene (Ow et al., 1986), which allows for bioluminescence detection; or even an aequorin gene (Prasher et al., 1985), which may be employed in calcium-sensitive bioluminescence detection, or a green fluorescent protein gene (Niedz et al., 1995).

Genes from the R gene complex are contemplated as useful screenable markers. The R gene complex encodes a protein that acts to regulate the production of anthocyanin pigments in most seed and plant tissue. Maize lines can have one, or as many as four, R alleles that combine to regulate pigmentation in a developmental and tissue specific manner. Thus, an R gene introduced into such cells will cause the expression of a red pigment and, if stably incorporated, can be visually scored as a red sector. If a line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 that contains the rg-Stadler allele and TR112, a K55 derivative that is r-g, b, P1. Alternatively any genotype of maize can be utilized if the C1 and R alleles are introduced together.

It is further contemplated that R gene regulatory regions may be employed in heterologous polynucleotides of the present invention in order to provide mechanisms for controlling the expression of such heterologous polynucleotides. More diversity of phenotypic expression is known at the R locus than at any other locus (Coe et al., 1988). It is contemplated that regulatory regions obtained from regions 5' to the structural R gene would be valuable in directing the expression of genes, e.g., insect resistance, drought resistance, herbicide tolerance or other protein coding regions. For the purposes of the present invention, it is believed that any of the various R gene family members may be successfully employed (e.g., P, S, Lc, etc.). However, the most preferred will generally be Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for populational screening for bioluminescence, such as on tissue culture plates, or even for whole plant screening.

Marker Gene Strandedness

According to the present invention, marker genes can be designed by selection of sequence and position within the heteropolynucleotide to result in a positive or negative marker. When a heteropolynucleotide contains sequences of a marker gene but does not contain sufficient complementary sequences to the marker gene, a transcript of the heteropolynucleotide will contain the marker gene in a single stranded region and it can be expressed. Thus expression is correlated with integration of the heteropolynucleotide into the host plant. When a heteropolynucleotide contains sequences of a marker gene and sufficient complementary sequences to the marker gene, a transcript of the heteropolynucleotide will contain the marker gene in a double stranded region and it will be silenced. Thus, expression of such a marker gene will indicate that the heteropolynucleotide is not being silenced in the host plant (i.e. "negative marker"). When a plant cell is transformed with a heteropolynucleotide comprising both a positive marker and a negative marker gene expresses the positive marker gene but does not express the negative marker gene, this indicates that the plant is transcribing and silencing at least part of the heteropolynucleotide. Thus expression is correlated with integration of the heteropolynucleotide into the host plant (i.e. positive sequences can be selected).

Choice of Marker Gene Sequence

A skilled artisan will now readily recognize how combinations of markers at different positions within a heterologous polynucleotide of the present invention can be effected. Such differences in position effect whether the marker is silenced or not (e.g. a gene within the region that forms a double stranded structure by way of hydrogen bonding is recognized as foreign by the plant's internal defense mechanisms and hydrolyzed into siRNA [i.e. "silenced"]).

For example, in one embodiment, a heterologous polynucleotide of the present invention contains the hypothetical A gene (that is, any marker gene of the present invention) upstream of the double stranded region and a hypothetical B gene within the double stranded region. A non-transformed cell is deficient in A expression ("A−). It is also B− and C−. A transformed cell that functionally inactivates B region (e.g. by gene silencing of the region wherein the B gene lies) is A+ and B−. A transformed cell that fails to inactivate the B region is A+ and B+.

A skilled artisan will now recognize that the presence of antisense sequences of a marker gene, appropriately placed downstream of the sense sequences of the marker gene, will further facilitate gene silencing (e.g. double strand formation) of such marker gene.

It should also now be readily recognized that a marker localized downstream of a double stranded region will also be silenced if no promoter lies between such double stranded region and such marker.

In one embodiment, heterologous polynucleotides of the present invention include those with the structures shown in FIGS. 15-19.

Promoter and Regulatory Elements

According to the present invention, a heterologous polynucleotide, or a portion thereof, is capable of being transcribed in a plant. In plants, such transcription requires a promoter that is operably linked to the heterologous polynucleotide. Such a promoter can be endogenous to the plant. By way of example, a heterologous polynucleotide can be inserted adjacent to a constitutive or inducible plant promoter.

The heterologous polypeptide of the present invention can optionally contain a promoter. Such a promoter can be a plant promoter or a non-plant promoter that functions in a plant.

Plant promoters include but are not limited to ribulose-1,6-bisphosphate (RUBP) carboxylase small subunit (ssu), beta-conglycinin promoter, beta-phaseolin promoter, ADH promoter, heat-shock promoters, and tissue specific promoters such as a constitutive promoterwhere it is desirable to directing continuous gene expression in all cell types and at all times (e.g., actin, ubiquitin, CaMV 35S, and the like).

Promoters from a variety of sources can be used efficiently in plant cells to express foreign genes. For example, promoter regulatory elements of bacterial origin, such as the octopine synthase promoter, the nopaline synthase promoter, the mannopine synthase promoter; promoters of viral origin, such as the cauliflower mosaic virus (35S and 19S), 35T (which is a re-engineered 35S promoter, see U.S. Pat. No. 6,166,302, especially Example 7E) and the like may be used.

It may be desirable to use an inducible promoter, which is responsible for expression of genes in response to a specific signal, such as: physical stimulus (heat shock genes), light (RUBP carboxylase), hormone (Em), metabolites, chemical, and stress. Other desirable transcription and translation elements that function in plants may be used. Numerous plant-specific gene transfer vectors are known in the art.

It may be desirable to use a promoter that is active during a certain stage of the plant's development as well as active in plant tissues and organs. Examples of such include but are not limited to pollen-specific, embryo-specific, corn-silk-specific, cotton-fiber-specific, root-specific, seed-endosperm-specific promoters and the like. Tissue specific promoter regulatory elements can be used where it is desirable to promte transcription in tissues such as leaves or seeds (e.g., zein, oleosin, napin, ACP, globulin and the like).

While any promoter that functions in a plant cell (i.e. supports transcription of a heterologous polynucleotide) is useful in the present invention, it can be desirable to select a relatively stronger or weaker promoter. One embodiment of the present invention uses a strong promoter to drive the sense sequence of a pest pathogenicity gene and a weaker promoter to drive the antisense sequence of the pest pathogenicity gene. One skilled in the art can readily determine promoter strength empirically within the embodiments of the present invention. When an embodiment contains two promoters (driving two different transcripts), the relative transcription rate can be determined by quantifying the transcripts (e.g. quantitative PCR).

Examples of promoters that are relatively strong are the figwort mosaic virus promoter and the enhanced CaMV 35S promoter. An example of a promoter that is relatively weaker is the CaMV 35S promoter. One skilled in the art will readily appreciate that "weaker" and "stronger" promoters is a relative term, and they can be empirically identified by, for example, quantitative PCR with the appropriate primers against the transcript that is driven by the promoters.

Other elements such as matrix attachment regions, scaffold attachment regions, introns, enhancers, polyadenylation sequences and the like may be present and thus may improve the transcription efficiency or DNA integration. Such elements may or may not be necessary for DNA function, although they can provide better expression or functioning of the DNA. Such elements may be included in the DNA as desired to obtain optimal performance of the transformed DNA in the plant. Typical elements include but are not limited to Adh-intron 1, Adh-intron 6, the alfalfa mosaic virus coat protein leader sequence, the maize streak virus coat protein leader sequence, as well as others available to a skilled artisan.

Terminator

Heterologous polynucleotides of the present invention can optionally contain a terminator. The term "terminator" refers to a DNA sequence at the end of a transcriptional unit which signals termination of transcription. Eukaryotic terminators are 3'-non-translated DNA sequences containing a polyadenylation signal, which facilitates the addition of poly (A) sequences to the 3'-end of a primary transcript.

Terminators active in cells derived from viruses, yeast, molds, bacteria, insects, birds, mammals and plants are known and described in the literature and useful in the present invention. They may be isolated from bacteria, fungi, viruses, animals and/or plants.

Examples of terminators suitable for use in the present invention include the nopaline synthase (NOS) gene terminator of *Agrobacterium tumefaciens*, the terminator of the Cauliflower mosaic virus (CaMV) 35S gene, the zein gene terminator from *Zea mays*, the Rubisco small subunit (SSU) gene terminator sequences, Subclover stunt virus (SCSV) gene sequence terminators (International Patent Application No. PCT/AU95/00552), and the terminator of the *Flaveria bidents* malic enzyme gene NSEA3 (PCT/AU95/00552).

Those skilled in the art will be aware of additional promoter sequences and terminator sequences suitable for use in performing the invention. Such sequences may readily be used without any undue experimentation.

Embodiments of the present invention are taught herein where it is desirable to have more than one terminator. Examples of such are embodiments are where the sense and antisense sequences are to be contained on separate transcripts (i.e. each having its own 3' and 5' end).

Plant Regeneration and Propagation

Following transformation, a plant may be regenerated, e.g., from single cells, callus tissue, or leaf discs, as is standard in the art. Almost any plant can be entirely regenerated from cells, tissues, and organs of the plant. Available techniques are reviewed in Vasil et al. (1984) in Cell Culture and Somatic Cell Genetics of Plants, Vols. I, II, and III, Laboratory Procedures and Their Applications (Academic press); and Weissbach et al. (1989) Methods for Plant Molecular Biology, Academic Press, 1989.

During suspension culture development, small cell aggregates (10-100 cells) are formed, apparently from larger cell clusters, giving the culture a dispersed appearance. Upon plating these cells to solid media, somatic embryo development can be induced, and these embryos can be matured, germinated and grown into fertile seed-bearing plants. Alternatively, callus cells growing on solid culture medium can be induced to form somatic embryos from which fertile seed bearing plants may develop. The characteristics of embryogenicity, regenerability, and plant fertility are gradually lost as a function of time in suspension culture. Cryopreservation of suspension cells arrests development of the culture and prevents loss of these characteristics during the cryopreservation period.

The transformed plants may then be grown, and either pollinated with the same transformed strain or different strains, and the resulting line having expression of the desired phenotypic characteristic identified. Two or more generations may be grown to ensure that expression of the desired phenotypic characteristic is stably maintained and inherited, and then seeds harvested to ensure expression of the desired phenotypic characteristic has been achieved.

In addition to a plant, the present invention provides any clone of such a plant, seed, selfed or hybrid descendants, and any part of any of these, such as cuttings, pollen, or seed. The invention provides any plant propagule, that is any part which may be used in reproduction or propagation, sexual or asexual, including cuttings, seed, and so on. Also encompassed by the invention is a plant which is a sexually or asexually propagated off-spring, clone, or descendant of such a plant; or any part or propagule of said plant, off-spring, clone, or descendant. Plant extracts and derivatives are also provided.

Gene Stacking

A heterologous polynucleotide according to the present invention can comprise a plurality of sense sequences and a plurality of antisense sequences (i.e. a "polycistronic heterologous polynucleotide"). Thus, a heterologous polynucleotide can protect a plant against multiple pests.

One skilled in the art will now recognize that, by using gene stacking, a plant can be made resistant to a plurality of pests. The plurality of pests can be from the same phylum or from different phyla. For example, a plant can be made resistant to a plurality of fungal pests. As one non-limiting example of gene stacking according to the present invention, soybeans can be made resistant to brown stem rot (*Phialophora gregata*), stem and root rot (*Phytophthora sojae*), white mold disease (*Sclerotinia sclerotiorum*), sudden death syndrome (*Fusarium solani pisi*), and Asian rust (*Phakopsora pachyrhizi*).

Optionally, a plant can be made resistant to a plurality of insect pests. As one non-limiting example of gene stacking according to the present invention, potatoes can be made resistant to potato leafhopper (Empoasca filament), Colorado potato beetle (*Leptinotarsa decemlineata*), and green peach aphid (*Myzus persicae*).

Optionally, a plant can be made resistant to a plurality of fungal and non-fungal pests. As one non-limiting example of gene stacking according to the present invention, potatoes can be made resistant to potato golden nematode (*Globodera rostochiensis*), Colorado potato beetle (*Leptinotarsa decemlineata*), and potato late blight (*Phytophthora infestans*).

In one embodiment of the present invention, the heterologous polynucleotide comprises two different sense and two different antisense sequences.

In one embodiment of the present invention, the heterologous polynucleotide comprises at least three different sense and at least three different antisense sequences.

Plant pests often cause the infected plants to become yellow or brown, to be reduced in size, to produce less root exudates and to mature more rapidly. Therefore, controlling a single major pest of a plant may in turn make that plant more susceptible to other pests. If a fungal disease of a plant is controlled, then the healthy plant will remain large and green for a longer period, and therefore be attractive to and susceptible to insects and airborne fungal diseases. The green plant also may produce more root exudates which will attract more nematodes and root infecting fungi. It has been discovered herein that it can be surprisingly advantageous to transform a plant with a heterologous polynucleotide containing sequences homologous to a plurality of pests genes, wherein such genes are from pests of different taxons (e.g. subspecies, species, genera, families, orders, class).

Depathogenesis

It has been discovered that when a pest infects a host plant cell transformed according to the present invention, the pest becomes less pathogenic to the transformed host plant cell and non-transformed host plant cells. Moreover, in one embodiment, a pest infects a host plant cell transformed according to the present invention and then the gene silencing molecules derived from the plant by feeding are subsequently transmitted through mating (e.g. by cytoplasmic transmission, conjugation, hyphal anastomosis, etc.) to populations of the pest and produce a less pathogenic pest. In this way, populations of pests can be made non-pathogenic (i.e. less pathogenic) by, for example, a pest that is unable to multiply, and the macroenvironment (e.g. soil, plant foliage, plant debris, buildings) contaminated with a pest can be protected or decontaminated therefrom.

Optionally, progeny of the pest are less pathogenic to the transformed host plant cell and non-transformed host plant cells.

Accordingly, one embodiment of this invention is a mechanism for biological control, and it has great economic value in that it can be used to deplete important fields of pathogenic pest isolates of fungi and reduce the application of pesticides. In this embodiment the transgenic plant transmits the siRNAs to the pest by way of pest feeding behavior, and the pest loses its pathogenicity due to the subsequent silencing of its own pathogenic gene. Moreover, the pest progeny will in turn be nonpathogenic (e.g. by cytoplasmic transmission, mating, conjugation, hyphal anastomosis), thereby effectively cleaning up the local environment of that pest and preventing or significantly reducing its plant destroying behavior.

Depathogenesis, in one embodiment, is accomplished by co-cultivating nonpathogenic (either transformed directly or having obtained siRNAs), pests with pathogenic pests. Such co-cultivation is accomplished, by way of nonlimiting example, by broadcast of the transgenic pest to grow and infest the soil wherein the nonpathogenic pests then mate with like species. Such broadcast can be accomplished for fungi, by way of nonlimiting example, by cultivating transformed fungi on barley or wheat seeds and then distributing such seeds to soil that is in need of being depathogenized or protection from pathogenic pests.

This embodiment is suitable for protecting established valuable plants such as trees (e.g. redwoods, oaks, palms, maples, etc.).

Although the foregoing discussion uses fungal plant pathogens as an example, the strategy for depathogenesis can be adapted to any other plant pests that would transmit the "silenced" trait to their progeny, as will be readily apparent to the skilled artisan.

First, it is possible to "depathogenize" a pest by silencing a pest pathogenicity gene. The pest then could survive in the environment (e.g. soil) and spread the siRNAs throughout the population and no longer attack plants. Second, by silencing major structural genes or essential nutrition genes such as ribosomal RNA or elicitin genes, respectively, it is possible to debilitate or kill a pest thereby eliminating it from crop fields or lowering its presence below economic thresholds.

EXAMPLES

Example 1

Cloning Strategy

The plasmids pVZA100, pVZA200, pVZA300, and pVZA400 are embodiments that were designed for transformation of various plant species, including, but not limited to, tobacco (*Nicotiana tobacum*, cv. Xanthi), soybean (*Glycine max* cv. Williams 82), potato (*Solanum tuberosm* cv. Alpha) and corn (*Zea mays* cv. Hi II×B73). pVZA100 contains the full-length cutinase gene from *Phytophthora nicotianae* in both the sense (S) and antisense (AS) orientations, separated by a spacer region containing a portion (817 bp) of the *E. coli* β-glucuronidase gene (GUS) referred to as dGUS. pVZA100 expression in plants is under the control of the cauliflower mosaic virus (CaMV) 35S promoter and the cucumber mosaic virus (CMV) capsid protein gene 5' untranslated region (5' UTR). The termination signal also is from the CaMV 35S gene. The backbone of the pVZA100 plasmid is the plasmid pCAMBIA1201 (FIG. 1) (Roberts et al., 2000). Its plant selectable marker is the antibiotic hygromycin. The expression of hygromycin phosphotransferase in pCAMBIA 1201 also is controlled by the CaMV 35S promoter and terminator. The reporter gene in pCAMBIA 1201 is GUS with a catalase intron, also with the CaMV 35S promoter, but with the nopaline synthase (NOS) terminator.

Example 2

Construction of the Intermediary Plasmid pVZA1

Figure 2:
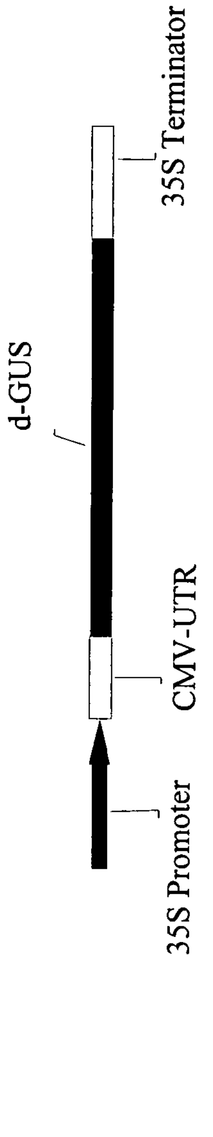
FIG. 2 is a drawing of the insert in the intermediary plasmid pVZA1.

Because of its versatility, the gene expression plasmid pUC18 cpexp (Slightom, 1991) was selected to contain the gene silencing cassette. This plasmid is pUC18, containing the CaMV 35S promoter, followed by the CMV capsid protein gene 5' UTR and the CaMV 35S gene termination signal. A Bgl II site was engineered into the polylinker between the CMV 5' UTR and the CaMV 35S terminator. To obtain dGUS, the plasmid pCAMBIA1201 (FIG. 1) was double digested with Nco I and Hinc II. The GUS fragment 821 bp in length, corresponding to nucleotides 9540 to 10361 of pCAMBIA1201, was isolated and purified by agarose gel electrophoresis. That fragment was then digested (blunted) at the 3' Nco I site using mung bean nuclease to reduce it to 817 bp. This blunt-ended dGUS was then re-purified by agarose gel electrophoresis and ligated into the Bgl II site of pUC18 cpexp to yield the intermediary plasmid pVZA1 (FIG. 2).

Example 3

Figure 3:
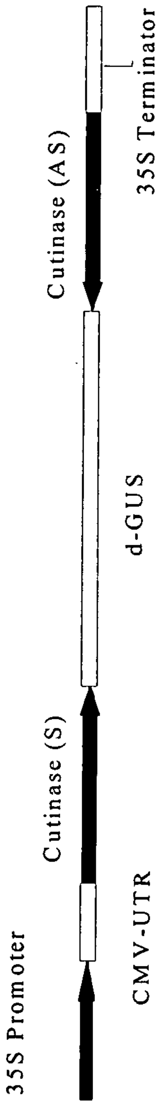
FIG. 3 is the pVZA100 silencing cassette cloned in plasmid pVZA3 and ready for transfer to pCAMBIA1201.

Construction of the pVZA2, pVZA3, pVZA100, pVZA200, pVZA300 and pVZA400 Plasmids The full length cutinase gene from *P. nicotianae* was amplified in the antisense orientation by PCR from a cutinase clone in the plasmid pZErO-2.1 (Munoz and Bailey, 1998) using primers VZA 1F (SEQ ID NO: 1) and VZA 2R (SEQ ID NO: 2) containing the Not I and Nco I restriction sites, respectively. It was then purified by agarose gel electrophoresis, and ligated into the Not I and Nco I sites of the plasmid pVZA1. The resulting plasmid, pVZA2, was cloned in *E. coli* and purified. A copy of the cutinase gene in the sense orientation was amplified by PCR from the same cutinase clone in the plasmid pZErO-2.1 using primers VZA 3F and VZA 4R (SEQ ID NO: 3 and SEQ ID NO: 4, respectively) containing the Apa I and Xho I restriction sites, respectively. It was purified by agarose gel electrophoresis, and ligated into the Apa I and Xho I restriction sites in the plasmid pVZA2 to produce the final intermediary plasmid pVZA3 (FIG. 3). The portion containing dGUS and separating the cutinase gene in sense and antisense orientation is referred to as the silencing construct. The portion containing the silencing construct plus the regulatory elements for the construct (35S promoter, the 5' UTR and the 35S terminator) is referred to as the silencing cassette (FIG. 3).

The silencing cassette was excised from plasmid pVZA3 by double restriction digestion with EcoR I and Hind III and purified by agarose gel electrophoresis. The plasmid pCAMBIA1201 was double digested with EcoR I and Hind III, and the silencing cassette was ligated into those sites to produce the final plant transformation plasmid pVZA100. The presence of the entire silencing cassette was confirmed by restriction digestion of pVZA100 with PstI (which releases the whole insert) and by digestions with the various restriction enzymes used in its assembly. The digestion products were separated by agarose gel electrophoresis and compared with known molecular standards. The sequence, 2201 nt, of the silencing construct was confirmed by sequencing of the DNA, and it is SEQ ID NO: 5. The following oligonucleotide pairs were used as PCR primers to detect the presence of the respective genes in pVZA100 and in transgenic plants: cutinase (SEQ ID NOs: 1 and 2, or SEQ ID NOs: 3 and 4); GUS (SEQ ID NOs: 9 and 10) and hygromycin phosphotrasferase (SEQ ID NOs: 11 and 12).

Plant transformation plasmids pVZA200, pVZA300 and pVZA400 were based on the same principle as pVZA100. The silencing construct was an inverted repeat of the selected pest pathogenicity gene in both the sense and antisense orientations, separated by the dGUS fragment. However, the silencing constructs for pVZA200, pVZA300, and pVZA400 were synthesized commercially by GenScript Corporation (Piscataway, N.J.) with ApaI and Not I restriction sites at the 5' and 3' ends respectively, and cloned in the pUC57 vector.

The silencing construct of pVZA200 contained nucleotides 221 to 820 of the cathepsin B gene (GenBank locus AY702822) of the aphid *Myzus persicae*. This aphid is a major pest and the most efficient vector of many plant viruses. Cathepsin B is a cysteine protease, a digestive enzyme required for the survival and development of *Myzus persicae*. The 2031 nt sequence of the silencing construct for pVZA200 is shown as SEQ ID NO: 6.

The regulatory elements were then added to the pVZA200 silencing construct to yield the pVZA200 silencing cassette. For this, the entire pVZA100 silencing cassette was excised from pVZA100 by digestion with EcoR I and Hind III and purified by agarose gel electrophoresis. It was cloned into a similarly digested pUC19. This plasmid was then digested with ApaI and Not I. The pUC19 portion containing the regulatory elements from pVZA100 was purified and ligated to the pVZA200 silencing construct released from pUC57 by digestion with ApaI and Not I. The pVZA200 silencing cassette, now flanked by the regulatory elements from pVZA100, was increased in pUC19. The entire pVZA200 silencing cassette was excised from pUC19 by digestion with EcoR I and Hind III and then ligated into the EcoR I and Hind III sites of pCAMBIA1201 to complete the pVZA200 plant transformation plasmid. As with pVZA100, the presence of the entire silencing cassette was confirmed by restriction digestion of pVZA200 with PstI and by digestions with the various restriction enzymes used in its assembly. The digestion products were separated by agarose gel electrophoresis and compared with known molecular standards.

The following oligonucleotide pairs were used as PCR primers to detect the presence of the respective genes in pVZA200 and in transgenic plants: cathepsin (SEQ ID NOs: 38 and 39); GUS (SEQ ID NOs: 9 and 10) and hygromycin phosphotrasferase (SEQ ID NOs: 11 and 12).

The plant transformation plasmids pVZA300 and pVZA400 were planned similarly and synthesized. The silencing construct of pVZA300 was a double gene construct, containing gene sequences from two different plant pests. It was designed to contain the same cathepsin B gene inverted repeat around the dGUS fragment as the silencing construct of pVZA200. But in addition, at each end it contained the partial coding sequence for the elicitin INF1 of *Phytophthora infestans* (GenBank locus AY766228). This elicitin gene is required by *Phytophthora infestans* for pathogenicity and as a sterol receptor because *Phytophthora* spp. do not synthesize the sterols essential for their growth and development. The elicitin sequence was 282 nt long. Therefore, to obtain a sequence approaching 600 nt, the sequence was repeated to obtain 564 nt.

An ApaI restriction site was included at the 5' end of the elicitin sense sequence, and a NotI restriction site was included at the 3' end of the elicitin antisense sequence. The elicitin sense sequence was added to the 5' end of the pVZA200 sequence, and the elicitin antisense sequence was added to the 5' end of the pVZA200 sequence to complete the silencing construct of pVZA300. It is 3159 nt long and composed of the elicitin gene and cathepsin gene both in the sense orientation, followed by dGUS, followed by the cathepsin gene and elicitin gene, respectively, both in the antisense orientation.

The sequence of the silencing construct for pVZA300 is shown as SEQ ID NO: 7. This sequence was synthesized by GenScript Corporation and cloned in the pUC57 vector. The regulatory elements were then added as described for pVZA200 to complete the silencing cassette for pVZA300, and it was cloned into the EcoR I and Hind III sites of pCAMBIA1201. As previously, the presence of the entire silencing cassette was confirmed by restriction digestion of pVZA300 with PstI and by digestions with the various restriction enzymes used in its assembly. The digestion products were separated by agarose gel electrophoresis and compared with known molecular standards. The following oligonucleotide pairs were used as PCR primers to detect the presence of the respective genes in pVZA300 and in transgenic plants: elicitin and cathepsin overlap (SEQ ID NOs: 40 and 39) cathepsin (SEQ ID NOs: 38 and 39); GUS (SEQ ID NOs: 9 and 10) and hygromycin phosphotrasferase (SEQ ID NOs: 11 and 12).

The silencing construct of the plant transformation plasmid pVZA400 contained nt 1-600 of the ribosomal RNA genes (rDNA) of *Phytophthora infestans* (GenBank locus AJ854293) in the sense and antisense orientations, respectively, separated by dGUS. An ApaI and NotI restriction site were included on the 5' and 3' ends, respectively. The sequence of the silencing construct (2031 nt) for pVZA400 is shown as SEQ ID NO: 8. It was synthesized by GenScript Corporation and cloned in the pUC57 vector. The regulatory elements were then added as described for pVZA200 to complete the silencing cassette for pVZA400, and it was cloned into the EcoR I and Hind III sites of pCAMBIA1201. As previously, the presence of the entire silencing cassette was confirmed by restriction digestion of pVZA400 with PstI and by digestions with the various restriction enzymes used in its assembly. The digestion products were separated by agarose gel electrophoresis and compared with known molecular standards.

The following oligonucleotide pairs were used as PCR primers to detect the presence of the respective genes in pVZA400 and in transgenic plants: ribosomal DNA (SEQ ID NOs: 41 and 42); GUS (SEQ ID NOs: 9 and 10) and hygromycin phosphotrasferase (SEQ ID NOs: 11 and 12).

Example 4

Transformation Methods

Plant cells (including tobacco, soybean, potato and corn) were transformed with transformation plasmids pCAMBIA1201, pVZA100, pVZA200, pVZA300, and pVZA400 using biolistics or with pVZA100 using strain PGV 2260 of *Agrobacterium tumefaciens*. Fungal cultures were transformed only by biolistics with transformation plasmids pCAMBIA1201, pVZA100, pVZA200, pVZA300, and pVZA400.

Preparation of tungsten or gold microprojectiles for bombardment with the helium-driven biolistic device was according to the protocol of Shark et al. 1991. The microprojectiles were coated with either pCAMBIA1201, pVZA100, pVZA200, pVZA300, pVZA400, or with no DNA. For plant tissue and fungal culture transformation, the Dupont PDS-1000 apparatus was used under vacuum (23 mm Hg) and at 1200 PSI with tissues at 8 and 12 cm from the stopping plate. For seedling and plantlet transformation, a hand held homemade particle gun was used at 200 PSI, and held as close as possible to the developing meristem.

The transformations with *Agrobacterium tumefaciens* were performed essentially as described by Rogers et al. (1987). Although biolistics and *Agrobacterium tumefaciens* transformation are used to exemplify this portion of the subject invention, any method of introducing heterologous DNA into target cells for purposes of transformation that is known in the art could be used, as would readily be appreciated by the ordinarily skilled artisan, and as would be optimized depending on the target species.

Example 5

Tobacco Transformation with pVZA100 and Regeneration

Organogenic callus cultures of *Nicotiana tabacum* cv Xanthi were maintained in shake cultures in the laboratory and transferred monthly to fresh MS medium (Murashige and Skoog, 1962). Calli were removed from flasks aseptically, filtered free of liquid and spread on sterile filter paper in a sterile plastic Petri dish. They were bombarded with pVZA100 according to the methods described above, and the filter paper was transferred to phytohormone-free MS medium overnight. The following day the filter paper was transferred to MS medium containing 1 mg/l 6-benzyladenine, 0.1 mg/l napthaline acetic acid, 1 mg/l thiamine-HCl, 100 mg/l inositol, 30 g/l sucrose, 6 g/l phytagar and 30 ug/ml hygromycin for selection of the transgenic cells. For regeneration, the expanding calli were transferred to fresh MS medium every 2 weeks. Emerging shoots were then transferred to MS medium without phytohormones to form roots. Rooted plantlets were transferred to soil or tested directly for resistance to *P. nicotianae*. Plants were grown to maturity in soil and seed collected for subsequent analysis.

Example 6

Fungal Transformation and Selection Protocols

Five mm mycelial discs of *Phytophthora nicotianae, P. sojae* and *P. infestans* were bombarded according to the methods and with the constructs described in Examples 3 and 5. Bombarded cultures were placed on plates of V-8 agar and incubated at 27C overnight. The following day they were transferred to V-8 agar plates containing 400 ug/ml hygromycin and incubated at 27° C. for 3-4 days. Discs (5 mm) were cut from the new growth and transferred to Petri dishes containing 15 ml of V-8 broth and incubated at 27° C. for 2 days. The mycelial mats were washed with sterile water, pressed dry and incubated for 2 days with 10 ml of soil extract to induce sporangia formation. To induce zoospore release, the mats were placed in sterile demineralized water and chilled at 4° C. for 30-60 min. Zoospores were collected by centrifugation for 5 min. at 5,000 g and 4° C. For selection, the zoospore concentration was adjusted to approximately 1,000/ml and plated on V-8 agar containing 400 ug/ml hygromycin and X-gluc (Jefferson et al., 1986) and incubated for several days at 27° C.

Those isolates stably transformed with the GUS gene in pCAMBIA1201 appeared on the X-gluc agar as small blue colonies originating from single zoospores. They were transferred to individual plates of V-8 agar containing 400 ug/ml hygromycin, and the cultures consistently stained blue, positive for GUS, after many transfers. Those isolates transformed with the pVZA100, pVZA200, pVZA300, and pVZA400 silencing plasmids also initially appeared as small blue colonies originating from single zoospores. They were transferred to plates of V-8 agar containing 400 ug/ml hygromycin and X-gluc. After 2-3 transfers on this medium, those colonies which survived became white, indicating that the GUS gene had been silenced. All cultures were maintained at 27° C. and transferred monthly to fresh medium.

Example 7

Transformation of Corn, Soybeans and Potato

Corn was transformed by bombarding Type II callus from Hi II germplasm with gold particles coated with two plasmids, pVZA100 and pBAR184 (Frame et al., 2000). The pBAR184 was included so that the co-transformants could be selected and regenerated on media containing the herbicide bialaphos rather than hygromycin. Calli were grown and selected on $N^6$-based media containing 2 mg/l each of 2,4-dichlorophenoxyacetic acid and bialaphos. For regeneration and rooting, embryos were transferred to MS media containing 2 mg/l of bialaphos, and no phytohormones. Rooted plantlets were assayed by PCR.

Soybean was transformed both by *Agrobacterium tumefaciens* and biolistics. Mature embryos were excised aseptically from hydrated seeds of Williams soybean. The embryos were then soaked for 15 min. in a few milliters of a culture of *Agrobacterium tumefaciens* that had been grown on a shaker overnight at 28C and contained either pCAMBIA1201 or pVZA100. The treated embryos were placed on MS medium containing 15 mg/L of hygromycin and phytohormones (BAP and NAA) and then on MS medium free of phytohormones for rooting. Embryo-like structures formed and germinated, and leaves were produced (FIG. 6), but no plants were regenerated and rooted, despite testing of many media. Biolistic transformation of soybean was performed using the hand held homemade particle gun. Seedlings 8-10 days old and 6-10 cm tall were bombarded with gold particles coated with either pCAMBIA1201, pVZA100, pVZA200, pVZA300 or pVZA400 or with no DNA. The plants were grown in the greenhouse and assayed by PCR. Mature seed was collected and tested for resistance to *P. sojae*.

Potato was transformed both by *Agrobacterium tumefaciens* and biolistics. Russett Burbank and Alpha potatoes were transformed by *Agrobacterium tumefaciens*. Tubers were surface disinfested, and the potato "eyes" were excised and plated on solid MS medium without phytohormones. The eyes germinated, and plantlets were produced by cutting a node section containing one leaf and placing the stem in fresh MS medium. Rooted plantlets 5-7 cm tall were produced in 10-15 days. The leaves were removed from the plantlets, and the stems were cut into pieces 1 cm long. The pieces were then soaked as above for 15 min. in a few milliters of a culture of *Agrobacterium tumefaciens* that had been grown on a shaker overnight at 28C and contained either pCAMBIA1201 or pVZA100. The pieces were blotted on sterile filter paper and the tissue culture procedure of Cearley and Bolyard (1997) was followed. Bulbous tuber-like and root-like structures were produced (FIG. 8), but no plants were regenerated and rooted, despite testing of many media. For biolistic transformation, potato plantlets 3-5 cm tall were transplanted to soil. After 2-3 days they were bombarded using the hand held homemade particle gun and gold particles coated with either pCAMBIA1201, pVZA100, pVZA200, pVZA300 or pVZA400 or with no DNA. The plants were grown in the greenhouse and assayed by PCR and for their reactions to aphids and *P. infestans*.

Example 8

DNA and RNA Extraction from Plant and Fungal Tissues and PCR and RT/PCR Protocols Total DNA was extracted from tobacco leaf tissue and mycelium of *Phytophthora nicotianae* by the method of Dellaporta et al., 1983. Usually a 100 mg sample of frozen tissue was ground to a fine powder in a microfuge tube containing liquid nitrogen, and then homogenized in 500 ul of extraction buffer with a motor-driven stainless steel pestle.

Total RNA for RT/PCR reactions was extracted from leaf tissue and fungal mycelium by the TRIzol method of Invitrogen. Usually 100 mg of tissue was frozen in liquid nitrogen in a 1.8 ml microfuge tube. It was ground to fine powder and then homogenized in 1.0 ml of TRIzol with a motor-driven pestle. The mixture was allowed to incubate for 5 min. at room temperature. Then 200 ul of chloroform were added and mixed by vortexing. The suspension was incubated 5 min. at room temperature. The tubes were centrifuged at 14,000 rpm for 15 min. at 4° C. The aqueous phase was transferred to a clean tube, 500 ul of isopropanol were added and the samples mixed and incubated 10 min. at room temperature. The tubes were centrifuged again for 10 min. at 4° C., and the supernatant was discarded. The pellet was rinsed once with 250 ul of 75% ethanol by vortexing and centrifuging 5 min. at 4° C. The RNA pellet was air dried briefly, dissolved in 20 ul of RNase-free water and stored at −70° C. until used.

A similar method was used for large preparations of total RNA for siRNA detection. Usually 1 gram of frozen leaf or fungal mycelium was ground to fine powder in liquid nitrogen and homogenized with 15 ml TRIzol reagent. Then 3 ml of chloroform were added and incubated as above. The supernatant was recovered by centrifugation and the RNA precipitated with ½ volume of isopropanol. The pellet was washed with 75% ethanol, air dried and resuspended in 80 ul of RNase-free water.

The PCR reactions for both plant and fungal tissues were performed essentially as described by Munoz and Bailey, 1998, except the reaction volumes totaled 50 ul. The reactions contained 1×PCR buffer (10× solution: 500 mM KCl, 100 mM Tris-HCl pH 9.0, and 1% Triton X-100), 2.5 mM $MgCl_2$, 200 μM of each deoxyribonucleotide triphosphate (dNTP), 2.5 units of Taq DNA polymerase (Invitrogen or Promega), 100 pmol of the appropriate forward and reverse oligonucleotide primer, 1-10 ul of template and sufficient deionized water to equal 50 ul. DNA preparations used as templates were usually diluted to 50 ng per microliter, and 1 microliter was used as the template.

The PCR reaction conditions were standardized except for the annealing temperature, which was varied depending on the Tm of the oligonucleotide primers for the gene being amplified. The standardized conditions were 94° C. for 2 min. for melting, followed by 40 cycles of 1 min. at 94° C., 1 min. at the annealing temperature, and 2 min. at 72° C. for elongation. After 40 cycles there was 10 min. elongation at 72° C., and the reactions were held at 4° C. until assayed.

The RT/PCR reactions were carried out in 3 separate steps, DNase treatment, reverse transcription and then PCR, as recommended by Invitrogen. The DNAse treatment was performed to eliminate any DNA carried over in the RNA purification to ensure that only messenger RNA was being transcribed, and not the genomic DNA. The DNase mix contained per reaction: 3 ug of RNA, 1 ul 10×DNAse I buffer, 2 ul DNAse I, 0.5 ul RNase OUT and water (RNase-free) to 10 ul final volume. This was incubated at 26° C. for 30 min. Then 6.5 ul of 25 mM EDTA were added per tube and incubated for 15 min. at 65° C.

For the reverse transcriptase (RT) reactions a Mix I and Mix II were prepared. Mix I contained per reaction: 1 ul dNTPs, 4 ul 5×RT buffer, and 2 ul dithiothreitol. Mix II contained per reaction: 0.5 ul RNase OUT, 1 ul reverse transcriptase and 1 ul water. The appropriate oligonucleotide primers (1 ul each or water) were placed in the appropriate tubes and Mix I and II added appropriately. Mix I was placed in every tube, Mix II in the odd numbered tubes and 2.5 ul water in the even numbered tubes; then 10 ul of DNase treated RNA was added to each tube. The RT reactions were incubated at 42° C. for 60 min., and then at 70° C. for 15 min.

Example 9

Detection of siRNAs in Plant and Fungal Tissues

The procedure was essentially as described by Hutvagner et al., 2000. Total RNA was extracted from tobacco leaves or fungal mycelium as above. It was quantitated in a spectrophotometer at 260 nm and 80 ug were fractionated by denaturing polyacrylamide gel electrophoresis on 15% gels for 2.5 hrs at 0.025 Amp. The gels were stained with ethidium bromide, photographed, and the RNA transferred to hybond $N^+$ (Amersham) for 1 hr. at 10 volts at 4° C. Hybridization was performed as described by Sambrook et al. (1989) for Northern blotting.

The probe was transcribed from a 500 by PCR product of the cutinase gene and labeled with $^{32}P$ by random priming. Membranes were prehybridized 1 hr at 50° C. with HYBAID buffer solution from Amersham and hybridized for at least 16 hrs at 50° C. Washes were performed twice with 5×SSC at room temperature. The hybridization signals were detected by phosphorimaging, using a Storm 860 phosphorimager scanner from Molecular Dynamics.

Example 10

GUS Staining of Plant and Fungal Tissues

Preparation of the X-GLUC substrate: For 200 ml, set up a beaker with 150 ml distilled water and add the following components: Sodium phosphate buffer pH 7.0 (1 M), 20 ml, EDTA pH 8.0 (500 mM), 4 ml, Potassium ferrocyanide $K_4Fe(CN)_6.3H_2O$, 0.042 g, Triton X-100 0.2 ml. Stir for 10 min. Adjust pH 7.0 with NaOH. Dissolve 100 mg of X-GLUC in 2 ml DMSO or dimethyl-formamide. Add the X-GLUC in DMSO to the beaker. Filter sterilize the solution, dispense in 10 ml aliquots, and store at −20° C. For incorporation into growth media, add 100 mg of X-GLUC powder dissolved in DMSO to 250 ml V8 agar cooled and ready to dispense for fungal isolates or to MS media for plant materials.

Staining procedure: Add enough X-GLUC solution to cover the small explant of plant tissue and incubate at 37° C. for 3-24 hours. For fungal isolates or plant materials in X-gluc agar plates, incubate at 24-27° C. for 3-24 hours.

This procedure is essentially as described by Jefferson, et al., 1986.

Example 11

Plant Inoculation Tests with Fungi

Three methods were tested to inoculate tobacco with *P. nicotianae*. All gave satisfactory results, but the toothpick method was more rigorous and more dependable.

1. Toothpick method: This method was provided by Dr. A. Csinos (personal communication). Round wooden toothpicks were broken in half and autoclaved in V-8 broth. The sterile toothpicks were laid flat in plates of V-8 agar, and 6-8 mycelial discs (5 mm in diameter) of *P. nicotianae* were spaced equidistant on the plate. The plates were incubated at 27C for at least 2 weeks, when chlamydospores become obvious by microscopic examination. Plant inoculation is accomplished by standing 1 or 2 toothpicks in the soil next to the crown of the plant. The plants were covered with a plastic tent to maintain relative humidity at 100% and incubated at 27° C. Symptoms were usually apparent after 2-4 days, and susceptible plants were usually dead after 5-8 days. The reactions of resistant transgenic plants vary from being symptomless to producing restricted stem lesions 1-4 cm long, which do not interfere with plant growth and subsequent flower and seed development.

2. The mycelial soak method: Mycelia of *P. nicotianae* were grown overnight at 27° C. in V-8 broth. Transgenic seedlings or plants in soil were washed free of the medium and placed in 100 ml of sterile deionized water. Mycelial mats were shredded with forceps and added to the water. The plants were covered with a plastic tent to maintain relative humidity at 100% and incubated at 27° C. Symptoms were usually apparent after 2-4 days, and susceptible plants were usually dead after 5-8 days. The roots and crown of the susceptible plants were completely macerated (FIG. 11A). The roots of the resistant transgenic plants appear to be "burned" at the tips (FIG. 11B), or there were defined lesions at the crown, but this does not interfere with plant growth and subsequent flower and seed development after the plants were potted in soil.

3. Zoospore inoculation: Abundant sporangia were produced by placing strips of surface-sterilized tobacco leaves in growing cultures of *P. nicotianae* at 27° C. in V-8 broth overnight. Millions of zoospores were released, by placing the mats in sterile demineralized water and chilled at 4° C. for 30-60 min. Zoospores were collected by centrifugation for 5 min. at 5,000 g and 4° C.

Soybean plants were inoculated with *P. sojae* by two different methods. Seedlings were inoculated by cutting a 3 mm cylinder from an actively growing culture on V8 agar with a cork borer and placing the cylinder in the axil of one hypocotyl. The inoculum was held in place by Parafilm, and the plants enclosed in a plastic bag to give 100% humidity. Leaves of soybean plants were inoculated with *P. sojae* by placing a leaf in a Petri dish withl0 ml of sterile water and adding 1 or 2 plugs of inoculum as above.

Potato leaves were inoculated with *P. infestans* by placing a leaf in a Petri dish with 10 ml of sterile water and adding 1 or 2 plugs of inoculum as above, or by placing 10 ul of a zoospore suspension per leaflet.

In all inoculation tests, the plant or leaf reactions were read and recorded daily until the inoculated plants or leaves stopped dying or showed no evidence of infection.

Example 12

Molecular Characterization of *P. nicotianae* Resistant Tobacco Plants

DNA and RNA were extracted from T0 and T2 generation transformed plants of Example 27. Polymerase chain reaction (PCR) and reverse transcription/PCR(RT/PCR) tests were performed on the DNA and RNA samples, respectively. The PCR reactions were performed to determine the presence of the transgenes in the plants. The RT/PCR reactions were performed to determine if the transgenes were being expressed or had been silenced. The results were the same for both the T0 and T2 generations, and are summarized in Table 7.

TABLE 7

Gene Detection and Expression in Transgenic and Wild Type Tobacco Plants

| | Hygromycin phosphotransferase | | GUS | |
|---|---|---|---|---|
| Tissue Assayed | PCR | RT-PCR | PCR | RT-PCR |
| Tobacco wild type | − | − | − | − |
| Tobacco + pCAMBIA1201 | + | + | + | + |
| pVZA100 Transgenic line 4 | + | + | + | − |
| pVZA100 Transgenic line 23 | + | + | + | − |
| pVZA100 Transgenic line 26 | + | + | + | − |
| pVZA100 Transgenic line 27 | + | + | + | − |
| pVZA100 plasmid DNA | + | na | + | na |

| | Cutinase | | 16S Ribosomal RNA | |
|---|---|---|---|---|
| Tissue Assayed | PCR | RT-PCR | PCR | RT-PCR |
| Tobacco wild type | − | − | + | + |
| Tobacco + pCAMBIA1201 | − | − | + | + |
| pVZA100 Transgenic line 4 | + | − | + | + |
| pVZA100 Transgenic line 23 | + | − | + | + |
| pVZA100 Transgenic line 26 | + | − | + | + |
| pVZA100 Transgenic line 27 | + | − | + | + |
| pVZA100 plasmid DNA | + | na | − | na |

+ = Positive (gel band)
− = Negative (no gel band)
na = Not applicable

In the upper panel of Table 7, the data in the first column demonstrate that the hygromycin resistance gene (hygromycin phosphotransferase) was not present in the wild type tobacco plants, but it was present in all the plants transformed with either the pCAMBIA 1201 plasmid alone or with pVZA100. The data in the second column demonstrate that the hygromycin phosphotransferase gene was expressed in all plants in which it was present. The data in the third column demonstrate that the GUS gene was not present in the wild type tobacco plants, but it was present in all the plants transformed with either the pCAMBIA 1201 plasmid alone or with pVZA100. The data in the fourth column demonstrate that the GUS gene was expressed only in the pCAMBIA 1201 transformed plants, where no GUS silencing construct was present. However, GUS was silenced in all transgenic plants containing the pVZA100 silencing construct.

In the lower panel of Table 7, the data in the first column demonstrate that the fungal cutinase gene was not present in the wild type tobacco plants, nor in those plants transformed with the pCAMBIA 1201 plasmid alone. However, it was present in all the plants transformed with pVZA100. The data in the second column demonstrate that the fungal cutinase gene was not expressed in either the wild type plants or in those plants transformed with either the pCAMBIA 1201 plasmid alone or with pVZA100. The data in the third column demonstrate that the 16S ribosomal RNA gene was present in the wild type and all of the transgenic tobacco plants, but not in the silencing construct. The data in the fourth column demonstrate that the 16S ribosomal RNA gene was expressed in all of the tobacco plants, whether wild type or transgenic.

When the wild type tobacco plants or those transformed with pCAMBIA1201 were inoculated with *P. nicotianae*, they were always susceptible, whereas those transformed with pVZA100, such as transgenic lines 4, 23, 26 and 27 were resistant (FIGS. 11A and B, respectively).

Example 13

Fungal Transformation and Characterization

Different cultures of either *P. nicotianae* or *P. sojae* are bombarded with either pCAMBIA1201, pVZA100, pVZA200, pVZA300, or pVZA400 as above, and single zoospore cultures are produced from the viable cultures.

Those *P. nicotianae* cultures bombarded with pCAMBIA1201 and pVZA100 were tested for pathogenicity on the normally susceptible wild type Xanthi tobacco. Those cultures transformed with pCAMBIA1201 remained pathogenic, whereas those cultures transformed with pVZA100 were nonpathogenic. Wild type and transgenic cultures of *P. nicotianae* were grown in liquid V8 medium and DNA and RNA were extracted as described above. Those samples were analyzed by PCR and RT/PCR as above. The results are summarized in Table 8.

TABLE 8

Gene Detection and Expression in Transgenic and Wild Type *Phytophthora nicotianae*

| Tissue Assayed | Hygromycin phosphotransferase PCR | Hygromycin phosphotransferase RT-PCR | GUS PCR | GUS RT-PCR |
|---|---|---|---|---|
| *P. nicotianae* wild type | − | − | − | − |
| *P. nicotianae* + pCAMBIA 1201 | + | + | + | + |
| *P. nicotianae* + pVZA100 | + | + | + | − |
| pVZA100 plasmid DNA | + | na | + | na |

TABLE 8-continued

Gene Detection and Expression in Transgenic and Wild Type *Phytophthora nicotianae*

| Tissue Assayed | Cutinase PCR | Cutinase RT-PCR | 16S Ribosomal RNA PCR | 16S Ribosomal RNA RT-PCR |
|---|---|---|---|---|
| *P. nicotianae* wild type | + | + | + | + |
| *P. nicotianae* + pCAMBIA 1201 | + | + | + | + |
| *P. nicotianae* + pVZA100 | + | − | + | + |
| pVZA100 plasmid DNA | + | na | − | na |

+ = Positive (gel band)
− = Negative (no gel band)
na = Not applicable

In the upper panel of Table 8, the data in the first column demonstrate that the hygromycin phosphotransferase gene was not present in the wild type *P. nicotianae*, but it was present in those cultures of *P. nicotianae* transformed with either the pCAMBIA 1201 plasmid alone or with pVZA100. The data in the second column demonstrate that the hygromycin phosphotransferase gene was expressed in all cultures in which it was present.

The data in the third column demonstrate that the GUS gene was not present in the wild type *P. nicotianae*, but it was present in those cultures of *P. nicotianae* transformed with either the pCAMBIA 1201 plasmid alone or with pVZA100. The data in the fourth column demonstrate that the GUS gene was being expressed only in the pCAMBIA 1201 transformed *P. nicotianae*, where no GUS silencing construct was present. However, GUS was silenced in all transgenic *P. nicotianae* cultures containing the pVZA100 silencing construct.

In the lower panel of Table 8, the data in the first column demonstrate that the fungal cutinase gene was present in the wild type *P. nicotianae*, as well as those cultures transformed with either the pCAMBIA 1201 plasmid alone or with the pVZA100 silencing construct, because cutinase is a constitutive gene of *P. nicotianae*. The data in the second column demonstrate that the fungal cutinase gene was expressed in both the wild type *P. nicotianae* as well as in the cultures transformed with the pCAMBIA 1201 plasmid. However, the cutinase expression was silenced in those *P. nicotianae* cultures transformed with the pVZA100 silencing construct.

The data in the third column demonstrate that the 16S ribosomal RNA gene was present in the wild type and all of the transgenic *P. nicotianae*, but not in the silencing construct. The data in the fourth column demonstrate that the 16S ribosomal RNA gene was being expressed in both the wild type and transgenic *P. nicotianae* cultures.

Figure 14:
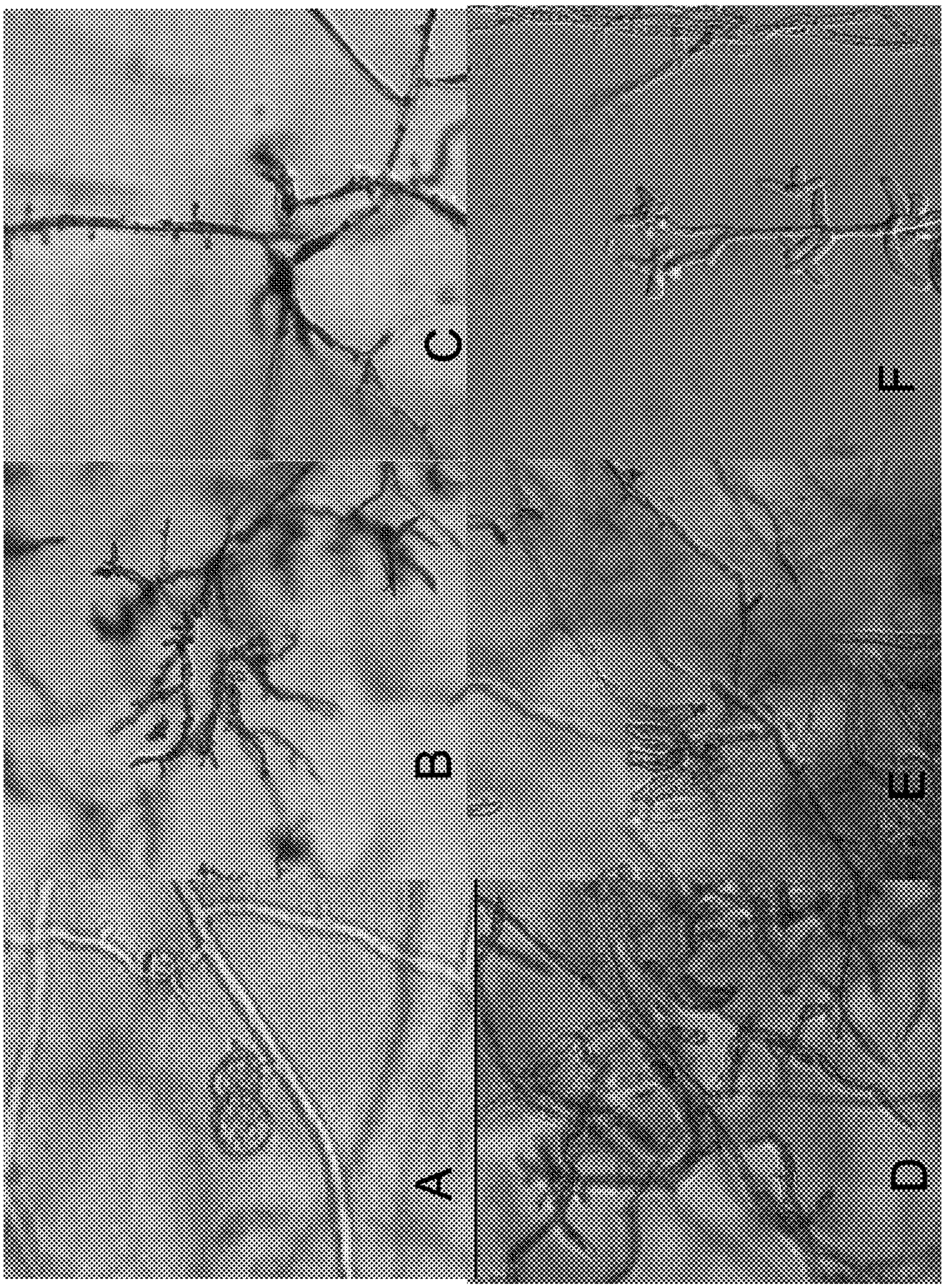
FIG. 14 shows the effects of pVZA300 and pVZA400 on the growth and development of transgenic *Phytophthora nicotianae* and *Phytophthora sojae.*
Figure 15:
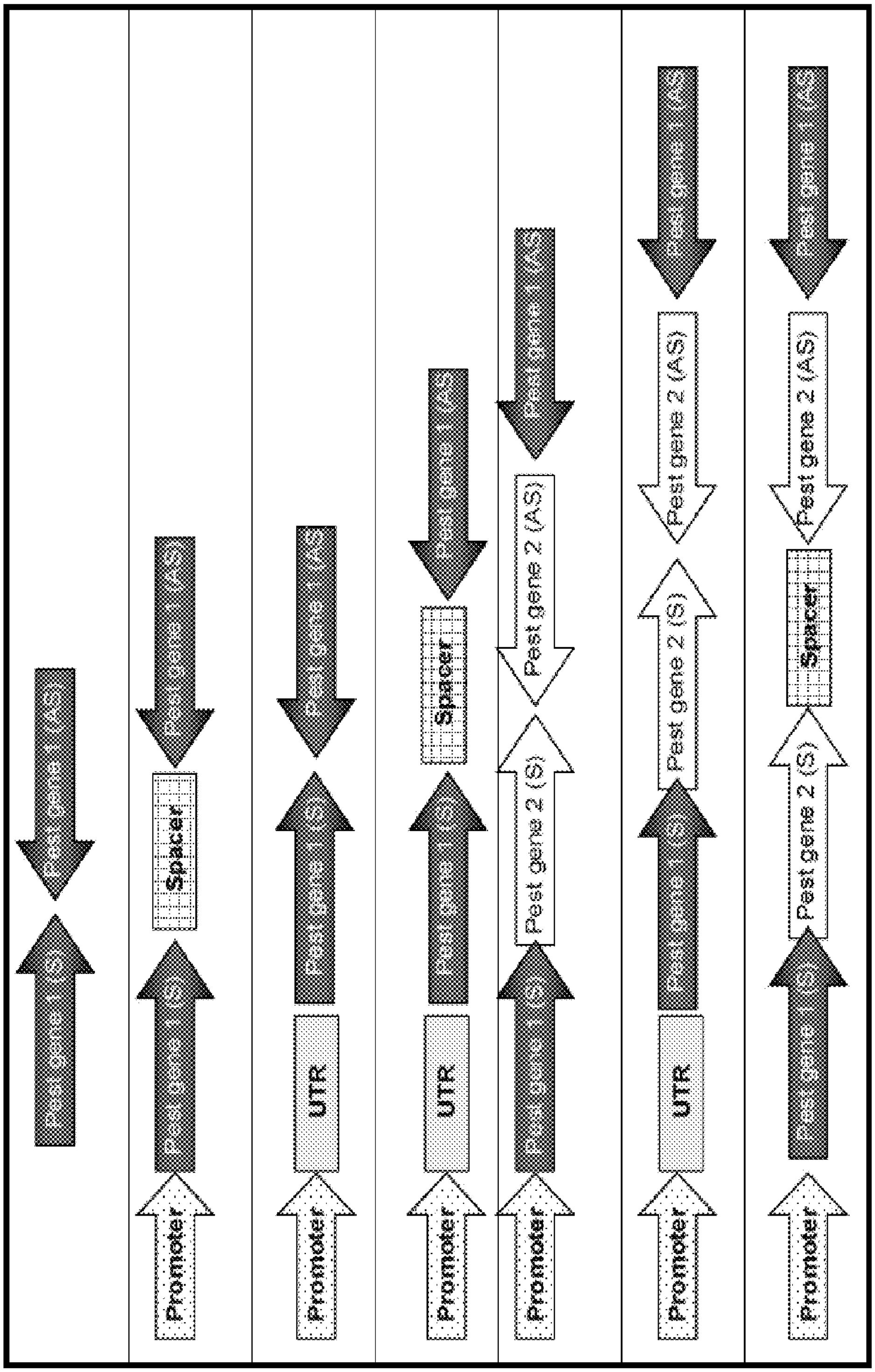
FIGS. 15-19 show heterologous polynucleotides designed in accordance with the present invention.
Figure 16:
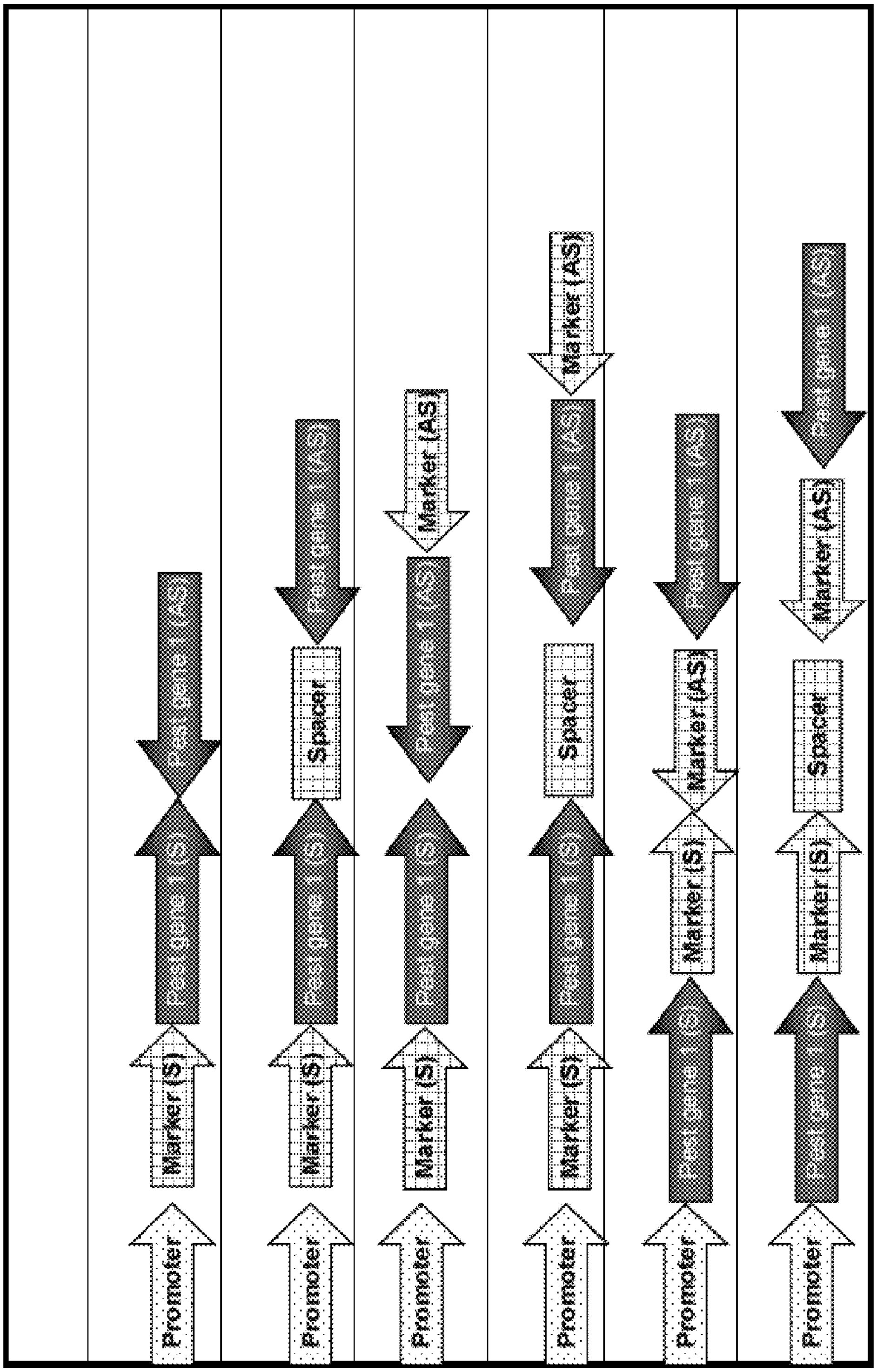
Figure 17:
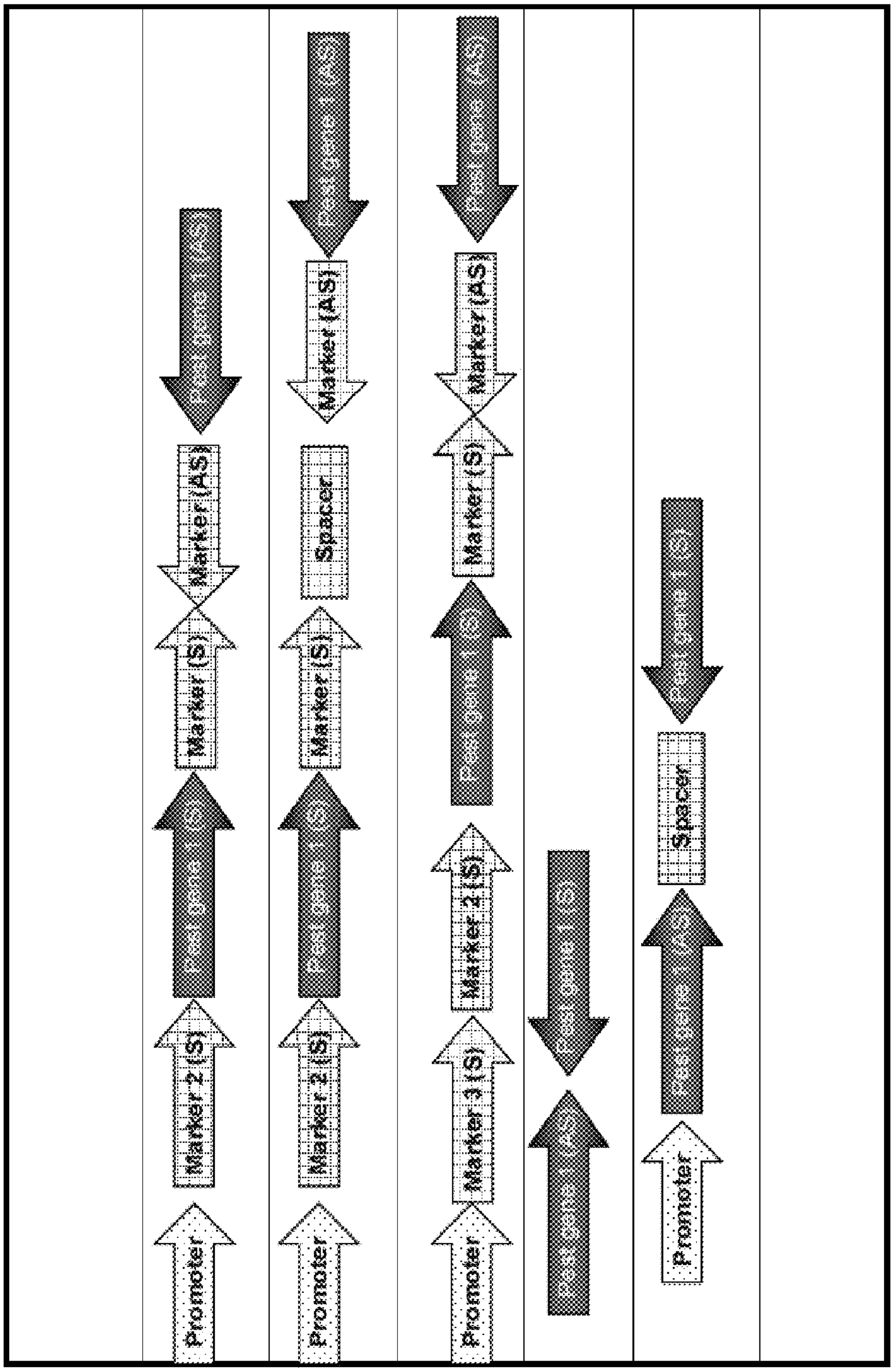
Figure 18:
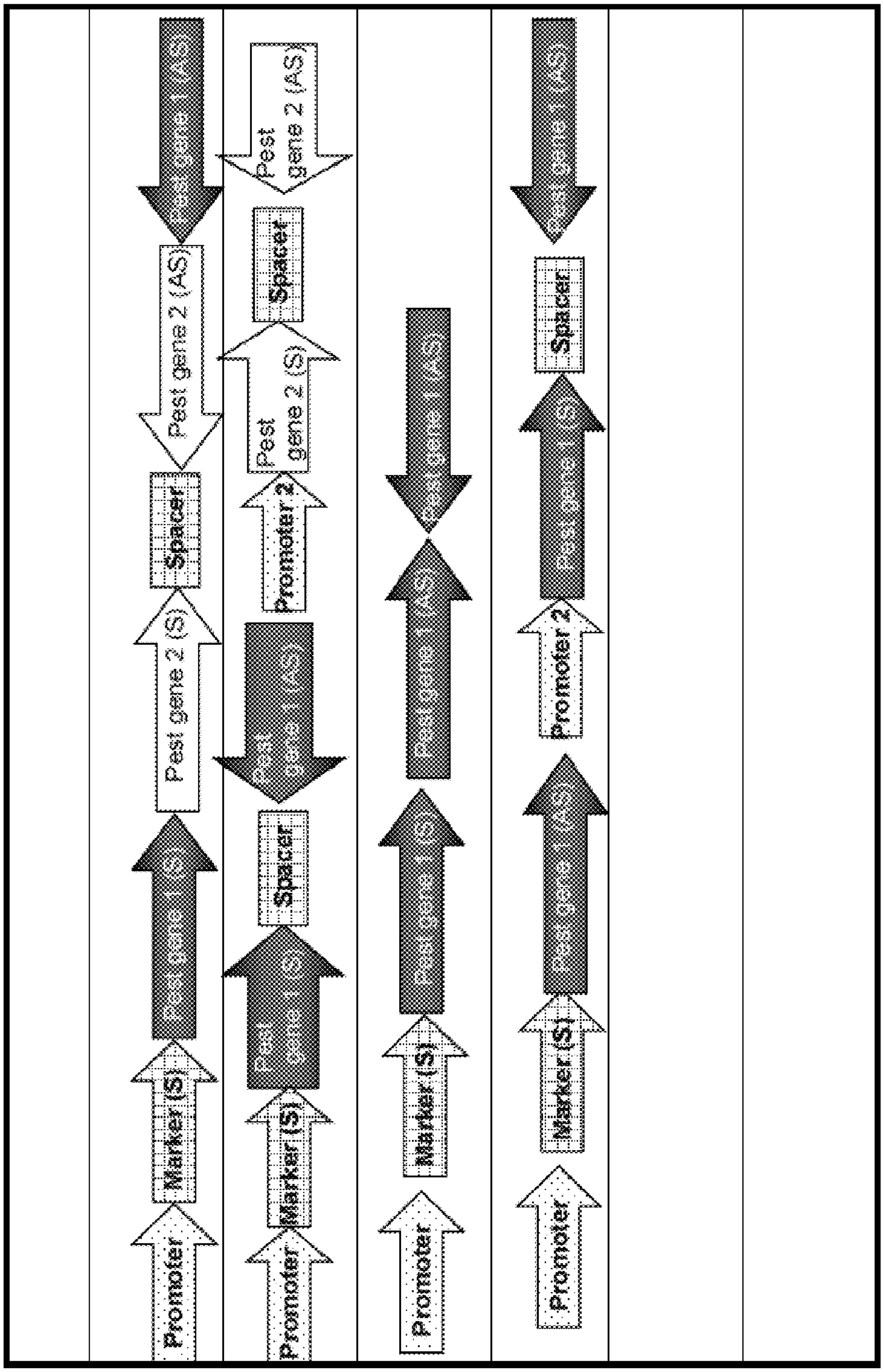
Figure 19:
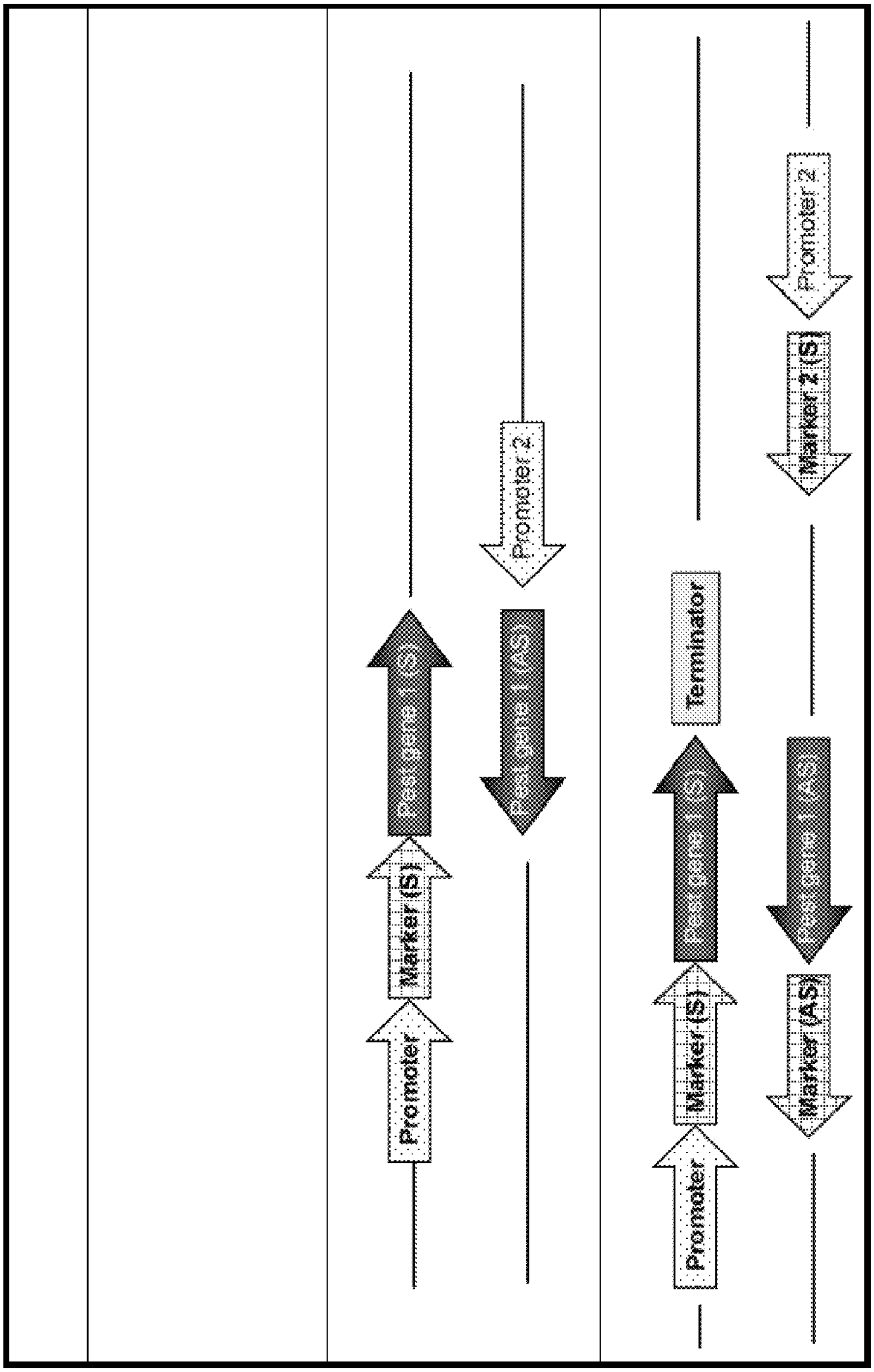

Microscopic examination of cultures of *P. nicotianae* and *P. sojae* bombarded with pCAMBIA1201, pVZA100 and pVZA200 indicated that all grew normally like the wild type and with no visual malformations (FIG. 14A). Similar results were observed for cultures of *P. nicotianae* reisolated from infected wild type tobacco or tobacco transformed with pVZA100. However, those cultures of *P. nicotianae* bombarded with pVZA300 or pVZA400 (FIG. 14 B, C, D) and those of *P. sojae* also bombarded with pVZA300 or pVZA400 (FIG. 14 E, F) grew very slowly, their hyphae were severely malformed, and some cultures died.

Transformation of *P. nicotianae* and *P. sojae* with pCAMBIA1201 and pVZA200 had no deleterious effects on the fungi because those plasmids do not contain fungal genes and cannot induce silencing in those fungi. Furthermore, transformation of *P. nicotianae* and *P. sojae* with pVZA100, which contains the *P. nicotianae* cutinase gene, allowed them to grow normally, but caused both species to become nonpathogenic, because the cutinase gene, which is essential for pathogenicity, was silenced by pVZA100.

Transformation of *P. nicotianae* and *P. sojae* with pVZA300 or pVZA400, which contain the *P. infestans* elicitin and ribosomal RNA genes, respectively, both had marked deleterious effects on the growth and development of both *P. nicotianae* and *P. sojae*. There was insufficient growth even to provide enough inoculum for pathogenicity tests. This suggests that the elicitin and ribosomal RNA genes were silenced in the transformed fungi, and that silencing either of these important genes is very detrimental or lethal to the fungi. This is further supported by the fact that both pVZA 200 and pVZA300 contain the *Myzus persicae* cathepsin gene. But in addition, pVZA300 contains the *P. infestans* elicitin gene. Since pVZA200 caused no visible effects, and pVZA300 caused detrimental effects, the elicitin gene appears to be responsible for the malformation caused by pVZA300.

As above, where *P. nicotianae* cutinase induced plant resistance to other species of *Phytophthora*, these results demonstrate that essential genes from one species of *Phytophthora* (*P. infestans*), when introduced in silencing constructs, can cause very detrimental effects on other species of *Phytophthora* (*P. nicotianae* and *P. sojae*), which should be useful in controlling *Phytophthora* spp. directly in plants or by depathogenesis of infested soil and fields.

Example 14

Demonstration of Gene Silencing in Tobacco by siRNA Detection

Further proof that gene silencing is occurring is the detection of the small interfering RNAs (siRNAs) in the purportedly silenced transformed plants (Examples 5 and 13) and transformed fungus (Example 13). The siRNAs are 21 to 25 nucleotides (nt) in length, with homology to the mRNA that is being "silenced".

Total RNA was extracted from wild type and purportedly silenced transgenic T0 and T1 generation tobacco plants and wild type and purportedly silenced *P. nicotianae*. The RNA was separated by polyacrylamide gel electrophoresis, blotted to a membrane and hybridized with a probe transcribed from a 500 by PCR product of the cutinase gene and labeled with $^{32}P$ by random priming. The hybridization and detection conditions were as in Example 9 above.

Figure 4B:
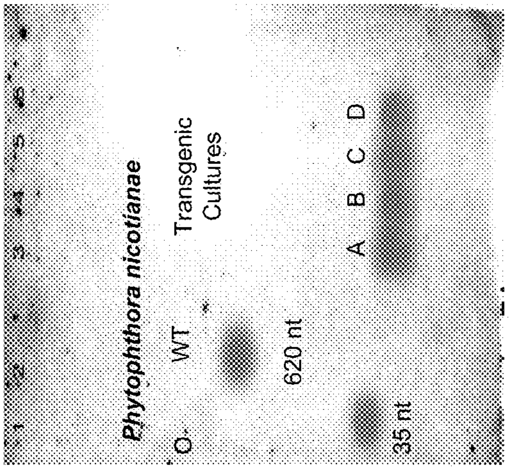
FIGS. 4A and 4B show the results of hybridization of the cutinase gene probe to siRNAs from wild type and transgenic tobacco plants and *P. nicotianae*, respectively.
Figure 4A:
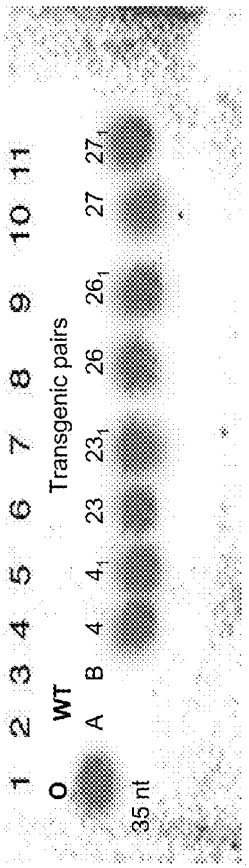

FIGS. 4*a* and 4*b* show the results of hybridization of the cutinase gene probe to RNAs from wild type and transgenic tobacco plants and transgenic *P. nicotianae*. In FIG. 4*a*, lane 1 shows hybridization to a mixture of the 35 nt oligonucleotides VZA 3F (SEQ ID NO: 3) VZA 4R (SEQ ID NO: 4). These were used to prime the PCR reaction to synthesize the template for production of the probe. Therefore, they are completely homologous to the template, and also of a known molecular size. Lanes 2 and 3 contain RNA from wild type tobacco plants. There is no hybridization because neither the cutinase gene nor the silencing construct are present in wild type plants, hence no siRNAs are produced. Lanes 4 to 11 contain the RNA from T0 and T1 generation plants of transgenic lines 4, 23, 26 and 27. The hybridization demonstrates the presence of the siRNAs in each of the transgenic plants, indicating the degradation of the cutinase mRNA, and the concomitant silencing of the cutinase gene in the transgenic plants.

In FIG. 4*b*, lane 1 again shows hybridization to a mixture of the 35 nt oligonucleotides VZA 3F and VZA 4R. Lane 2 shows hybridization to the RNA from the wild type *P. nicotianae*. The intense spot 620 nt in length corresponds to the full length transcript of the cutinase gene in wild type *P. nicotianae*. The cutinase gene is constituitive in this culture, and no silencing construct is present. Therefore, the full length mRNA transcript survives and is not digested to siRNAs. Lanes 3 to 6 contain the RNA from four cultures of *P. nicotianae* transformed with the silencing construct. The hybridization demonstrates the presence of siRNAs in each of the transgenic cultures of *P. nicotianae*, indicating the degradation of the cutinase mRNA, and the concomitant silencing of the cutinase gene in the transgenic *P. nicotianae*.

Biological evidence for the silencing of the essential cutinase gene in transgenic *P. nicotianae* comes from the fact that those cultures transformed with the cutinase gene silencing construct, pVZA100, are rendered non-pathogenic, whereas those cultures transformed with the pCAMBIA 1201 plasmid alone remain equally pathogenic to the wild type cultures from which they were derived. Further evidence of gene silencing in the presence of the pVZA100 silencing construct is provided by the GUS gene. The GUS reaction was always positive in those cultures that were transformed with pCAMBIA1201 and were pathogenic. Whereas it was always negative in those cultures that were transformed with pVZA100 and were nonpathogenic. This correlates directly with the activity or silencing of the cutinase gene in the same culture.

Example 15

Highly Homologous *Phytophthora* Cutinase Sequences Useful Herein

Analysis of *Phytophthora* gene sequences provides a basis for designing heterologous polynucleotides that confer cross-species resistance. As an illustration of the use of bioinformatic analysis to select pest pathogenicity gene sequences useful according to the present invention, 25 different isolates of *Phytophthora* were cloned and sequenced. Isolates included the nine species *P. capsici, P. cinnamomi, P. citricola, P. citrophthora, P. hevea, P. megakarya, P. megasperma* (*P. sojae*), *P. nicotianae* and *P. palmivora*. Each of these sequences (See SEQ ID NOs: 13 to 37) are useful for polynucleotides of the present invention.

For example, nine of the sequences are identical and 11 are >99% identical to the cutinase gene sequence of *P. nicotianae*. A shaded letter indicates a difference in sequence.

TABLE 9

| The nucleotide sequences of the cutinase genes of 25 isolates comprising 9 species of *Phytophthora* |
|---|
| (VZA 1 65R = Pnic Ri) |
| (SEQ ID NO: 13) |
| TCATACCATCTCGACAATGCCTCGAACTTGTCCTTCGGCAACGGCTTCGT |
| CATCGCGTCGGCGATCATGTCGTCGGTACCAACATGGCGAATCCGTAGCT |
| GCTCGTCCTCCACTAGGTGGCGCACCAAGTGGAACTTGTTCATAATGTGC |
| TTGCTCTTGCTGTGCTTGCCAGGCTTGGCAGTCAGGTAGATGCACGACAT |
| GTTATCACCGAATATCTCCGGAGTCGCAAACTCCCAGCATAGTTCGTCAC |
| AGAGTCCACGTAGCCACTGTAGATCTCTGGTACCTTCATTCATAGCAATA |
| TACTCTGCTTCCGTCGTGCTCTGTGCGTTGATCTCTTGCTTTCTTGATCC |
| GTACGAAACCACGTTACCATTGACGAACGTCACGAACCCACTAACACTCT |
| TTCGGTCATCAGGGTCATTAGCGTAGTCAGCATCGGTGTA |

TABLE 9-continued

The nucleotide sequences of the cutinase genes of 25 isolates comprising 9 species of *Phytophthora*

(VZA 2 69F = Pnic 21)

(SEQ ID NO: 14)

ACCATCTCGACAATGCCTCGAACTTGTCCTTCGGCAACGGCTTCGTCATC

GCGTCGGCGATCATGTCGTCGGTACCAACATGGCGAATCCGTAGCTGCTC

GTCCTCCACTAGGTGGCGCACCAAGTGGAACTTGTTCATAATATGCTTGC

TCTTGCTGTGCTTGCCAGGCTTGGCAGTTAGATAGATGCACGACATGTTA

TCGCCGAGTATCTCCGGAGTCGCAAACTCCCAGCATAGTTCGTCACAGAG

TCCACGTAGCCACTGTAGATCTCTGGTACCTTCATTCATAGCAATATACT

CTGCTTCCGTTGTGCTCTGTGCGTTGATCTCTTGCTTTCTTGATCCGTAC

GAAACCACATTGCCATTGACGAACGTCACGAACCCGCTAACACTCTTTCG

GTCATCAGGGTCATTAGCGTAGTCAGCATCGGTGTAGCACGTCAGATTCA

CG (VZA 3 73F = Pnic 23)

(SEQ ID NO: 15)

TCATACCATCTCGACAATG CTCAAACTTGTCCTTCGGCAACGGCTTCAT

CATCGCGTCGGCTATCATGTCGTCGGTGCCAACATGGCGAATCCGTAGCT

GCTCGTCCTCCACTAGGTGGCGCACCAAGTGAAACTTGTTCATAATGTGC

TTGCTCTTGCTGTGCTTGCCAGGCTTGGCAGTCAGGTAGATGCACGACTT

GTTATCGCCGAGTATCTCCGGAGTCGCAAACTCCCAGCATAGTTCTTCAC

AGAGTCCACGTAGCCACTGTAGATATCTGGTACCTTCATTCATAGCAATA

TACTCTGCTTCCGTTGTACTCTGTACGTTGATCTCTTGCTTCCTTGATCC

GTACGAAACCACATTGCCATTGACGAACGTCACGAACCC (VZA 4 88F = Pnic 17)

(SEQ ID NO: 16)

TCATACCATCACGACAATGCCTCGAACTTGTCCTTCGGCAACGGCTTCGT

CATCGCGTCGGCGATCATGTCGTCGGTACCAACATGGCGAATCCGTAGCT

GCTCGTCCTCCACTAGGTGGCGCACCAAGTGGAACTTGTTCATAATATGC

TTGCTCTTGCTGTGCTTGCCAGGCTTGGCAGTTAGATAGATGCACGACAT

GTTATCGCCGAGTATCTCCGGAGTCGCAAACTCCCAGCATAGTTCGTCAC

AGAGTCCACGTAGCCACTGTAGATCTCTGGTACCTTCATTCATAGCAATA

TACTCTGCTTCCGTTGTGCTCTGTGCGTTGATCTCTTGCTTTCTTGATCC

GTACGAAACCACATTGCCATTGACGAACGTCACGAACCCGCTAACACTCT

TTCGGTCATCAGGGTCATTAGCGTAGTCAGCATCGGTGTAGCACGTCAGA

TTCACGTCGTTCCCGGG (VZA 5 62R = Pcap Ri)

(SEQ ID NO: 17)

TCATACCATCTCGACAATGCCTCGAACTTGTCCTTCGGCAACGGCTTCGT

CATCGCGTCGGCGATCATGTCGTCGGTACCAACATGGCGAATCCGTAGCT

GCTCGTCCTCCACTAGGTGGCGCACCAAGTGGAACTTGTTCATAATATGC

TTGCTCTTGCTGTGCTTGCCAGGCTTGGCAGTTAGATAGATGCACGACAT

GTTATCGCCGAGTATCTCCGGAGTCGCAAACTCCCAGCATAGTTCGTCAC

AGAGTCCACGTAGCCACTGTAGATCTCTGGTACCTTCATTCATAGCAATA

TABLE 9-continued

The nucleotide sequences of the cutinase genes of 25 isolates comprising 9 species of *Phytophthora*

TACTCTGCTTCCGTTGTGCTCTGTGCGTTGATCTCTTGCTTTCTTGATCC

GTACGAAACCACATTGCCATTGACGAACGTCACGAACCCGCTAACACTCT

TTCGGTCATCAGGGTCATTAGCGTAGTCAGCATCGGTGTAGCACGTCAGA

TTCACGTCGTTCCCG (VZA 6 70F = Pcap 30)

(SEQ ID NO: 18)

CCATCTCGACAATGCCTCGAACTTGTCCTTCGGCAACGGCTTCGTCATCG

CGTCGGCGATCATGTCGTCGGTACCAACATGGCTAATCCGTAGCTGCTCG

TCCTCCACTAGGTGGCGCACCAAGTGGAACTTGTTCATAATATGCTTGCT

CTTGCTGTGCTTGCCAGGCTTGGCAGTTAGATAGATGCACGACATGTTAT

CGCCGAGTATCTCCGGAGTCGCAAACTCCCAGCATAGTTCGTCACAGAGT

CCACGTAGCCACTGTAGATCTCTGGTACCTTCATTCATAGCAATATACTC

TGCTTCCGTTGTGCTCTGTGCGTTGATCTCTTGCTTTCTTGATCCGTACG

AAACCACATTGCCATTGACGAACGTCACGAACCCGCTAACACTCT (VZA 7 72F = Pcap 30)

(SEQ ID NO: 19)

CTATAACGACAATGCCTCGAACTGGGCCTTCGGCAACGGCTTCGTCATCG

CGTCGGCGATCATGTCGTCGGTACCAACATGGCGAATCCGTAGCTGCTCG

TCCTCCACTAGGTGGCGCACCAAGTGGAACTTGTTCATAATATGCTTGCT

CTTGCTGTGCTTGCCAGGCTTGGCAGTTAGATAGATGCACGACATGTTAT

CGCCGAGTATCTCCGGAGTCGCAAACTCCCAGCATAGTTCGTCACAGAGT

CCACGTAGCCACTGTAGATCTCTGGTACCTTCATTCATAGCAATATACTC

TGCTTCCGTTGTGCTCTGTGCGTTGATCTCCTGCTTTCTTGATCCGTACG

AAACCACATTGCCATTGACGAACGTCACGAACCCGCTAACACTCT (VZA 8 79F = Pcap 28)

(SEQ ID NO: 20)

ACCATCTCGACAATGCCTCGAACTTGTCCTTCGGCAACGGCTTCGTCATC

GCGTCGGCGATCATGTCGTCGGTACCAACATGGCGAATCCGTAGCTGCTC

GTCCTCCACTAGGTGGCGCACCAAGTGGAACTTGTTCATAATATGCTTGC

TCTTGCTGTGCTTGCCAGGCTTGGCAGTTAGATAGATGCACGACATGTTA

TCGCCGAGTATCTCCGGAGTCGCAAACTCCCAGCATAGTTCGTCACAGAG

TCCACGTAGCCACTGTAGATCTCTGGTACCTTCATTCATAGCAATATACT

CTGCTTCCGTTGTGCTCTGTGCGTTGATCTCTTGCTTTCTTGATCCGTAC

GAAACCACATTGCCATTGACGAACGTCACGAACCCGCTAACACTCTTTCG

GTCATCAGGGTCATTAGCGTAGTCAGCATCGGTGTAGCACGTCAGATTCA

CGTCGTTCCC (VZA 9 84F = Pcap 01)

(SEQ ID NO 21)

TAATACCA CTCGACAATGCATCGAACTTGACCTTCGGCAACGGCTTCGT

CATCGCGTCGGCATCATGTCGTCGGTACCAACATGCCGAATCCGTAGCTG

CTCGTCCTCCACTAGGTGGCGCACCAAGTGGAACTTGTTCATAATATGCT

TABLE 9-continued

The nucleotide sequences of the cutinase genes of 25 isolates comprising 9 species of *Phytophthora*

TGCTCTTGCTGTGCTTGCCAGGCTTGGCAATTAGATAGATGCACGACATG
TTATCGCCGAGTATCTCCGGAGTCGCAAACTCCCAGCATAGTTCGTCACA
GAGTCCACATAGCCACTGTAGATCTCTGGTACCTTCATTCATAGCAATAT
ACTCTGCTTCCGTTGCGCTCTGTGCGTTGAACCCTTGCTTTCTTGATCCT
CACTAAACCACATTGCCATTGACGAACGTCACTAACCCTCTAACACTCTT
TAGATCATTAATATCATTAGCCTAATCAACAAACTCCTAATACCTCAGAT
TCACTACAATCC (VZA 10 87F = Pcap 32)
(SEQ ID NO: 22)
TCATACCATCTCGACAATGCCTCGAACTTGTCCTTCGGCAACGGCTTCGT
CATCGCGTCGGCGATCATGTCGTCGGTACCAACATGGCGAATCCGTAGCT
GCTCGTCCTCCACTAGGTGGCGCACCAAGTGGAACTTGTTCATAATATGC
TTGCTCTTGCTGTGCTTGCCAGGCTTGGCAGTTAGATAGATGCACGACAT
GTTATCGCCGAGTATCTCCGGAGTCGCAAACTCCCAGCATAGTTCGTCAC
AGAGTCCACGTAGCCACTGTAGATCTCTGGTACCTTCATTCATAGCAATA
TACTCTGCTTCCGTTGTGCTCTGTGCGTTGATCTCTTGCTTTCTTGATCC
GTACGAAACCACATTGCCATTGACGAACGTCACGAACCCGCTAACACTCT
TTCGGTCATCAGGGTCATTAGCGTAGTCAGCATCGGTGTAGCACGTCAGA
TTCACGTCGTTCCCGGC (VZA 11 89F = Pcap 03)
(SEQ ID NO: 23)
TCATACCATCTCGACAATGCCTCGAACTTGTCCTTCGGCAACGGCTTCGT
CATCGCGTCGGCGATCATGTCGTCGGTACCAACATGGCGAATCCGTAGCT
GCTCGTCCTCCACTAGGTGGCGCACCAAGTGGAACTTGTTCATAATATGC
TTGCTCTTGCTGTGCTTGCCAGGCTTGGCAGTTAGATAGATGCACGACAT
GTTATCGCCGAGTATCTCCGGAGTCGCAAACTCCCAGCATAGTTCGTCAC
AGAGTCCACGTAGCCACTGTAGATCTCTGGTACCTTCATTCATAGCAATA
TACTCTGCTTCCGTTGTGCTCTGTGCGTTGATCTCTTGCTTTCTTGATCC
GTACGAAACCACATTGCCATTGACGAACGTCACGAACCCGCTAACACTCT
TCAGATTCACGTCGTT (VZA 12 90F = Pcap 22)
(SEQ ID NO: 24)
TCATACCATCTCGACAATGCCTCGAACTTGTCCTTCGGCAACGGCTTCGT
CATCGCGTCGGCGATCATGTCGTCGGTACCAACATGGCGAATCCGTAGCT
GCTCGTCCTCCACTAGGTGGCGCACCAAGTGGAACTTGTTCATAATATGC
TTGCTCTTGCTGTGCTTGCCAGGCTTGGCAGTTAGATAGATGCACGACAT
GTTATCGCCGAGTATCTCCGGAGTCGCAAACTCCCAGCATAGTTCGTCAC
AGAGTCCACGTAGCCACTGTAGATCTCTGGTACCTTCATTCATAGCAATA
TACTCTGCTTCCGTTGTGCTCTGTGCGTTGATCTCTTGCTTTCTTGATCC
GTACGAAACCACATTGCCATTGACGAACGTCACGAACCCGCTAACACTCT TABLE 9-continued The nucleotide sequences of the cutinase genes of 25 isolates comprising 9 species of *Phytophthora*

TTCGGTCATCAGGGTCATTAGCGTAGTCAGCATCGGTGTAGCACGTCAGA
TTCACGTCGTTCCCGG (VZA 13 91F = Pcap 25)
(SEQ ID NO: 25)
TCAAACCATCTCGACAATGCCTCGAACTTGTCCTTCGGCAACGGCTTCGT
CATCGCGTCGGCGATCATGTCGTCGGTACCAACATGGCAAATCCGTAGCT
GCTCGTCCTCCACTAGGTGGCGCACCAAGTGGAACTTGTTCATAATATGC
TTGCTCTTGCTGTGCTTGCCAGGCTTGGCAGTTAGATAGATGCACGACAT
GTTATCGCCGAGTATCTCCGGAGTCGCAAACTCCCAGCATAGTTCGTCAC
AGAGTCCACGTAGCCACTGTAGATCTCTGGTACCTTCATTCATAGCAATA
TACTCTGCTTCCGTTGTGCTCTGTGCGTTGATCTCTTGCTTTCTTGATCC
GTACGAAACCACATTGCCATTGACGAACGTCACGAACCCGCTAACACTC
TTTCGGTCATCAGGGTCATTAGCGTAGTCAGCATCGGTGTAGCACGTCAG
ATTCACGTCGTTCCCGGG (VZA 14 81F = Ppal 02)
(SEQ ID NO: 26)
TCATACCATCTCGACAATGCCTCGAACTTGTCCTTCGGCAACGGCTTCGT
CATCGCGTCGGCGATCATGTCGTCGGTACCAACATGGCGAATCCGTAGCT
GCTCGTCCTCCACTAGGTGGCGCACCAAGTGGAACTTGTTCATAATATGC
TTGCTCTTGCTGTGCTTGCCAGGCTTGGCAGTTAGATAGATGCACGACAT
GTTATCGCCGAGTATCTCCGGAGTCGCAAACTCCCAGCATAGTTCGTCAC
AGAGTCCACGTAGCCACTGTAGATCTCTGGTACCTTCATTCATAGCAATA
TACTCTGCTTCCGTTGTGCTCTGTGCGTTGATCTCTTGCTTTCTTGATCC
GTACGAAACCACATTGCCATTGACGAACGTCACGAACCCGCTAACACTCT
TTCGGTCATCAGGGTCATTAGCGTAGTCAGCATCGGTGTAGCACGTCAGA
TTCACGTCGTTCCCGG (VZA 15 82F = Ppal 10)
(SEQ ID NO: 27)
TCATACCATCTCGACAATGCCTCGAACTTGTCCTTCGGCAACGGCTTCGT
CATCGCGTCGGCGATCATGTCGTCGGTACCAACATGGCGAATCCGTAGCT
GCTCGTCCTCCACTAGGTGGCGCACCAAGTGGAACTTGTTCATAATATGC
TTGCTCTTGCTGTGCTTGCCAGGCTTGGCAGTTAGATAGATGCACGACAT
GTTATCGCCGAGTATCTCCGGAGTCGCAAACTCCCAGCATAGTTCGTCAC
AGAGTCCACGTAGCCACTGTAGATCTCTGGTACCTTCATTCATAGCAATA
TACTCTGCTTCCGTTGTGCTCTGTGCGTTGATCTCTTGCTTTCTTGATCC
GTACGAAACCACATTGCCATTGACGAACGTCACGAACCCGCTAACACTCT
TTCGGTCATCAGGGTCATTAGCGTAGTCAGCATCGGTGTAGCACGTCAGA
TTCACGTCGTTCCCG (VZA 16 83F = Ppal 11)
(SEQ ID NO: 28)
TCATACCATCTCGACAATGCCTCGAACTTGTCCTTCGGCAACGGCTTCGT
CATCGCGTCGGCGATCATGTCGTCGGTACCAACATGGCGAATCCGTAGCT TABLE 9-continued The nucleotide sequences of the cutinase genes of 25 isolates comprising 9 species of *Phytophthora*

GCTCGTCCTCCACTAGGTGGCGCACCAAGTGGAACTTGTTCATAATATGC
TTGCTCTTGCTGTGCTTGCCAGGCTTGGCAGTTAGATAGATGCACGACAT
GTTATCGCCGAGTATCTCCGGAGTCGCAAACTCCCAGCATAGTTCGTCAC
AGAGTCCACGTAGCCACTGTAGATCTCTGGTACCTTCATTCATAGCAATA
TACTCTGCTTCCGTTGTGCTCTGTGCGTTGATCTCTTGCTTTCTTGATCC
GTACGAAACCACATTGCCATTGACGAACGTCACGAACCCGCTAACACTCT
TTCGGTCATCAGGGTCATTAGCGTAGTCAGCATCGGTGTAGCACGTCAGA
TTCACGTCGTTCCCGGC (VZA17 85F = Ppal 04)
(SEQ ID NO: 29)
TCATACCATCTCGACAATGCCTCGAACTTGTCCTTCGGCAACGGCTTCGT
CATCGCGTCGGCGATCATGTCGTCGGTACCAACATGGCGAATCCGTAGCT
GCTCGTCCTCCACTAGGTGGCGCACCAAGTGGAACTTGTTCATAATATGC
TTGCTCTTGCTGTGCTTGCCAGGCTTGGCAGTTAGATAGATGCACGACAT
GTTATCGCCGAGTATCTCCGGAGTCGCAAACTCCCAGCATAGTTCGTCAC
AGAGTCCACGTAGCCACTGTAGATCTCTGGTACCTTCATTCATAGCAATA
TACTCTGCTTCCGTTGTGCTCTGTGCGTTGATCTCTTGCTTTCTTGATCC
GTACGAAACCACATTGCCATTGACGAACGTCACGAACCCGCTAACACTCT
TTCGGTCATCAGGGTCATTAGCGTAGTCAGCATCGGTGTAGCACGTCAGA
TTCACGTCGTTCCCGG (VZA 18 86F = Ppal 05)
(SEQ ID NO: 30)
TCATACCATCTCGACAATGCCTCGAACTTGTCCTTCGGCAACGGCTTCGT
CATCGCGTCGGCGATCATGTCGTCGGTACCAACATGGCGAATCCGTAGCT
GCTCGTCCTCCACTAGGTGGCGCACCAAGTGGAACTTGTTCATAATATGC
TTGCTCTTGCTGTGCTTGCCAGGCTTGGCAGTTAGATAGATGCACGACAT
GTTATCGCCGAGTATCTCCGGAGTCGCAAACTCCCAGCATAGTTCGTCAC
AGAGTCCACGTAGCCACTGTAGATCTCTGGTACCTTCATTCATAGCAATA
TACTCTGCTTCCGTTGTGCTCTGTGCGTTGATCTCTTGCTTTCTTGATCC
GTACGAAACCACATTGCCATTGACGAACGTCACGAACCCGCTAACACTCT
TTCGGTCATCAGGGTCATTAGCGTAGTCAGCATCGGTGTAGCACGTCAGA
TTCACGTCGTTCCCGGG (vza 19 64R = Pcin Ri)
(SEQ ID NO: 31)
TCATACCATCTCGACAATGCCTCGAACTTGTCCTTCGGCAACGGCTTCGT
CATCGCGTCGGCGATCATGTCGTCGGTACCAACATGGCGAAGCCGTTGCC
TCGTCCTCCACTAGGTGGCGCACCAAGTGGAACTTGTTCATAATATGCTT
GCTCTTGCTGTGCTTGCCAGGCTTGGCAGTTAGATAGATGCACGACATGT
TATCGCCGAGTATCTCCGGAGTCGCAAACTCCCAGCATAGTTCGTCACAG
AGTCCACGTAGCCACTGTAGATCTCTGGTACCTTCATTCATAGCAATATA
CTCTGCTTCCGTTGTGCTCTGTGCGTTGATCTCTTGCTTTCTTGATCCGT
ACGATTCGGTCATCAGGGTCATTAGCGTAGTCAGCATCGGTGTAGCACG
TCAGATTCACGTCGTTCCCGG (VZA 20 77F = Pcin 01)
(SEQ ID NO: 32)
ATCATCTCGACAATGCCTCGAACTTGTCCTTCGGCAACGGCTTCGTCATC
GCGTCGGCGATCATGTCGTCGGTACCAACATGGCGAAGCCGTACC TCG
TCCTCCACTAGGTGGCGCACCAAGTGGAACTTGTTCATAATATGCTTGCT
CTTGCTGTGCTTGCCAGGCTTGGCAGTTAGATAGATGCACGACATGTTAT
CGCCGAGTATCTCCGGAGTCGCAAACTCCCAGCATAGTTCGTCACAGAGT
CCACGTAGCCACTGTAGATCTCTGGTACCTTCATTCATAGCAATATACTC
TGCTTCCGTTGTGCTCTGTGCGTTGATCTCTTGCTTTCTTGATCCGTACG
AAACCACATTGCCATTGACGAACGTCACGAACCCGCTAACACTCTTTCGG
TCATCAGGGTCATTAGCGTAGTCAGCATCGGTGTAGCACGTCAGATTCAC
GTCGTTCCCGG (VXA 21 63R = Pcto Ri)
(SEQ ID NO: 33)
TCATACCATCTCGACAATGCCTCGAACTTGTCCTTCGGCAACGGCTTCGT
CATCGCGTCGGCGATCATGTCGTCGGTACCAACATGGCGAAGCCGT GC
CTCGTCCTCCACTAGGTGGCGCACCAAGTGGAACTTGTTCATAATATGC
TTGCTCTTGCTGTGCTTGCCAGGCTTGGCAGTTAGATAGATGCACGACAT
GTTATCGCCGAGTATCTCCGGAGTCGCAAACTCCCAGCATAGTTCGTCAC
AGAGTCCACGTAGCCACTGTAGATCTCTGGTACCTTCATTCATAGCAATA
TACTCTGCTTCCGTTGTGCTCTGTGCGTTGATCTCTTGCTTTCTTGATCC
GTACGAAACCACATTGCCATTGACGAACGTCACGAACCCGCTAACACTCT
TTCGGTCATCAGGGTCATTAGCGTAGTCAGCATCGGTGTAGCACGTCAGA
TTCACGTCGTTCCCGG (VZA 22 66R = Pctr Ri)
(SEQ ID NO: 34)
TCATACCATCTCGACAATGCCTCGAACTTGTCCTTCGGCAACGGCTTCGT
CATCGCGTCGGCGATCATGTCGTCGGTACCAACGTGGGATCG GCGTTGC
TCGTCCTCCACTAGGTGGCGCACCAAGTGGAACTTGTTCATAATATGCTT
GCTCTTGCTGTGCTTGCCAGGCTTGGCAGTTAGATAGATGCACGACATGT
TATCGCCGAGTATCTCCGGAGTCGCAAACTCCCAGCATAGTTCGTCACAG
AGTCCACGTAGCCACTGTAGATCTCTGGTACCTTCATTCATAGCAATATA
CTCTGCTTCCGTTGTGCTCTGTGCGTTGATCTCTTGCTTTCTTGATCCGT
ACGAAACCACATTGCCATTGACGAACGTCACGAACCCGCTAACACTCTTT
CGGTCATCAGGGTCATTAGCGTAGTCAGCATCGGTGTAGCACG (VZA 23 80F = Pmek 01)
(SEQ ID NO: 35)
TCATACCATCTCGACAATGCCTCGAACTTGTCCTTCGGCAACGGCTTCGT
CATCGCGTCGGCGATCATGTCGTCGGTACCAACATGGCGAATCCGTAGCT
GCTCGTCCTCCACTAGGTGGCGCACCAAGTGGAACTTGTTCATAATATGC TABLE 9-continued The nucleotide sequences of the cutinase genes of 25 isolates comprising 9 species of *Phytophthora*

```
TTGCTCTTGCTGTGCTTGCCAGGCTTGGCAGTTAGATAGATGCACGACAT
GTTATCGCCGAGTATCTCCGGAGTCGCAAACTCCCAGCATAGTTCGTCAC
AGAGTCCACGTAGCCACTGTAGATCTCTGGTACCTTCATTCATAGCAATA
TACTCTGCTTCCGTTGTGCTCTGTGCGTTGATCTCTTGCTTTCTTGATCC
GTACGAAACCACATTGCCATTGACGAACGTCACGAACCCGCTAACACTCT
TTCGGTCATCAGGGTCATTAGCGTAGTCAGCATCGGTGTAGCACGTCAGA
TTCACGTCGTTCCCGGCAA

(VZA 24 92F = Pmeg 01)
                                          (SEQ ID NO: 36)
CAGACCATCTCGACAATGCCTCGAACTTGTCCTTCGGCAACGGCTTCGTC
ATCGCGTCGGCGATCATGTCGTCGGTACCAACATGGCTAATCC TAGCTG
CTCATCCTCCACTAGGTGGCGCACCAAGTGGAACTTGTTCATAATATGCT
TGCTCTTGCTGTGCTTGCCAGGCTTGGCAGTTAGATAGATGCACGACATG
TTATCGCCGAGTATCTCCGGAGTCGCAAACTCCCAGCATAGTTCGTCACA
GAGTCCACGTAGCCACTGTAGATCTCTGGTACCTTCATTCATAGCAATAT
ACTCTGCTTCCGTTGTGCTCTGTGCGTTGATCTCTTGCTTTCTTGATCCC
TACGAAACCACATTGCCATTGACGAACGTCACGAACCCGCTAACACTCTT
TCGGTCATCAAGGTCATTAGCGTAGTCAGCATCGGTGTAGCACGTCAGAT
TCACGTCGTTCCCG

(VZA 25 93F = Phev 02)
                                          (SEQ ID NO: 37)
TCATACCATCTCGACAATGCCTCGAACTTGTCCTTCGGCAACGGCTTCGT
CATCGCGTCGGCGATCATGTCGTCGGTGCCAACATGACGAATCCGTAGCT
GCTCGTCCTCCACTAGGTGGCGCACCAAGTGGAACTTGTTCATAATATGC
TTGCTCTTGCTGTGCTTGCCAGGCTTGGCAGTTAGATAGATGCACGACAT
GTTATCGCCGAGTATCTCCGGAGTCGCAAACTCCCAGCATAGTTCGTCAC
AGAGTCCACGTAGCCACTGTAGATCTCTGGTACCTTCATTCATAGCAATA
TACTCTGCTTCCGTTGTGCTCTGTGCGTTGATCTCTTGCTTTCTTGATCC
GTACGAAACCACATTGCCATTGACGAACGTCACAAACCCGCTAACACTCT
TTCGGTCATCAGGGTCATTAGCGTAGTCAGCATCGGTGTAGCACGTCAGA
TTCACGTCGT
```

Without being bound by theory, these cutinase sequences provide the molecular basis for the cross resistance demonstrated above and support the general application of gene sequencing and bioinformatic analysis to select other pest pathogenicity genes with similar outcomes.

Example 16

Intergeneric Resistance in Tobacco was Conferred by the *P. nicotianae* Cutinase Gene-Silencing to a Disease Caused by a *Peronospora tabacina*

Figure 5:
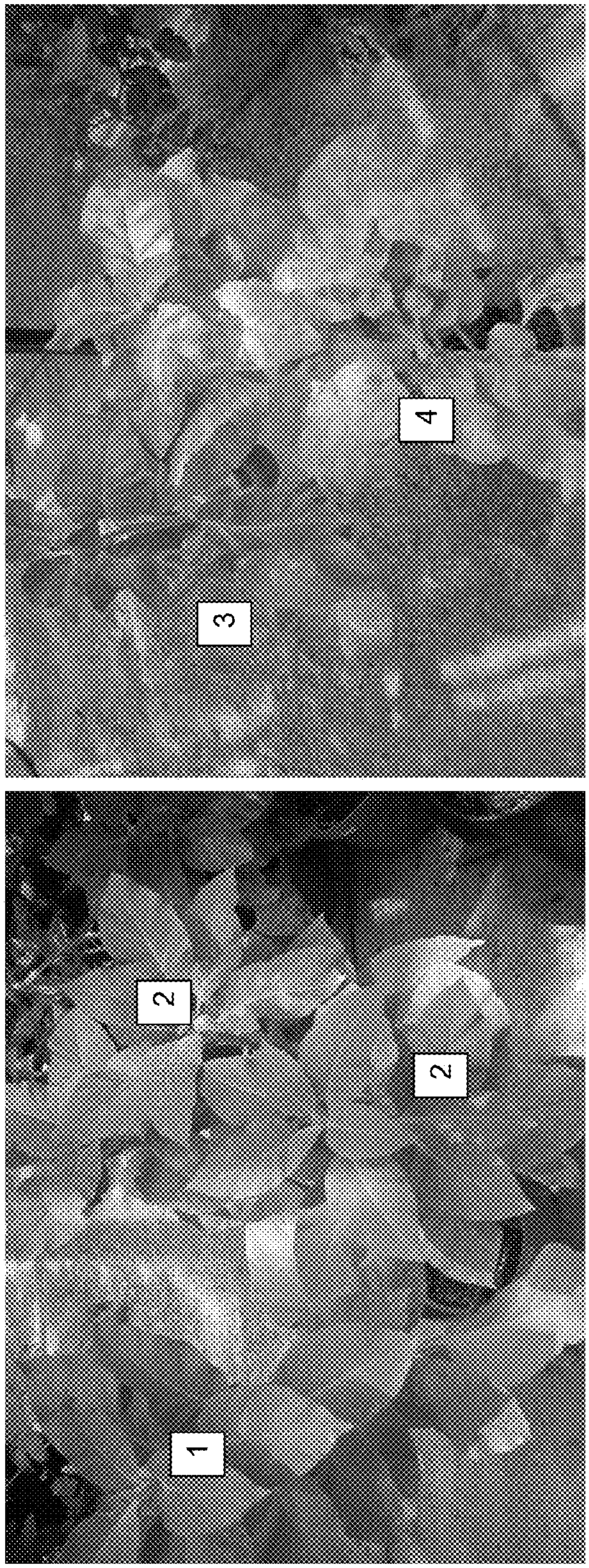
FIG. 5 shows plant reactions to a natural epidemic of the blue mold disease of tobacco caused by *Peronospora tabacina* in the greenhouse.

A natural epidemic of the blue mold disease of tobacco caused by *Peronospora* tabacina occurred in the greenhouse containing the tobacco plants. Clear differences in blue mold severity were observed. Three genotypes of plants were available for evaluation:

Transgenic plants containing the cutinase gene and which had already been selected for resistance to *P. nicotianae*, cutinase transgenic plants which had not yet been selected for resistance to *P. nicotianae*, and wild type or non-transgenic Xanthi tobacco plants. The numbers in the photographs in FIG. 5 refer to the different disease ratings, not the different plant lines or genotypes.

TABLE 10

Reactions of Different Tobacco Genotypes to a Natural Epidemic of Blue Mold of Tobacco Caused by *Peronospora tabacina* in the Greenhouse

| | Disease Rating and Analysis | | | | #Plants | #Plants |
|---|---|---|---|---|---|---|
| Tobacco Genotype | 1 * | 2 | 3 | 4 | 1 + 2 | 3 + 4 |
| *Phytophthora* resistant | 34 ** | 11 | 9 | 12 | 45 (68) *** | 21 (32) |
| Unselected transgenic | 62 | 20 | 67 | 26 | 82 (47) | 93 (53) |
| Wild Type *Xanthi* | 0 | 3 | 12 | 30 | 3 (7) | 42 (93) |

* = Disease ratings.
** = Number of plants in that class.
*** = Percentage of plants in that class.
1 = Symptomless
2 = Obvious symptoms
3 = Severe symptoms
4 = Dead or dying Table 10 shows that among the *P. nicotianae* resistant plants, 68% of them were moderately affected by *Peronospora tabacina* (disease ratings 1+2), and 32% were severely affected (disease ratings 3+4); about a 2:1 ratio in favor of resistance to *Peronospora tabacina*. For the transgenic unselected plants, 47% were moderately affected and 53% severely affected; about a 1:1 ratio in favor of resistance to *Peronospora tabacina*. Of the wild type plants, 7% were moderately affected and 93% were severely affected; about a 13:1 ratio in favor of susceptibility. Therefore, FIG. 5 and Table 10 clearly demonstrate different levels of resistance in the different tobacco genotypes, and that the cutinase gene from *P. nicotianae* induces broad based resistance in tobacco to *Peronospora tabacina*, a fungus distantly related to *P. nicotianae.*

Table 11 demonstrates that *Phytophthora nicotianae* and *Peronospora* tabacina are not closely related taxonomically. Yet, as shown above, the *Phytophthora nicotianae* cutinase gene confers resistance to both *Phytophthora nicotianae* and *Peronospora tabacina*. Therefore, the *Phytophthora nicotianae* cutinase gene provides broad resistance against at least three different fungal species and three fungal diseases. It protects against two different species of *Phytophthora, P. nicotianae* in tobacco and *P. sojae* in soybeans, and it also protects tobacco against both *Phytophthora nicotianae* and *Peronospora* tabacina. These two fungal species are classified in the same order, but in distinctly different families and genera (Table 11).

TABLE 11

Taxonomic relationship between *Phytophthora nicotianae* and *Peronospora tabacina*

| | *Phytophthora nicotianae* | *Peronospora tabacina* |
|---|---|---|
| Class | Oomycetes | Oomycetes |
| Order | Peronosporales | Peronosporales |

TABLE 11-continued

Taxonomic relationship between *Phytophthora nicotianae* and *Peronospora tabacina*

| | *Phytophthora nicotianae* | *Peronospora tabacina* |
|---|---|---|
| Family | Pythiaceae | Peronosporaceae |
| Genus | *Phytophthora* | *Peronospora* |
| Species | *Phytophthora nicotianae* | *Peronospora tabacina* |

Example 17

Figures 6A, 6B, 6C, 6D:
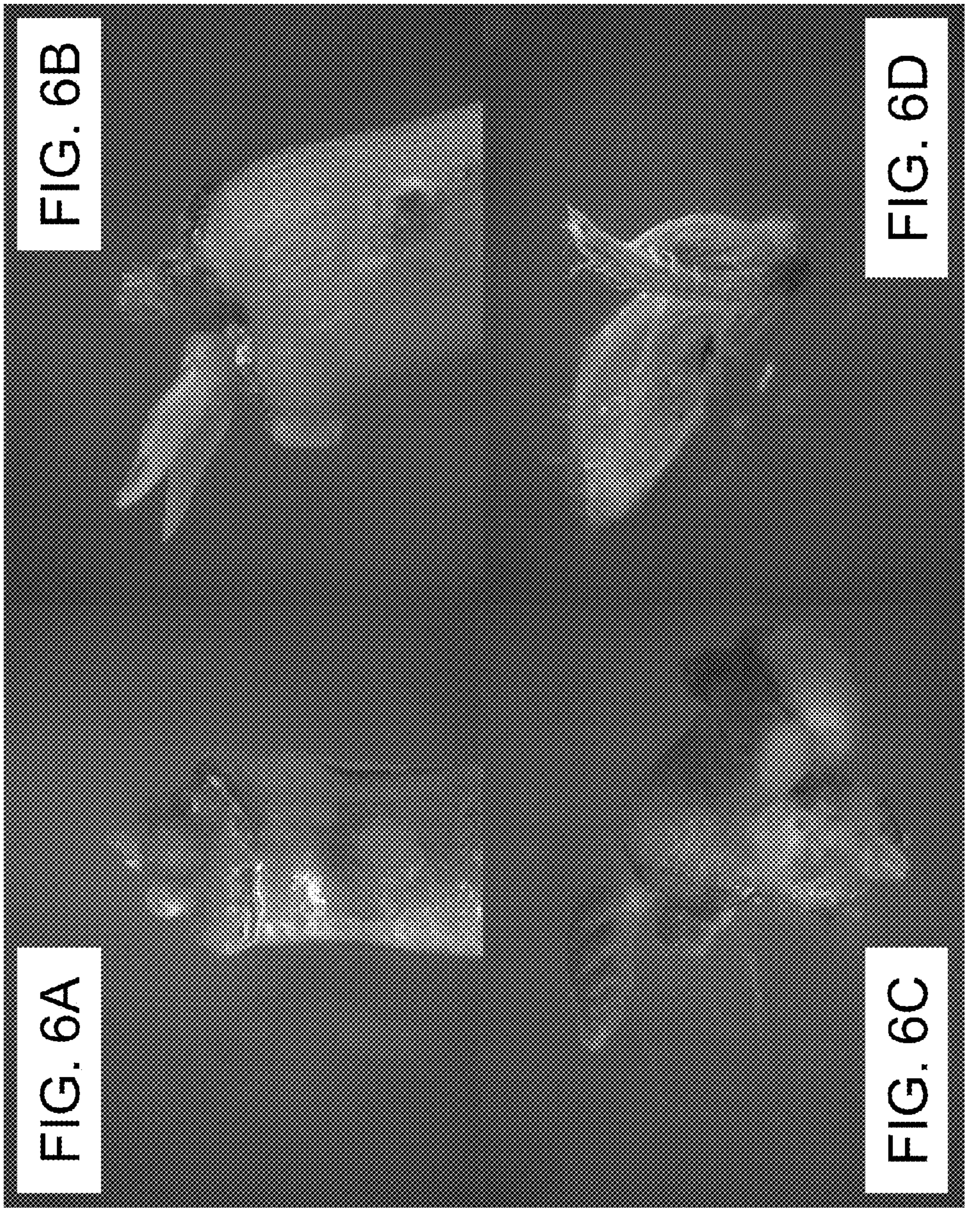
FIG. 6 shows shoots emerging from transgenic soybean embryos.
Figure 7A:
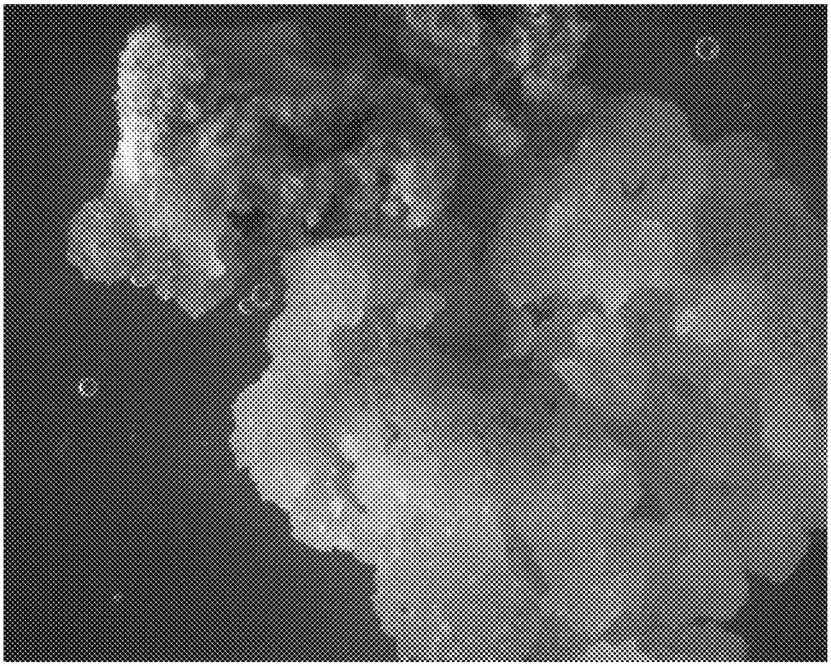
FIG. 7A shows transformed soybean calli.

Soybeans Transformed and Made Resistant with *Phytophthora* Gene Silencing Constructs Soybean tissue culture: Shoots emerged from many of the soybean embryos transformed with pVZA100 (Example 7) by *A. tumefaciens* and by biolistics (FIG. 6). Other calli on the plate remained green and became very friable (FIG. 7A). DNA was extracted from three samples each of the shoots and friable calli, and PCR was performed using the oligonucleotide primers designed to amplify the GUS (SEQ ID NOs: 9 and 10) and hygromycin phosphotransferase (SEQ ID NOs: 11 and 12) genes.

Figure 7B:
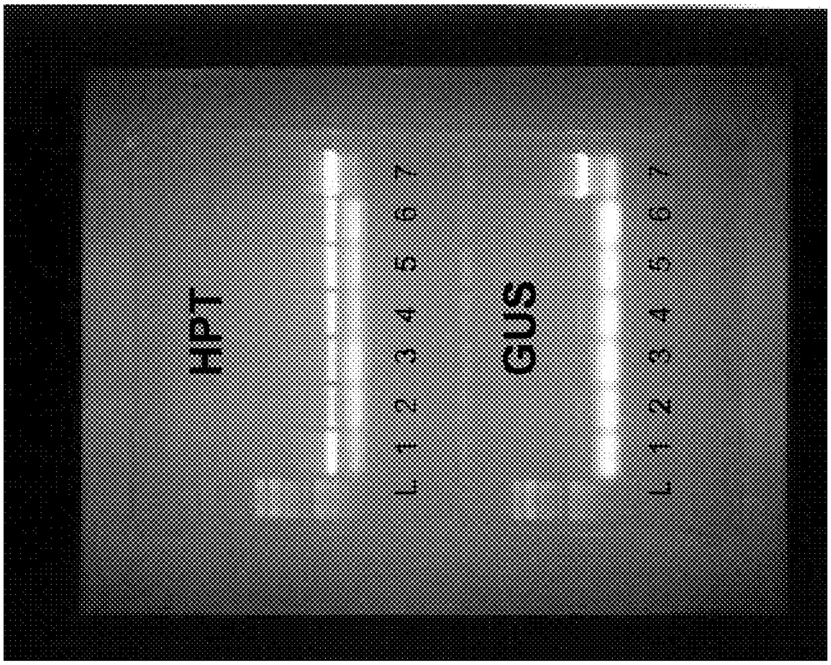
FIG. 7B show GUS and hygromycin phosphotransferase genes detected in the transformed soybean callus.

Both the GUS and hygromycin phosphotransferase genes (HPT) were detected in the soybean callus, as shown in FIG. 7B. The upper panel of FIG. 7B shows that all 6 of the samples (lanes 1-6) were transgenic for HPT (lane 7 is the plasmid control). The lower panel shows that at least 4 (lanes 1, 2, 4, 5) of the 6 samples were transgenic for the GUS gene (lane 7 is the plasmid control). These data demonstrate that the host plant cells were transgenic with the pVZA100 heterologous polynucleotide.

The continued growth of the plantlets and shoots on the medium containing 15 mg/L of hygromycin demonstrate that the calli expressed the heterologous polynucleotide.

The fact that the soybean calli were GUS negative in their staining reaction demonstrated that GUS expression in the host plant cell was silenced by the heterologous polynucleotide.

Next, the calli are grown, rooted, transplanted to soil, and grown to maturity to obtain pollen and seed. Non transformed plants are pollinated with pollen from a mature transformed plant, and the resultant fertilized seed is grown to a mature plant. Mature plants (F0 plants), plants grown from seeds of an F0 plant, and non-transformed plants regenerated from seeds from transformed plant pollen and non-transformed plant flowers all show resistance to *Phytophthora sojae.*

Figure 13:
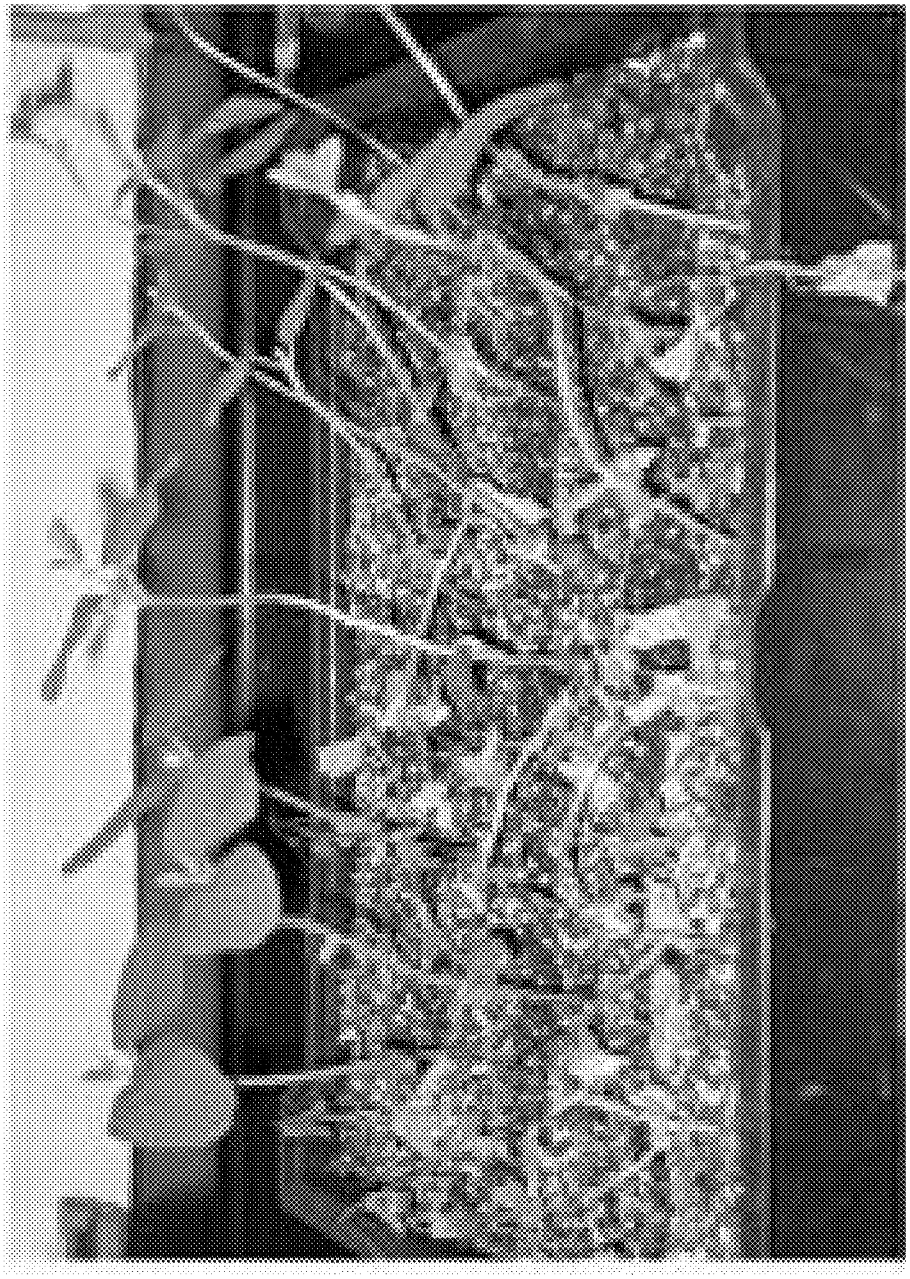
FIG. 13 shows transgenic soybean plants resistant to *Phytophthora sojae.*

Soybean plants: The example above with soybean tissue culture was clearly demonstrated in Example 27 wherein soybean plants transformed by bombardment with pVZA100 were resistant to *P. sojae* (FIG. 13). This result also demonstrates that broad resistance was conferred by the cutinase gene of *P. nicotianae* against *P. sojae.*

Example 18

Potatoes Transformed and Made Resistant to *Phytophthora infestans*

Figure 8:
FIG. 8 shows roots and minitubers produced in the culture plates of potato cells transformed with pVZA100.

From Example 7, both roots and minitubers were produced in the culture plates (FIG. 8). The plantlets, roots, and minitubers grew on the medium containing 15 mg/L of hygromycin demonstrating that the calli were transformed and expressing the hygromycin phosphotransferase transgene. Potato calli transformed with pCAMBIA1201 were GUS positive staining, whereas potato calli transformed with pVZA100 were GUS negative staining This demonstrates that GUS was silenced in those tissues transformed with pVZA100.

PCR analysis demonstrates the presence of the transgenes. Progeny plants from cuttings and tubers test positive for siRNAs.

The potatoes transformed with the silencing construct are resistant to *Phytophthora infestans.*

Potato plants: This example (18) with potato tissue culture was clearly demonstrated in Example 27 wherein potato plants transformed by bombardment with pVZA300 and pVZA400 were resistant to *P. infestans.*

Example 19

Soybeans are Made Resistant to Brown Stem Rot (*Phialophora gregata* rDNA)

Soybean host cells are transformed with a heterologous polynucleotide similar to pVZA100 (Example 3) except that the sense and antisense sequences correspond to *Phialophora gregata* ribosomal RNA gene (rDNA) (GenBank locus U66728, SEQ ID NO: 43). Soybean plants are generated from transformed cells and are successfully selected for conferred resistance to brown stem rot following inoculation with *Phialophora gregata*. Plants resistant to *Phialophora gregata* are also resistant to *Phakopsora pachyrhizi* and *Aspergillus nidulans.*

Example 20

Soybeans are Made Resistant to Brown Stem Rot (*Phialophora gregata* Genotype B DNA Marker)

Soybean host cells are transformed with a heterologous polynucleotide similar to pVZA100 (Example 3) except that the sense and antisense sequences correspond to *Phialophora gregata* ribosomal RNA gene (rDNA) (GenBank locus U66728, SEQ ID NO: 44). Soybean plants are generated from transformed cells and are successfully selected for conferred resistance to brown stem rot following inoculation with *Phialophora gregata*. Plants resistant to *Phialophora gregata* are also resistant to *Phakopsora pachyrhizi* and *Aspergillus nidulans.*

Example 21

Soybeans are Made Resistant to Stem and Root Rot (*Phytophthora sojae* Cutinase)

Soybean host cells are transformed with a heterologous polynucleotide similar to pVZA 100 (Example 3) except that the sense and antisense sequences correspond to *Phytophthora sojae* cutinase (i.e. SEQ ID NO: 36). Soybean plants are generated from transformed cells and are successfully selected for conferred resistance to stem and root rot following inoculation with *Phytophthora sojae.*

Example 22

Soybeans are Made Resistant to White Mold Disease (*Sclerotinia sclerotiorum* RNA Polymerase Subunit)

Soybean host cells are transformed with a heterologous polynucleotide similar to pVZA100 (Example 3) except that the sense and antisense sequences correspond to *Sclerotinia sclerotiorum* partial rpb2 gene for RNA polymerase II second largest subunit, exon 1, strain 484 (GenBank locus AJ745716, SEQ ID NO: 45). Soybean plants are generated from transformed cells and are successfully selected for conferred resistance to white mold disease following inoculation with *Scle-*

*rotinia sclerotiorum*. Plants resistant to *Sclerotinia sclerotiorum* are also resistant to *Phakopsora, Aspergillus nidulans, Magnaporthae orizae, Candida sojae, Gibberella zeae*, and *Puccinia graminis*. Transformed plants show normal growth, lacking a gene with high homology to the *S. sclerotiorum* rpb2 gene. Similar results are obtained using sense and antisense sequences corresponding to *Puccinia hordei* 18S ribosomal RNA gene, partial sequence of GenBank locus AY125412 (SEQ ID NO: 46).

Example 23

Soybeans are Made Resistant to White Mold Disease (*Sclerotinia sclerotiorum* Hexose Transporter)

Soybean host cells are transformed with a heterologous polynucleotide similar to pVZA100 (Example 3) except that the sense and antisense sequences correspond to *Sclerotinia sclerotiorum* hexose transporter (hxt2) gene (GenBank locus AY647268.1, SEQ ID NO: 47). Soybean plants are regenerated from transformed cells and successfully selected for conferred resistance to white mold disease following inoculation with *Sclerotinia sclerotiorum*. Plants resistant to *Sclerotinia sclerotiorum* also demonstrate some resistance to *Botrytis cinerea.*

Example 24

Soybeans are Made Resistant to Sudden Death Syndrome (*Fusarium solani pisi* Cutinase)

Soybean host cells are transformed with a heterologous polynucleotide similar to pVZA100 (Example 3) except that the sense and antisense sequences correspond to *F. solani pisi* cutinase mRNA (GenBank locus K02640.1, SEQ ID NO: 48) Soybean plants are regenerated from transformed cells and successfully selected for conferred resistance to sudden death syndrome following inoculation with *Fusarium solani* glycines. Plants resistant to *Fusarium* solani glycines show some increased resistance to *A. nidulans.*

Example 25

Soybeans are Made Resistant to Asian Rust (*Phakopsora pachyrhizi* Cutinase Homolog)

Soybean host cells are transformed with a heterologous polynucleotide similar to pVZA100 (Example 3) except that the sense and antisense sequences correspond to *Phakopsora pachyrhizi* conserved protein motif of *Phytophthora nicotianae* and found in the *Phakopsora pachyrhizi* genome (GenBank locus AC149367.2, SEQ ID NO: 49). Based on homology with *Phytophthora nicotianae* cutinase, this conserved protein motif is likely a cutinase homologue and involved in penetrance of the soybean cutin. Soybean plants are regenerated from transformed cells and successfully selected for conferred resistance to Asian rust following inoculation with *Phakopsora pachyrhizi.*

Example 26

Soybeans are Made Resistant to Asian Rust (*Phakopsora pachyrhizi* rDNA)

Soybean host cells are transformed with a heterologous polynucleotide similar to pVZA100 (Example 3) except that the sense and antisense sequences correspond to a ribosomal DNA sequence found in the *Phakopsora pachyrhizi* genome (GenBank locus AF333491, SEQ ID NO: 50). Soybean plants are generated from transformed cells and successfully selected for conferred resistance to Asian rust following inoculation with *Phakopsora pachyrhizi.*

Example 27

Testing of Tobacco, Soybean, Potato and Corn for Transgenesis, Resistance to *Phytophthora* Spp. And Resistance to Aphids pVZA100 in Tobacco: Mature tobacco plants produced in Example 5 by transformation with pVZA100 were tested for resistance against *P. nicotianae*. Three methods were tested for inoculation with *P. nicotianae*. All gave satisfactory results, but as explained above, the toothpick method was more rigorous and more dependable. Generally about 20% of the T0 plants transformed with pVZA100 (initial transgenic generation) survived infection with *P. nicotianae*, whereas 0% of the wild type plants and those plants transformed with pCAMBIA 1201 survived.

Surviving plants transformed with pVZA100 were grown to maturity in soil, and seed was collected for subsequent analysis. The seed progeny (=T1 generation) were grown on MS medium containing 30 ug/ml hygromycin, and the surviving plants again tested for resistance to *P. nicotianae.*

Surviving transformed plants also were grown to maturity in soil and seed collected for subsequent analysis. A group of seed progeny (=T2 generation) of four different lines (lines #4, #23, #26 and #27; =different transformation events) of these plants were inoculated twice successively to ensure that any survivors were resistant to *P. nicotianae*. In the first inoculation 192 of 442 plants were resistant (=43%). Upon reinoculation: 150 of 192 plants were resistant (=78%). In summary, 150 of 442 plants were resistant (=34%). All of these 150 resistant plants were also assayed for GUS activity and found to be negative.

Figure 11:
FIG. 11 shows a wild type tobacco plant (A) and a pVZA100 transgenic tobacco plant (B), susceptible and resistant to *Phytophthora nicotianae*, respectively.

Reactions by tobacco plants are shown in FIG. 11. Plant A shows reactions typical of wild type tobacco plants or those transformed with pCAMBIA1201. The plants are susceptible, there are major stem lesions, and the root system is essentially destroyed. Such plants usually die 5-8 days after inoculation. Plant B is from Transgenic line 26 (see below). It is typical of those plants transformed with pVZA100. It was highly resistant to *P. nicotianae* and showed no symptoms other than small lesions on the tips of the upper roots. Such plants grow to maturity and set fertile seed.

pVZA100 in Soybean: Soybean plants were bomarded with pVZA100. PCR with the appropriate primers demonstrated that 15 of 32 bombarded plants were transgenic. Transgenic plants were cultivated to produce seeds and seed plants were tested for resistance to *P. sojae*. As shown in FIG. 13, 43 of 495 seed plants tested were resistant to *P. sojae* (FIG. 13) whereas 100% of a similar number of wild-type and pCAMBIA1201 transformed (i.e. "control-transformed") plants died.

pVZA100 in Potato: Potato plants were bomarded with pVZA100. PCR with the appropriate primers demonstrated that 15 of 18 bombarded plants were transgenic. Transgenic plants are tested for resistance to *P. infestans.* 100% of these plants are resistant as compared to 0% resistance in wild-type or control-transformed plants.

pVZA100 in Corn: Corn plants were bombarded with pVZA100. PCR with the appropriate primers demonstrated that 33 of 44 bombarded plants were transgenic. Transgenic plants are cultivated to produce seeds and seed plant are tested for resistance to *Pythium* graminicola. 25% of the F1 plants tested are resistant as compared to 0% resistance in wild-type or control-transformed plants.

The above results demonstrate that plants useful in the present invention include monocots and dicots. Similarly, corn plants are transformed with pVZA100 and tested and illustrate cross resistance to *Phytophthora* and *Peronospora*.

pVZA200 in Potato: Potato plants were bomarded with pVZA200 (*Myzus persicae* Cathepsin B). PCR with the appropriate primers demonstrated that 7 of 12 bombarded plants were transgenic. Transgenic plants are tested for resistance to aphids (*Myzus persicae*). 80% of such plants, compared to 0% of control or wildtype plants, are resistant.

Aphids after feeding on transformed plants are examined. It is determined that silencing cathespin B in aphids according to the present invention not only protects the plant (i.e. causes aphid resistance in plants) but also reduces the aphid population.

According to the present invention and this example, insect resistance is conferred to plants through transformation with a silencing construct containing an insect gene such as Cathepsin B.

pVZA300 in Potato: Potato plants were bomarded with pVZA300, a construct containing sense and antisense sequence homologous and complementary to Cathepsin B from *Myzus persicae* and elicitin INF1 of *Phytophthora infestans*. PCR with the appropriate primers demonstrated that 15 of 18 bombarded plants were transgenic. Such transgenic plants are tested for resistance to aphids (*Myzus persicae*) and to *Phytophthora infestans*.

In one set of experiments, one group of transformed potato plants are challenged with aphids only and one group is challenged with *Phytophthora infestans* only.

For the aphid challenged plants, 80% of such plants tested are resistant as compared to 0% resistance in wild-type or control-transformed plants.

For the *Phytophthora infestans* challenged plants, 75% of such plants tested were resistant as compared to 0% resistance in non-transformed or control plants.

In another set of experiments, similarly transformed and non-transformed potato plants are challenged with aphids and *Phytophthora infestans* at the same time. 60% of the transgenic plants tested are resistant to both pests as compared to 0% resistance in wild-type or control-transformed plants.

After feeding on transformed plants, *Phytophthora infestans* is isolated and cultured. Such cultures either grow very slowly or die. Microscopic examination reveals that the hyphae are severely malformed.

Moreover, silencing rRNA according to the present invention further illustrates an embodiment whereby the pathogen population in the soil is dramatically reduced.

pVZA300 in Soybeans: Soybean plants were bomarded with pVZA300 (a construct containing sense and antisense sequence homologous and complementary to Cathepsin B from *Myzus persicae* and elicitin INF1 of *Phytophthora infestans*). PCR with the appropriate primers demonstrated that 60% of bombarded plants are transgenic. Transgenic plants are cultivated to produce seeds and seed plants are grown. Such F1 plants are tested for resistance to aphids (*Myzus persicae*) and to *Phytophthora sojae*.

In one set of experiments, one group of transformed soybean plants are challenged with aphids only and one group is challenged with *Myzus persicae* only.

For the aphid challenged plants, 70% of the F1 plants tested are resistant as compared to 0% resistance in wild-type or control-transformed plants.

For the *Phytophthora sojae* challenged plants, 15% of the F1 plants tested are resistant as compared to 0% resistance in wildtype and in control transformed plants.

In another set of experiments, transformed and non-transformed soybeans plants are challenged with aphids and *Phytophthora sojae* at the same time. 10% of the F1 plants tested are resistant to both pests as compared to 0% resistance in wild-type or control-transformed plants.

According to the present invention and these examples, insect resistance and fungus resistance is conferred in a plant (both for moncot and dicot species) by a single heterologous polynucleotide comprising a plurality of genes (i.e. by gene stacking) Moreover, a surprising level of pest resistance is conferred in plants by silencing genes from more than one pest.

After feeding on transformed plants, *Phytophthora sojae* is isolated and cultured. Such cultures either grow very slowly or die. Microscopic examination reveals that the hyphae are severely malformed.

pVZA400 in Soybeans: Soybean plants were bomarded with pVZA400 comprising antisense and sense sequences homologous and complementary to the rRNA gene of *Phytophthora infestans*. PCR with the appropriate primers demonstrated that 12 of 18 bombarded plants were transgenic. Transgenic plants are cultivated to produce seeds and seed plants are tested for resistance to *Phytophthora sojae*. 15% of the F1 plants that are tested are resistant as compared to 0% resistance in non-transformed or control transgenic plants.

After feeding on transformed plants, *Phytophthora sojae* is isolated and cultured. Such cultures either grow very slowly or die. Microscopic examination reveals that the hyphae are severely malformed.

Next, wild-type soybeans are challenged with *Phytophthora sojae* cultures derived from the pVZA400-transformed plants. Such *P. sojae* cultures are non pathogenic in comparison to *sojae* cultures which are derived from wild-type or control-transformed soybeans.

The above results illustrate the usefulness of silencing of rRNA in a pest (e.g. fungi) and further illustrates cross resistance to a pest species other than the pest from which the pest pathogenicity gene was constructed.

After feeding on transformed plants, *Phytophthora sojae* is isolated and cultured. Such cultures either grow very slowly or die. Microscopic examination reveals that the hyphae are severely malformed.

Moreover, silencing rRNA according to the present invention further illustrates an embodiment whereby the pathogen population in the soil is dramatically reduced.

pVZA400 in Potato: Potato plants were bomarded with pVZA400 comprising antisense and sense sequences mologous and complementary to the rRNA gene of *Phytophthora infestans*. PCR with the appropriate primers demonstrated that 6 of 12 bombarded plants were transgenic. Transgenic plants were cultivated and tested for resistance to *Phytophthora infestans*. These plants were tested and showed resistance in 100% of these plants as compared to 0% resistance in wild-type or control-transformed plants.

After feeding on transformed plants, *Phytophthora infestans* is isolated and cultured. Such cultures either grow very slowly or die. Microscopic examination reveals that the hyphae are severely malformed.

The above results the usefulness of a single silencing construct of rRNA in conferring pest resistance in a plurality of plants to a pest (e.g. fungi).

Example 28

Potato is Made Resistant to Tuber Rot (*Fusarium sambucinum* Translation Elongation Factor 1 Alpha)

Potato host cells are transformed with a heterologous polynucleotide similar to pVZA100 (Example 3) except that the sense and antisense sequences correspond to a *Fusarium sambucinum* translation elongation factor 1 alpha DNA sequence (GenBank locus AJ543605, SEQ ID NO: 51). Potato plants are generated from transformed cells and successfully selected for conferred resistance to *Fusarium sambucinum* tuber rot.

Example 29

Tomato is Made Resistant to Late Blight (*Phytophthora infestans* Elicitin Gene)

Tomato host cells are transformed with a heterologous polynucleotide similar to pVZA100 (Example 3) except that the sense and antisense sequences correspond to an elicitin gene sequence found in the *Phytophthora infestans* genome (GenBank locus AY766228, SEQ ID NO: 52). Tomato plants are generated from transformed cells and successfully selected for conferred resistance to late blight of tomato following inoculation with *Phytophthora infestans*.

Example 30

Canola is Made Resistant to Stem Rot (*Sclerotinia sclerotiorum* RNA Polymerase Subunit)

Canola host cells are transformed with a heterologous polynucleotide similar to pVZA100 (Example 3) except that the sense and antisense sequences correspond to a *Sclerotinia sclerotiorum* partial rpb2 gene for RNA polymerase II second largest subunit, exon 1, strain 484 1096 bp (GenBank locus AJ745716, SEQ ID NO: 53). Canola plants are generated from transformed cells and successfully selected for conferred resistance to stem rot following inoculation with *Sclerotinia sclerotiorum*.

Example 31

Cotton is Made Resistant to Cotton Wilt (*Fusarium solani pisi* Cutinase Homolog)

Cotton host cells are transformed with a heterologous polynucleotide similar to pVZA100 (Example 3) except that the sense and antisense sequences correspond to a cutinase gene from *F. solani pisi* (GenBank locus K02640.1, SEQ ID NO: 48). This sequence is picked herein because of the homology of genes within the genus *Fusarium*. Cotton plants are generated from transformed cells and successfully selected for conferred resistance to cotton wilt following inoculation with *Fusarium oxysporum*.

Example 32

Corn is Made Resistant to Mycotoxins (*F. solani pisi* Cutinase)

Corn host cells are transformed with a heterologous polynucleotide similar to pVZA100 (Example 3) except that the sense and antisense sequences correspond to a cutinase gene from an *F. solani pisi* (GenBank locus K02640.1, SEQ ID NO: 48). This sequence is picked herein because of the homology of genes within the genus *Fusarium*. Corn plants are generated from transformed cells and selected for increased resistance to mycotoxins following inoculation with *Fusarium moniliforme*.

Example 33

Corn is Made Resistant to Stalk Rot (*Stenocarpella maydis* rDNA)

Corn host cells are transformed with a heterologous polynucleotide similar to pVZA100 (Example 3) except that the sense and antisense sequences correspond to *Stenocarpella maydis* rRNA (GenBank locus AY332489, SEQ ID NO: 54). This sequence is picked herein because of the homology of genes within the genera *Stenocarpella* and *Fusarium*. Corn plants are generated from transformed cells and selected for increased resistance to stalk rot following inoculation with *Stenocarpella maydis* and several *Fusarium* spp Example 34

Corn is Made Resistant to Leaf Blight (*Cercospora zeae-maydis* 18s rDNA)

Corn host cells are transformed with a heterologous polynucleotide similar to pVZA100 (Example 3) except that the sense and antisense sequences correspond to 18S ribosomal RNA from a *Cercospora zeae-maydis* Group II (GenBank locus AF291710, SEQ ID NO: 55). Corn plants are generated from transformed cells and successfully selected for conferred resistance to leaf blight following inoculation with *Cercospora zeae-maydis*.

Example 35

Potato is Made Resistant to Green Peach Aphid (*Myzus persicae* Cathepsin B Protease)

Potato host cells are transformed with a heterologous polynucleotide similar to pVZA100 (Example 3) except that the sense and antisense sequences correspond to Cathepsin B protease from *Myzus persicae* (GenBank locus AY702822, SEQ ID NO: 56). Potato plants are generated from transformed cells and successfully selected for conferred resistance to green peach aphids following inoculation with *Myzus persicae*.

Example 36

Potato is Made Resistant to Colorado Potato Beetle (*Leptinotarsa decemlineata* Cysteine Protease)

Potato host cells are transformed with a heterologous polynucleotide similar to pVZA100 (Example 3) except that the sense and antisense sequences correspond to cysteine protease from *Leptinotarsa decemlineata* (GenBank locus AY159377, SEQ ID NO: 57). Potato plants are generated from transformed cells and successfully selected for conferred resistance to Colorado potato beetle following inoculation with *Leptinotarsa decemlineata*. Such regenerated potatoes demonstrate increased resistance to each of the following: *Callosobruchus maculates, Diabrotica virgifera virgifera, Acanthoscelides obtectus, Helicoverpa armigera, Leptinotarsa decemlineata, Anthonomus grandis, Triatoma infestans, Tenebrio molitor, Toxoptera citricida, Aphis gossypii, Pandalus borealis, Myzus persicae, Delia radicum, Sarcophaga peregrine, Sitophilus zeamais, Boophilus microplus, Hypera postica, Frankliniella occidentalis*, and *H. americanus*.

Example 37

Potato is Made Resistant to *Verticillium* Wilt (*V. dahliae* rDNA)

Potato host cells are transformed with a heterologous polynucleotide similar to pVZA100 (Example 3) except that the sense and antisense sequences correspond to *Verticillium dahliae* rDNA (GenBank locus AF108478, SEQ ID NO: 58). Potato plants are generated from transformed cells and successfully selected for conferred resistance to *Verticillium* wilt following inoculation with *Verticillium dahliae.*

Example 38

Soybeans are Made Resistant to Downy Mildew (*Peronospora berteroae* rDNA)

Soybean host cells are transformed with a heterologous polynucleotide similar to pVZA100 (Example 3) except that the sense and antisense sequences correspond to internal transcribed spacer 1 partial sequence of 5.8S ribosomal RNA found in the *Peronospora* berteroae genome (GenBank locus AY531450, SEQ ID NO: 59). Soybean plants are generated from transformed cells and successfully selected for conferred resistance to downy mildew following inoculation with *Peronospora manchurica*. Such selected soybeans also have increased resistance to *Hyaloperonospora species* (e.g. *H. camelinae, H. niessleana, H. parasitica*, and *H. thlaspeos-perfoliati*) and *Peronospora* species (e.g. *P. arabidopsidis, P. arabis-alpinae, P. buniadis, P. cardaminopsidis, P. cochleariae, P. dentariae, P. galligena, P. hesperidis, P. iberidis, P. isatidis, P. nesleae, P. sisymbrii-loeselii, P. sisymbrii-officinalis, P. sisymbrii-sophiae, P. thlaspeos-alpestris*, and *P. thlaspeos-arvensis*).

Example 39

Potato is Made Resistant to Potato Root Knot Nematode (*Meloidogyne chitwoodi* Cytochrome Oxidase II)

Potato host cells are transformed with a heterologous polynucleotide similar to pVZA100 (Example 3) except that the sense and antisense sequences correspond to a sequence found in the *Meloidogyne chitwoodi* genome (i.e. cytochrome oxidase subunit II gene, (GenBank locus AY757882, SEQ ID NO: 60). Potato plants are generated from transformed cells and successfully selected for conferred resistance to potato root knot following inoculation with *Meloidogyne chitwoodi*. Such selected potato plants are also found to be resistant to *Bombyx mandarina, Bombyx mori, Chilo tumidicostalis, Hemileuca, Hydrotaea aenescens, Meloidogyne hapla, Meloidogyne partityla, Oecetis avara, Papilio aegeus, Papilio demoleus, Papilio erithonioides, Papilio hipponous, Papilio oribazus, Papilio protenor, Papilio troilus, Papilio xuthus, Sabethes cyaneus*, and *Samia cynthia ricini.*

Example 40

Soybeans are Made Resistant to Nematode Infestation (*Pratylenchus scribneri* and *Heterodera glycines* Ribosomal RNA Genes)

The present invention can be used to produce host plants with increased resistance to additional nematodes. Nematode polynucleotide sequences that are known and are searchable in public databases such as the NCBI/NIH GenBank demonstrate conserved nucleotide motifs among different nematode genera. Conserved nucleotide motifs strongly suggest that these sequences are associated with viability and/or parasitism and are functionally conserved and expressed in both *Meloidogyne incognita* (root-knot nematode) and *Globodera rostochiensis* and *Globdera pallids* (potato cyst nematodes), and also in the well studied *Heterodera glycines* and *Caenorhabditis elegans*. Thus, the use of these sequences and variants thereof, is advantageous because such RNAi can be designed to have broad RNAi specificity and are thus useful for controlling a large number of plant parasitic nematodes in planta. Because genes identified herein are associated with nematode survival and/or parasitism, RNAi inhibition of these genes (arising from contacting nematodes with compositions comprising RNAi molecules such as, for example, by allowing nematodes to feed on plants transformed as taught herein) prevents and/or reduces parasitic nematode growth, development, and/or parasitism.

Nematode feeding is a useful indicator of the effectiveness of the methods of the present invention. The *Pratylenchus scribneri* in vitro feeding assay uses a corn root exudate as a feeding stimulus and both the red dye Amaranth, or potassium arsenate, as feeding indicators. Feeding is confirmed after seven days by the presence of red stained intestinal cells in live worms exposed to the Amaranth or death of worms exposed to arsenate. *P. scribneri* can be cultured on wild type roots of corn, rice and *Arabidopsis*, and on *Agrobacterium rhizogenes*-induced hairy roots of sugar beet and tomato. *P. scribneri* is very valuable in evaluating transgenic hairy roots (ideally developed by use of *Agrobacterium rhizogenes* strains known in the art as transformation vectors) because of the non-specific feeding of these worms.

Corn, rice, tomato, and sugar beets are transformed with a heterologous polynucleotide containing complementary sense and antisense sequences of *P. scribneri* ribosomal RNA (GenBank locus SEQ ID NO:61). *P. scribneri* is tested on a feeding assay using transformed and wild type corn, rice, tomato, and sugar beets. Transformed plants demonstrate increased resistance to *P. scribneri.*

Soybeans are transformed with a heterologous polynucleotide containing complementary sense and antisense sequences of *Heterodera glycines* ribosomal RNA (GenBank locus AY667456, SEQ ID NO: 62). *Heterodera glycines* is tested on a feeding assay using transformed and wild type soybeans. Transformed soybeans demonstrate increased resistance to *Heterodera glycines.*

Example 41

Various Plants are Made Resistant to Infection by Various *Phytophthora* Spp. (*Phytophthora nicotianae* cutinase)

In one embodiment, the pVZA100 heterologous polynucleotide (Example 3) is used to transform a variety of plants to confer resistance to various *Phytophthora* species. For example, resistance is conferred against *Phytophthora* spp.-induced leaf and stem infections when any of *Chrysalidocarpus* palm, *Catharanthus, Dendrobium*, poinsettia, impatiens, sage, spathiphyllum, or onion is transformed with the pVZA100 (SEQ ID NO: 5). Resistance is conferred against *Phytophthora* spp.-induced root rot when any of poinsettia, tomato, pineapple, or anthurium is transformed with the pVZA100.

Resistance is conferred against *Phytophthora* spp.-induced crown and collar rots when any of watermelon, protea, or African violet is transformed with the pVZA100.

Resistance is conferred against *Phytophthora* spp.-induced fruit rots when any of tomato, papaya, or eggplant is transformed with the pVZA100.

Example 42

Agave is Made Resistant to Agave Root Rot (*Fusarium solani pisi* Cutinase)

Agave host cells are transformed with a heterologous polynucleotide similar to pVZA100 (Example 3) except that the sense and antisense sequences correspond to a cutinase gene from *Fusarium* solani pisi (GenBank locus K02640.1, SEQ ID NO: 48) This sequence is picked herein because of the homology of genes within the genus *Fusarium*. Agave plants are generated from transformed cells and successfully selected for conferred resistance to Agave rot following inoculation with *Fusarium oxysporum*

Example 43

Rice is Made Resistant to Blast Disease (*Magnaporthe grisea* RNA Polymerase II)

Rice host cells are transformed with a heterologous polynucleotide similar to pVZA100 (Example 3) except that the sense and antisense sequences correspond to a *Magnaporthe grisea* RNA polymerase II sequence of (GenBank locus XM 362268, SEQ ID NO: 63). Transformation was accomplished by electroporation or *Agrobacterium tumefaciens*. Rice plants are generated from transformed cells and successfully selected for conferred resistance to rice blast disease following inoculation with *Magnaporthe grisea.*

Example 44

Various Plants Are Made Resistant To *Phytophthora*-Induced Root Disease (*Phytophthora citricola* Cutinase)

Various plants cells including those from *Rhododendron* (e.g. *Rh. catawbiense, Rh. simsii*), *Erica* sp., *Calluna* sp., avocado trees, citrus trees, and hops are transformed with the heterologous polynucleotide pVZA100 (Example 3). This construct was chosen because of the homology between *Phytophthora nicotianae* SEQ ID NO: 14 and *Phytophthora citricola* SEQ ID NO: 34. Host plants are generated from transformed cells and successfully selected for conferred resistance to disease following inoculation with *Phytophthora citricola.*

Example 45

Barley is Made Resistant to Barley Leaf Rust (*Puccinia hordei* 18S Ribosomal RNA)

Barley cells are transformed with the heterologous polynucleotide similar to pVZA100 (Example 3) except that the sense and antisense sequences correspond to *Puccinia hordei* 18S rRNA (GenBank locus AY125412, SEQ ID NO:64). Host plants are generated from transformed cells and successfully selected for conferred resistance to barley leaf rust following inoculation with *Puccinia hordei.*

Example 46

Barley is Made Resistant to Downy Mildew (*Pseudoperonospora humuli* rDNA)

Barley cells are transformed with the heterologous polynucleotide similar to pVZA100 (Example 3) except that the sense and antisense sequences correspond to sequences from *Pseudoperonospora humuli* isolate HV 148 internal transcribed spacer 1, partial sequence; 5.8S ribosomal RNA (GenBank locus AY198305, SEQ ID NO: 65). Host plants are generated from transformed cells and successfully selected for conferred resistance to downy mildew following inoculation with *Pseudoperonospora humuli.*

Example 47

Barley is Made Resistant to Gray Mold Disease (*Botrytis cinerea* Cytochrome P450 Monoxygenase)

Barley cells are transformed with the heterologous polynucleotide similar to pVZA100 (Example 3) except that the sense and antisense sequences correspond to sequences from *Botrytis cinerea* for aba2 gene for cytochrome P450 monoxygenase, exons 1-5 (GenBank locus AJ851088, SEQ ID NO: 66). Host plants are generated from transformed cells and successfully selected for conferred resistance to gray mold disease following inoculation with *Botrytis cinerea.*

Example 48

Tomato is Made Resistant to Tomato Speck Disease (*Pseudomonas syringae* rDNA)

Tomato cells are transformed with the heterologous polynucleotide similar to pVZA100 (Example 3) except that the sense and antisense sequences correspond to *Pseudomonas syringae* ribosomal RNA (GenBank locus AY342210, SEQ ID NO: 67). Host plants are generated from transformed cells and are successfully selected for conferred resistance to tomato speck disease following inoculation with *Pseudomonas syringae.*

Example 49

Tomato is Made Resistant to Bacterial Wilt (*Clavibacter michiganensis michiganensis* Cel A Gene)

Tomato cells are transformed with the heterologous polynucleotide similar to pVZA100 (Example 3) except that the sense and antisense sequences correspond to *Clavibacter michiganensis michiganensis* Cel A gene (GenBank locus AY007311, SEQ ID NO: 68). Host plants are generated from transformed cells and are successfully selected for conferred resistance to bacterial wilt following inoculation with *Clavibacter michiganensis michiganensis.*

Example 50

Corn is Made Resistant to Goss's Bacterial Wilt and Blight (*Clavibacter michiganensis* Endo β-Glucosidase Gene)

Corn cells are transformed with the heterologous polynucleotide similar to pVZA100 (Example 3) except that the sense and antisense sequences correspond to *Clavibacter michiganensis* gene for endo β-glucosidase (GenBank locus X62582, SEQ ID NO: 69). Host plants are generated from transformed cells and are successfully selected for conferred resistance to Goss's bacterial wilt and blight (leaf freckles and wilt) following inoculation with *Clavibacter michiganensis.*

Example 51

Figure 10:
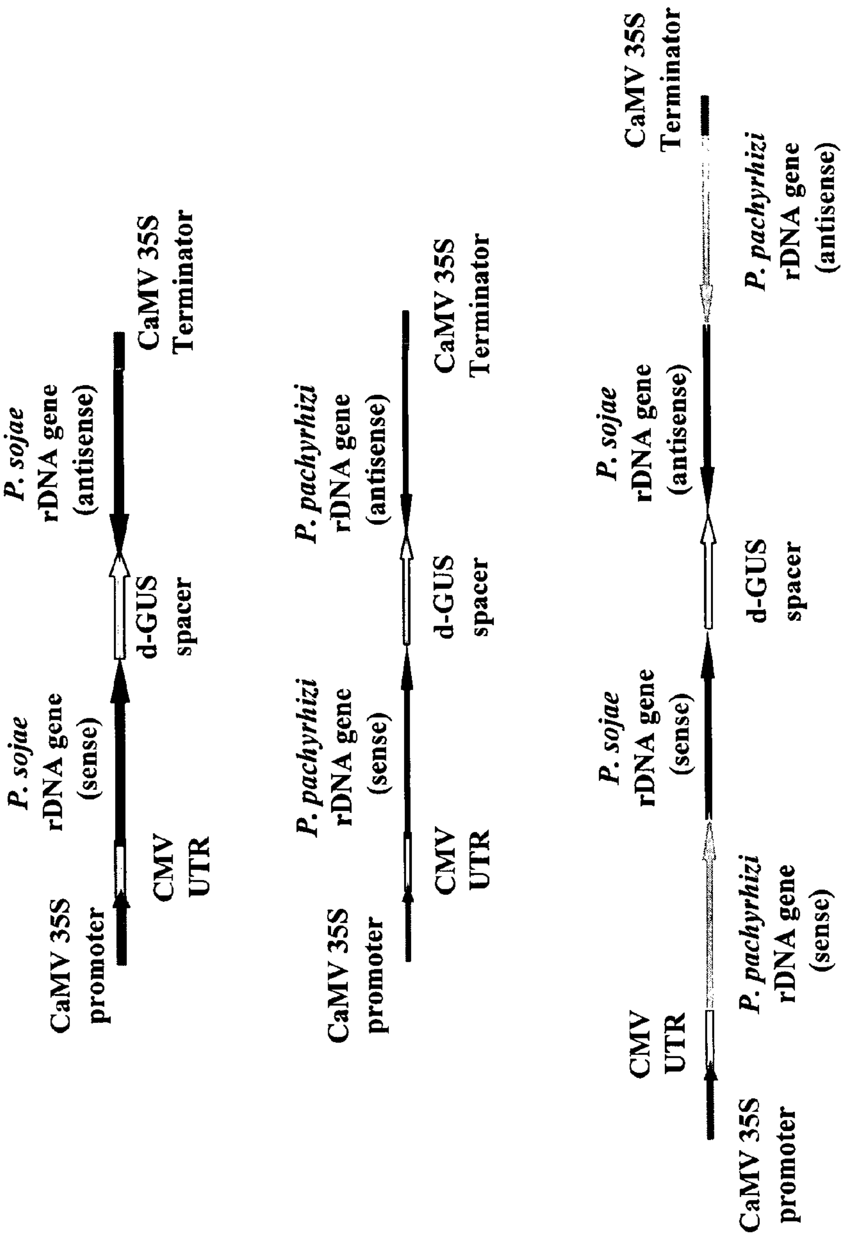
FIG. 10 shows gene silencing constructs based on rDNA and capable of silencing these essential genes in *Phytophthora*, in *Phakopsora* and in both species.

A Silencing Construct Method to Protect Soybeans Against One or Two Fungal Diseases A soybean host plant cell is transformed with either of the gene silencing constructs of FIG. 10 and mature plants are generated therefrom. Mature plants are screened for resistance to two major fungal diseases, namely soybean root and stem rot caused by *Phytophthora sojae* and Asian rust of soybean caused by *Phakopsora pachyrhizi*. Plants are identified that are resistant to each and to both of these two diseases. Those plants transformed with the upper construct are resistant to soybean root and stem rot. Those plants transformed with the middle construct are resistant to Asian rust of soybean. Those plants transformed with the lower construct are resistant to both soybean root and stem rot and Asian rust of soybean.

Example 52

Figure 9:
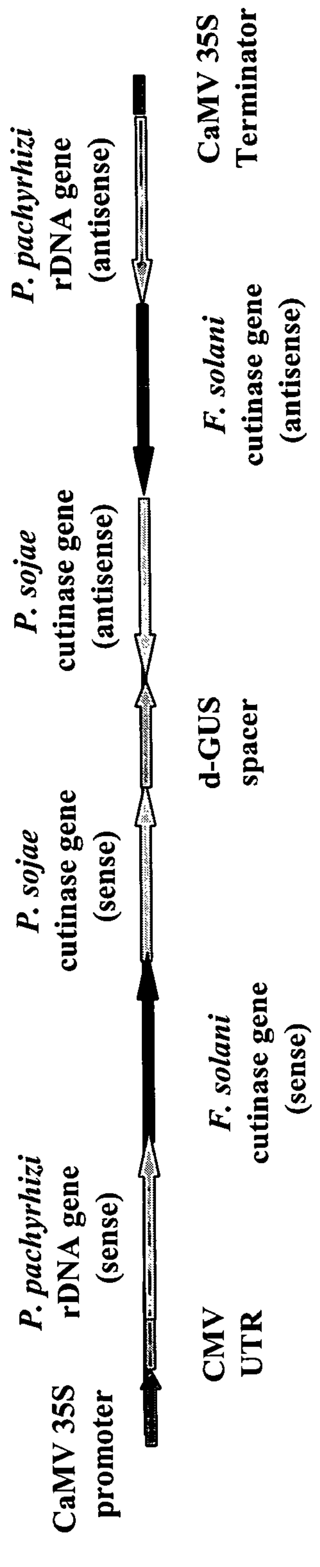
FIG. 9 shows a polycistronic gene silencing construct capable of silencing essential genes in three fungal species causing serious diseases of soybeans.

A Polycistronic Silencing Construct Method to Protect Soybeans Against Three Fungal Diseases A soybean host plant cell is transformed with a polycistronic gene silencing construct of FIG. 9 and mature plants are generated therefrom. Mature plants are screened for resistance to three major fungal diseases, namely soybean root and stem rot caused by *Phytophthora sojae*, soybean sudden death syndrome caused by *Fusarium solani* f sp. *glycines*, and Asian rust of soybean caused by *Phakopsora pachyrhizi*. Plants are identified that are resistant to each and all of these three diseases.

Example 53

Depathogenesis of *Phytophthora* Species by Feeding on Transgenic Plants or by Direct Transformation with pVZA 100, pVZA300 or pVZA400

Tobacco host cells were transformed with the silencing construct pVZA 100 (SEQ ID NO: 5) and plants were generated therefrom. Such transformed plants were highly resistant to *P. nicotianae*. Typical reactions by tobacco plants are shown in FIG. 11. Plant A shows reactions typical of wild type tobacco plants or those transformed with pCAMBIA1201. The plants are susceptible, there are major stem lesions, and the root system is essentially destroyed. Such plants usually die 5-8 days after inoculation. Plant B is from Transgenic line 26 (see below). It is typical of those plants transformed with pVZA100. It is highly resistant to *P. nicotianae* and shows no symptoms other than small lesions on the tips of the upper roots. Such plants grow to maturity and set fertile seed.

Figure 12:
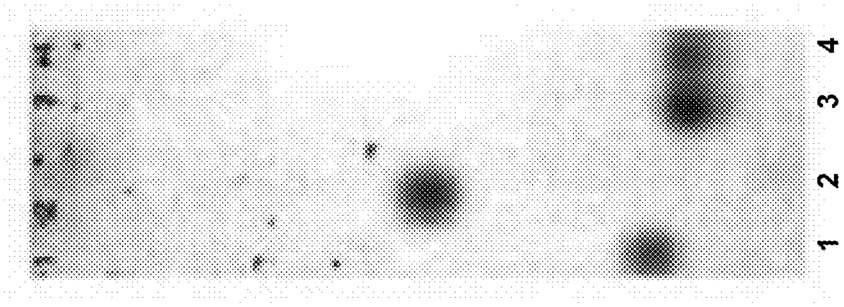
FIG. 12 is an autoradiogram showing the siRNAs isolated from a transgenic tobacco plant (3) and from *Phytophthora nicotianae* growing on a silenced transgenic tobacco plant (4).

When *P. nicotianae* was re-isolated from the restricted lesions on the resistant plant and re-tested on wild type plants, it was no longer pathogenic. Isolation of RNA from this fungus and hybridization with the radioactive cutinase probe as above in Example 14 indicates the presence of siRNAs for the cutinase gene in *P. nicotianae*, thereby explaining the loss of pathogenicity. In FIG. 12, lane 1 again shows the 35 nt oligonucleotides VZA 3F (SEQ ID NO: 3) and VZA 4R (SEQ ID NO: 4) serving as the molecular size control, lane 2 shows the 620 nt messenger RNA from the wild type fungus, lane 3 shows the siRNAs from a silenced transgenic tobacco plant, and lane 4 shows the siRNAs from the nonpathogenic fungus isolated from the resistant transgenic tobacco.

As shown in Example 13, transforming species of a pest directly with silencing constructs or by feeding pest species on plants transformed with silencing constructs had major effects on the pathogenicity, growth and survival of the pest (in this example, the fungi). These results support directly or indirectly the utility of this embodiment of the present invention to minimize crop losses to pests and to enhance agricultural productivity.

Example 54

Depathogenesis: Watermelon Transformed with a Cutinase Silencing Heterologous Polynucleotide (*F. oxysporum* Cutinase)

In Florida and Georgia watermelons can be planted in a field for only one year. The farmer must then wait 6 or 7 years to use that field again because a single year of use results in the high build up of pathogenic isolates of *Fusarium oxysporum*. To use a field in successive years, the farmer must resort to expensive and severe annual treatments with methyl bromide or other potent chemicals.

Watermelons are regenerated from a host plant cell transformed with a heterologous polynucleotide similar to pVZA 100 (Example 3) except that the sense and antisense sequences correspond to the cutinase gene in *F. oxysporum. F. oxysporum* infects the watermelon and the *F. oxysporum* cutinase gene is silenced. Other watermelon species (not transformed according to the present invention) are planted within six feet of the regenerated (transgenic) watermelon. Such other watermelon species are infected by *F. oxysporum* to a lesser extent than would be predicted were it not for the cultivation of the regenerated (transgenic) watermelons adjacent to them.

Example 55

Broad Based Plant Resistance and Depathogenesis with Ribosomal RNA Silencing Heterologous Polynucleotides Optionally, to effectively implement depathogenesis, a broad-based or cross generic protection against several species of pathogenic fungi can be obtained. This can be accomplished by utilizing silencing constructs containing ribosomal DNA (rDNA) genes. The rDNA sequences of fungal pathogens are similar enough to function in the control of closely related fungal species, but are sufficiently dissimilar to permit differentiation among groups of fungi, thereby enabling the selective targeting of specific groups of fungal pathogens with single or multiple or polycistronic gene silencing constructs.

This approach is illustrated in Table 12. The 18S rDNA sequences of *Phytophthora sojae* and *Phakopsora pachyrhizi* were “blasted” against the data in the NCBI/NIH GenBank. The *Phytophthora sojae* sequence showed strong homology (100 to 93%) to the sequences of 16 additional closely related fungal species, but it did not show significant homology to that of *Phakopsora pachyrhizi*. Conversely, the 18S rDNA sequence of *Phakopsora pachyrhizi* showed strong homology (100 to 93%) to the sequences of 19 additional closely related fungal species, but it did not show significant homology to that of *Phytophthora sojae*. Therefore, individual gene silencing constructs can be developed in accord with the teachings herein to control the group of fungi related to *Phytophthora sojae* or to *Phakopsora pachyrhizi*, or alternatively a polycistronic gene silencing construct can be developed to control both groups simultaneously.

TABLE 12

| GenBank sequences ribosomal DNA producing significant alignments with target species | | | |
|---|---|---|---|
| *Phytophthora sojae* 18s ribosomal DNA The identities of the sequences ranges from 100 to 93% over 129 nucleotides. | | *Phakopsora pachyrhizi* 18s ribosomal DNA The identities of the sequences ranges from 100 to 93% over 89 nucleotides. | |
| Fungus Species = (17) | (bits) | Fungus Species = (18) | (bits) |
| *Phytophthora sojae* | 278 | *Phakopsora pachyrhizi* | 278 |
| *Phytophthora vignae* | 194 | *Phakopsora meibomiae* | 153 |
| *Phytophthora drechsleri* | 174 | *Uromyces aemulus* | 131 |
| *Phytophthora cinnamomi* | 174 | *Puccinia striiformis* | 123 |
| *Plasmopara viticola* | 168 | *Pandora neoaphidis* | 121 |
| *Phytophthora melonis* | 167 | *Puccinia allii* | 119 |
| *Phytophthora cryptogea* | 165 | *Piromyces* sp. | 119 |
| *Phytophthora pistaciae* | 161 | *Dioszegia* sp. | 117 |
| *Hyaloperonospora parasitica* | 161 | *Bullera* sp. *T* | 117 |
| *Phytophthora niederhauserii* | 161 | *Dioszegia crocea* | 117 |
| *Phytophthora sinensis* | 153 | *Cadophora* sp. | 117 |
| *Phytophthora cajani* | 153 | *Dioszegia hungarica* | 117 |
| *Pythium insidiosum* | 153 | *Phialophora* sp. | 117 |
| *Phytophthora palmivora* | 151 | *Anaeromyces* sp. | 117 |
| *Phytophthora ramorum* | 149 | *Phialophora melinii* | 117 |
| *Peronospora corydalis* | 149 | *Puccinia triticina* | 115 |
| *Pythium rostratum* | 141 | *Neocudoniella radicella* | 115 |
| | | *Pinctada nigra* | 115 |
| | | *Peziza vesiculosa* | 115 |
| | | *Phillipsia domingensis* | 115 |

Example 56

Control of Multiple Plant Pests Using Multiple Silencing Heterologous Polynucleotides Plants are often attacked by a multiplicity of pests. Optionally, it may be useful to control several pests on the same plant. Methods for gene stacking to control multiple pests and the useful gene sequences (for example, genes encoding ribosomal RNAs, cutinases, cathepsins and other essential enzymes and proteins) are taught herein. A nonlimiting example is soybeans and the simultaneous control of *Phytophthora* root and stem rot, Asian rust, the soybean cyst nematode, sudden death syndrome and aphids. Exemplary genes to stacked for this purpose include SEQ ID NO: 14 for *Phytophthora* root and stem rot, SEQ ID NO: 50 for Asian rust, SEQ ID NO: 62 for the soybean cyst nematode, SEQ ID NO: 48 for sudden death syndrome, and SEQ ID NO: 56 for aphids.

Similarly, corn can be made resistant to root and stalk rots, mycotoxins, leaf blights, stalk and ear borers, aphids and nematodes. Similarly, cotton can be made resistant to boll rot, *Verticillium* and *Fusarium* wilts, seedling blights, damping off, boll weevil, bollworms, aphids, and loopers. Similarly, canola can be made resistant to black leg, stem rot, black spot, damping off and seedling blights, flea beetles, weevils, and aphids.

Similarly, wheat can be made resistant to leaf and stem rust, head blight, *Septoria* blotches, take-all, smuts, powdery and downy mildew, aphids and nematodes. Similarly, tomato can be made resistant to late blight, anthracnose, gray mold, *Verticillium* wilt, nematodes, and aphids. Similarly, potato can be made resistant to late blight, early blight, *Verticillium* wilt, nematodes, Colorado potato beetle, and aphids.

All references cited herein are incorporated by reference herein for all that they teach and for all purposes, to the extent they are not inconsistent with the explicit teachings herein. It is to be understood that, while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The Sequence Listings are incorporated herein by reference.

I claim:

1. A method of conferring fungal resistance to a plant comprising expressing in the plant:

(a) an antisense sequence having at least 80% homology to at least one *Phytophthora* cutinase gene;

(b) a sense sequence substantially complementary to the antisense sequence, wherein a transcript of the antisense sequence and a transcript of the sense sequence are capable of hybridizing to form a double-stranded region; and whereby the plant is resistant to a fungus expressing at least one gene having substantial homology to the antisense sequence.

2. The method of claim 1, wherein the antisense sequence has at least 80% homology to at least one additional *Phytophthora* cutinase gene and, whereby the plant is resistant to a fungus expressing at least one gene having substantial homology to the at least one additional *Phytophthora* cutinase gene.

3. The method of claim 1, wherein the transcript of the antisense sequence and the transcript of the sense sequence form a double stranded region.

4. The method of claim 2, wherein the transcript of the antisense sequence and the transcript of the sense sequence form a double stranded region.

5. The method of claim 1, further comprising expressing in the plant:

(c) a second antisense sequence having at least 80% homology to a second *Phytophthora* cutinase gene; and (d) a second sense sequence substantially complementary to the second antisense sequence;

wherein a transcript of the second antisense sequence and a transcript of the second sense sequence are capable of hybridizing to form a double-stranded region; and whereby the plant is resistant to a fungus expressing at least gene having substantial homology to the second antisense *Phytophthora* cutinase gene.

6. The method of claim 5, wherein the transcript of the second antisense sequence and the transcript of the second sense sequence form a double stranded region.

7. The method of claim 1, wherein the *Phytophthora* cutinase gene is selected from the group consisting of SEQ ID NOs:13, 15, 21, 30 and 32-37.

8. The method of claim 5, wherein the *Phytophthora* cutinase gene and the second *Phytophthora* cutinase gene are selected from the group consisting of SEQ ID NOs:13, 15, 21, 30 and 32-37.

9. A transgenic plant that is resistant to fungus, the transgenic plant comprising:

(a) an antisense sequence having at least 80% homology to at least one *Phytophthora* cutinase gene;

(b) a sense sequence substantially complementary to the antisense sequence, wherein a transcript of the antisense sequence and a transcript of the sense sequence are capable of hybridizing to form a double-stranded region; and whereby the plant is resistant to a fungus expressing at least one gene having substantial homology to the antisense sequence.

10. The transgenic plant of claim 9, wherein the antisense sequence has at least 80% homology to at least one additional *Phytophthora* cutinase gene and, whereby the plant is resistant to a fungus expressing at least one gene having substantial homology to the at least one additional *Phytophthora* cutinase gene.

11. The transgenic plant of claim 9, wherein the transcript of the antisense sequence and the transcript of the sense sequence form a double stranded region.

12. The transgenic plant of claim 10, wherein the transcript of the antisense sequence and the transcript of the sense sequence form a double stranded region.

13. The transgenic plant of claim 9, further comprising:

(c) a second antisense sequence having at least 80% homology to a second *Phytophthora* cutinase gene; and (d) a second sense sequence substantially complementary to the second antisense sequence;

wherein a transcript of the second antisense sequence and a transcript of the second sense sequence are capable of hybridizing to form a double-stranded region; and whereby the plant is resistant to a fungus expressing at least gene having substantial homology to the second antisense *Phytophthora* cutinase gene.

14. The transgenic plant of claim 13, wherein the transcript of the second antisense sequence and the transcript of the second sense sequence form a double stranded region.

15. The transgenic plant of claim 9, wherein the *Phytophthora* cutinase gene is selected from the group consisting of SEQ ID NOs: 13, 15, 21, 30 and 32-37.

16. The transgenic plant of claim 13, wherein the *Phytophthora* cutinase gene and the second *Phytophthora* cutinase gene are selected from the group consisting of SEQ ID NOs: 13, 15, 21, 30 and 32-37.

* * * * *

UNITED STATES PATENT AND TRADEMARK OFFICE

CERTIFICATE OF CORRECTION

PATENT NO. : 8,461,416 B2
APPLICATION NO. : 13/171117
DATED : June 11, 2013
INVENTOR(S) : Niblett It is certified that error appears in the above-identified patent and that said Letters Patent is hereby corrected as shown below:

In the Specification

Column 51, Table 9, Sequence ID NO 21, Line 10:

Please correct

“ACTCTGCTTCCGTTGGCTCTGTGCGTTGAACCTTGCTTTCTTGATCC”

to read

-- ACTCTGCTTCCGTTGGCTCTGTGCGTTGACCTTGCTTTCTTGATCC --

Signed and Sealed this
Fourth Day of August, 2015

Michelle K. Lee
*Director of the United States Patent and Trademark Office*